United States Patent
Wang et al.

(10) Patent No.: US 10,829,483 B2
(45) Date of Patent: Nov. 10, 2020

(54) THIOPHENE, MANUFACTURING METHOD THEREOF, AND PHARMACEUTICAL APPLICATION OF SAME

(71) Applicants: CSTONE PHARMACEUTICAL (SUZHOU) CO., LTD., Jiangsu (CN); CSTONE PHARMACEUTICALS (SHANGHAI) CO., LTD., Shanghai (CN); CSTONE PHARMACEUTICALS, Grand Cayman (KY)

(72) Inventors: Jianfei Wang, Shanghai (CN); Yang Zhang, Shanghai (CN); Wenyuan Zhu, Shanghai (CN); Shuhui Chen, Shanghai (CN)

(73) Assignees: CSTONE PHARMACEUTICAL (SUZHOU) CO., LTD., Jiangsu (CN); CSTONE PHARMACEUTICALS (SHANGHAI) CO., LTD., Shanghai (CN); CSTONE PHARMACEUTICALS, Grand Cayman (KY)

( * ) Notice: Subject to any disclaimer, the term of this patent is extended or adjusted under 35 U.S.C. 154(b) by 73 days.

(21) Appl. No.: 16/303,767

(22) PCT Filed: May 23, 2017

(86) PCT No.: PCT/CN2017/085458
§ 371 (c)(1),
(2) Date: Nov. 21, 2018

(87) PCT Pub. No.: WO2017/202291
PCT Pub. Date: Nov. 30, 2017

(65) Prior Publication Data
US 2020/0140423 A1    May 7, 2020

(30) Foreign Application Priority Data

May 23, 2016  (CN) .......................... 2016 1 0343321

(51) Int. Cl.
| | |
|---|---|
| *C07D 409/04* | (2006.01) |
| *A61P 19/06* | (2006.01) |
| *C07D 409/14* | (2006.01) |
| *C07D 495/04* | (2006.01) |
| *C07D 405/04* | (2006.01) |

(52) U.S. Cl.
CPC ............ *C07D 409/04* (2013.01); *A61P 19/06* (2018.01); *C07D 405/04* (2013.01); *C07D 409/14* (2013.01); *C07D 495/04* (2013.01)

(58) Field of Classification Search
CPC ... C07D 409/04; C07D 409/14; C07D 495/04
See application file for complete search history.

(56) References Cited

U.S. PATENT DOCUMENTS

| | | | |
|---|---|---|---|
| 2013/0296345 A1 | 11/2013 | Quart | |
| 2015/0284358 A1 | 10/2015 | Maruyama et al. | |

FOREIGN PATENT DOCUMENTS

| | | |
|---|---|---|
| CN | 105399694 A | 3/2016 |
| JP | 2011-504935 A | 2/2011 |
| WO | WO-2009070740 A2 | 6/2009 |
| WO | 2012050589 A1 | 4/2012 |
| WO | 2014077285 A1 | 5/2014 |

OTHER PUBLICATIONS

First Office Action issued in the counterpart Japanese application No. 2019-514169 dated Oct. 23, 2019.
Extended European Search Report issued in the counterpart European application No. 17802137.4 dated Oct. 7, 2019.
Database Registry[Online] Chemical Abstracts Service, Columbus, Ohio, US, Sep. 15, 2016, XP002794273, retrieved from STN Database accession No. 1994072-20-6, CAS RN: 1994033-22-5.
Database Registry[Online] Chemical Abstracts Service, Columbus, Ohio, US, Sep. 30, 2016, XP002794274, retrieved from STN Database accession No. 2002753-00-4.
Database Registry[Online] Chemical Abstracts Service, Columbus, Ohio, US, Oct. 3, 2016, XP002794275, retrieved from STN Database accession No. 2004354-51-0.
Database Registry[Online] Chemical Abstracts Service, Columbus, Ohio, US, Nov. 11, 2016, XP002794276, retrieved from STN Database accession No. 2029569-74-0.

(Continued)

*Primary Examiner* — Joseph R Kosack
(74) *Attorney, Agent, or Firm* — Harness, Dickey & Pierce, P.L.C.

(57) ABSTRACT

The present invention discloses a thiophene used as a uric acid transporter (URAT1) inhibitor and application of the thiophene in preparing a pharmaceutical product for treating a disease related to abnormal uric acid levels, specifically in preparing a pharmaceutical product for treating hyperuricemia and gouty arthritis. The invention specifically relates to a compound as represented by formula (I) or a pharmaceutically acceptable salt thereof.

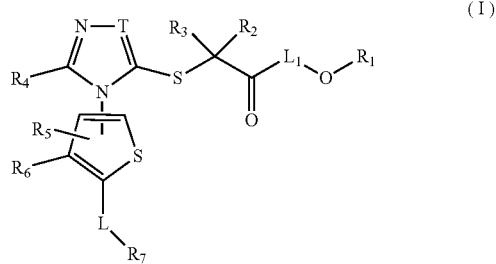

19 Claims, No Drawings

(56) References Cited

OTHER PUBLICATIONS

First Office Action issued in the counterpart Indonesian application No. PID201810594 dated Feb. 17, 2020.
International Search Report of PCT/CN2017/085458 dated Aug. 30, 2017.
Written Opinion of PCT/CN2017/085458 dated Aug. 30, 2017.
Berge et al., "pharmaceutical Salts", Journal of pharmaceutical Science 1977, vol. 66, No. 1, p. 1-19.
Maehr, "A proposed new convention for graphic presentation of molecular geometry and topography", J.Chem. Ed.1985, vol. 62, No. 2, p. 114-120.
Ukrorgsyntez Ltd., "RN:1866384-17-9", STN Registry, Feb. 15, 2016.
Aurora Fine Chemicals,"RN: 1517276-53-7", STN Registry,Jan. 12, 2014.
Aurora Fine Chemicals,"RN: 1516744-39-0", STN Registry, Jan. 10, 2014.
Aurora Fine Chemicals, "RN: 1506948-73-7", STN Registry, Dec. 30, 2013.
Aurora Fine Chemicals, "RN: 1506308-08-2", STN Registry, Dec. 29, 2013.
Examination Report of counterpart Australian patent application No. 2017270858 dated Apr. 10, 2019.
CAS RN:1855720-06-7, STN Entry Date: Jan. 29, 2016, 24[[4-(4-methyl-3-thienyl)4H-1,2,4-triazol-3-yl]thio]acetic acid.
CAS RN:1521435-55-1, STN Entry Date: Jan. 16, 2014, 2-[[5-ethyl-4-(3-thienyl)4H-1,2,4-triazol-3-yl]thio]acetic acid).
CAS RN:1511997-55-9, STN Entry Date: Jan. 6, 2014, 2-[[5-methyl-4-(3-thienyl)4H-1,2,4-triazol-3-yl]thio]acetic acid).
CAS RN:1511846-55-1, STN Entry Date: Jan. 5, 2014, 2[[4,5-dihydro-5-oxo-4-(3-thienyl)-1H-1,2,4-triazol-3-yl]thio]acetic acid).
CAS RN:1500276-99-2, STN Entry Date: Dec. 22, 2013, 2-[[4-(3-thienyl)-4H-1,2,4-triazol-3-yl]thio]acetic acid).
First Office Action issued in Korean Application No. 10-2018-7037287 dated Jul. 30, 2020.
Machine translation of First Office Action issued in Korean Application No. 10-2018-7037287 dated Jul. 30, 2020.

THIOPHENE, MANUFACTURING METHOD THEREOF, AND PHARMACEUTICAL APPLICATION OF SAME

CROSS REFERENCE TO RELATED APPLICATIONS

This application is a U.S. National Phase Application under 35 U.S.C. 371 of International Application No. PCT/CN2017/085458 filed on May 23, 2017. This application claims priority to Chinese Application No. 201610343321.0 filed on May 23, 2016. The entire disclosures of all of the above applications are incorporated herein by reference.

FIELD OF INVENTION

The present invention discloses a thiophene used as a uric acid transporter (URAT1) inhibitor and application of the thiophene in preparing a pharmaceutical product for treating a disease related to abnormal uric acid levels, specifically in preparing a pharmaceutical product for treating hyperuricemia and gouty arthritis. The invention specifically relates to a compound as represented by formula (I) or a pharmaceutically acceptable salt thereof.

BACKGROUND OF INVENTION

Uric acid is a metabolite of terpenoids in animals. For humans, uric acid is excreted in human body as the end-product of purine metabolism through the gastrointestinal tractor in urine due to the lack of uricases, which continue to oxidatively degrade uric acid in the human body, and renal excretion is the main pathway for uric acid excretion in humans. The upper limit of normal uric acid concentration in the human body is 400 umol/L (6.8 mg/dL) for male and 360 umol/L (6 mg/dL) for female. Abnormal uric acid levels in the human body are often due to the increased production of uric acidor decreased excretion of uric acid. Symptoms associated with abnormal levels of uric acid include hyperuricemia, gout, etc.

Hyperuricemia refers to a symptom in which the metabolism of purine substances in the human body is disordered, resulting in an increased uric acid production or decrease in excretion, and an abnormally high level of uric acid in the blood. Gouty arthritis means that when concentration of uric acid is more than 7 mg/dL in human blood, uric acid is deposited as a monosodium salt in the joints, cartilage and kidneys, resulting in excessive reaction (sensitivity) of the body's immune system and causing painful inflammation. The general attack sites are big toe joint, ankle joint, knee joint and so on. Red, swollen, hot, and severe pain appear in the attack site of acute gout, which usually occurs in midnight and can make people wake up from sleep. In the early stage of gout, the attack is more common in the joints of the lower limbs. Hyperuricemia is the pathological basis of gouty arthritis, and the use of drugs to decrease blood uric acid concentration is one of the common methods for preventing gouty arthritis.

In Europe and USA, the attack of hyperuricemia and gout disease is on the rise. Researches on the epidemiology have shown that the incidence of gouty arthritis accounts for 1-2% of the total population and is the main type of arthritis in adult males. Bloomberg News estimates that there will be 17.7 million gout patients in 2021. In China, the survey shows that 25.3% of the population has a high blood uric acid concentration and 0.36% has gout diseases among the population aged 20 to 74. At present, clinical treatment drugs mainly include 1) drugs by inhibition of uric acid-producing, such as xanthine oxidase inhibitors allopurinol and febuxostat; 2) drugs by promoting uric acid excretion, such as probenecid and benzbromarone; 3) inflammation inhibitors, such as colchicine and so on. These drugs have certain defects in treatment, including poor efficacy, large side effects, and high cost are some main bottlenecks in their clinical application. It has been reported that blood uric acid levels of 40%-70% of patients who have received standard treatment did not meet the expected therapeutic goals (<6 mg/dL).

As a uric acid excretion agent, its mechanism of action is to reduce the reabsorption of uric acid by inhibiting the URAT1 transporter on the brush-border membrane of the proximal convoluted tubule. Uric acid is the metabolite of purine in the body which is mainly filtered by glomerulus in the original form, reabsorbed and re-secreted by the renal tubules, and finally excreted in urine, very small part can be secreted into the enterocoel by mesenteric cells. The S1 segment of the proximal convoluted tubule is the site of uric acid reabsorption, and 98%-100% of the filtered uric acid enters into the epithelial cell through the uric acid transporter URAT1 and the organic anionic transporter OAT4 on the brush-border membrane of tubular epithelial cells. The uric acid entering the epithelial cells is reabsorbed into the capillaries around the tubules via the renal tubular basolateral membrane. The S2 segment of the proximal convoluted tubule is the site of re-secretion of uric acid, and the amount secreted is about 50% of the amount of glomerular filtration. The uric acid in the renal interstitial first enters into the epithelial cells through the anionic transporters OAT1, OAT3 on the basolateral membrane of the tubular epithelial cells. The uric acid entering the epithelial cells passes through another anionic transporter MRP4 on the brush-border membrane and is discharged into the small lumen. The S3 segment of the proximal convoluted tubule may be the reabsorption site after uric acid secretion, the amount of reabsorption is about 40% of the amount of the glomerular filtration, and similar to the first step of reabsorption, where URAT1 may be the key reabsorption transporter. Therefore, if the urate transporter URAT1 can be significantly inhibited, it will enhance the excretion of uric acid in the body, thereby lowering blood uric acid level and reducing the possibility of gout attack.

The first URAT1 inhibitor Zurampic (Leinurad) was approved by the FDA in December 2015. The 200 mg dose was approved in combination with xanthine oxidase inhibitor XOI (such as Febuxostat, etc.) for the treatment of hyperuricemia and gouty arthritis, but the additive effect of combination was not very significant compared with the xanthine oxidase inhibitor alone. The 400 mg dose of Zurampic was not approved due to significant toxic side effects at high doses (the incidence of kidney-related adverse events, especially the incidence of kidney stones). Therefore, the FDA required the Zurampic label to be filled with a black box warning to warn the medical staff acute kidney failure caused by Zulampic, especially when not used in combination with XOI, and if the over-approved dose of Zurampic used, the risk of renal failure is even higher. Meanwhile, the FDA asked AstraZeneca to continue its evaluation on kidney and cardiovascular safety after Zurampic marketed. Therefore, there is a strong demand to develop a novel and safe drug for lowing blood uric acid.

The present invention reports the synthesis of a class of promoting uric acid excretion thiophene compounds as inhibitors of urate transporters (URAT1), and their use in disorders of uric acid levels, particularly in hyperuricemia and gouty arthritis.

CONTENT OF THE PRESENT INVENTION

The present invention provides a compound represented by formula (I), a pharmaceutically acceptable salt and a tautomer thereof,

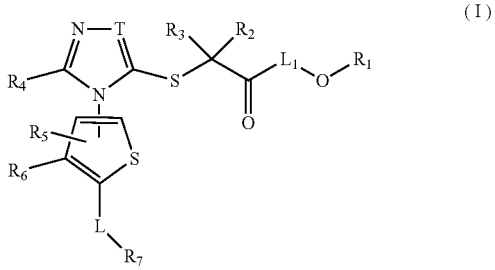

wherein,

T is selected from N or CH;

$R_1$ is selected from H, or selected from the group consisting of $C_{1-6}$ alkyl and $C_{1-6}$ heteroalkyl, each of which is optionally substituted by 1, 2 or 3 of R;

each of $R_2$, $R_3$ is independently selected from H, F, Cl, Br, I, OH, CN, $NH_2$, COOH, or independently selected from the group consisting of $C_{1-6}$ alkyl, $C_{1-6}$ heteroalkyl, phenyl and 5 to 6 membered heteroaryl, each of which is optionally substituted by 1, 2 or 3 of R;

or, $R_2$ and $R_3$ are linked together to form $C_{3-6}$ cycloalkyl or 3 to 6 membered heterocycloalkyl, each of which is optionally substituted by 1, 2 or 3 of R;

$R_4$ is selected from H, F, Cl, Br, I, OH, CN, $NH_2$, COOH, or selected from the group consisting of $C_{1-3}$ alkyl and $C_{1-3}$ heteroalkyl, each of which is optionally substituted by 1, 2 or 3 of R;

$R_5$ is selected from H, F, Cl, Br, I, OH, CN, $NH_2$, or selected from the group consisting of $C_{1-3}$ alkyl and $C_{1-3}$ heteroalkyl, each of which is optionally substituted by 1, 2 or 3 of R;

$R_6$ is selected from H, F, Cl, Br, I, OH, CN, $NH_2$, or selected from the group consisting of $C_{1-3}$ alkyl and $C_{1-3}$ heteroalkyl, each of which is optionally substituted by 1, 2 or 3 of R;

or, $R_5$ and $R_6$ are linked together to form $C_{3-6}$ cycloalkyl or 3 to 6 membered heterocycloalkyl, each of which is optionally substituted by 1, 2 or 3 of R;

L is selected from a single bond, —C(=O)O—, —C(=O)NH—;

$L_1$ is selected from a single bond, —NH—;

$R_7$ is selected from H, F, Cl, Br, I, OH, CN, $NH_2$, COOH, or selected from the group consisting of $C_{1-6}$ alkyl, $C_{1-6}$ heteroalkyl, $C_{3-6}$ cycloalkyl, 3 to 6 membered heterocycloalkyl, phenyl and 5 to 6 membered heteroaryl, each of which is optionally substituted by 1, 2 or 3 of R;

or, $R_6$ and $R_7$ are linked together to form $C_{3-6}$ cycloalkyl, $C_{3-6}$ heterocycloalkyl, phenyl and 5 to 6 membered heteroaryl, each of which is optionally substituted by 1, 2 or 3 of R;

R is selected from F, Cl, Br, I, OH, CN, $NH_2$, COOH, C(=O)$NH_2$, or selected from the group consisting of $C_{1-6}$ alkyl, $C_{1-6}$ heteroalkyl, $C_{3-6}$ cycloalkyl and 3 to 6 membered heteroalkyl, each of which is optionally substituted by 1, 2 or 3 of R';

R' is selected from F, Cl, Br, I, OH, CN, $NH_2$, COOH, Me, Et, $CF_3$, $CHF_2$, $CH_2F$, $NHCH_3$, $N(CH_3)_2$;

"hetero" refers to a heteroatom or a heteroatomic group, which is selected from the group consisting of —C(=O)NH—, —NH—, —C(=NH)—, —S(=O)$_2$NH—, —S(=O)NH—, —O—, —S—, =O, =S, —O—N=, —C(=O)O—, —C(=O)—, —C(=S)—, —S(=O)—, —S(=O)$_2$— and —NHC(=O)NH—;

in any case above, the number of the heteroatom or the heteroatomic group is independently selected from 1, 2 or 3, respectively.

In certain embodiments of the present invention, R is selected from F, Cl, Br, I, OH, CN, $NH_2$, COOH, C(=O)$NH_2$, or selected from $C_{1-4}$ alkyl, N,N'-di($C_{1-2}$ alkyl)amino, $C_{1-3}$ alkyl-NH—, $C_{1-3}$ alkyl-O—, $C_{1-3}$ alkyl-S(=O)$_2$—, $C_{1-3}$ alkyl-S(=O)—, each of which is optionally substituted by 1, 2 or 3 of R'.

In certain embodiments of the present invention, R is selected from F, Cl, Br, I, OH, CN, $NH_2$, COOH, C(=O)$NH_2$, Me, $CF_3$, Et, $NH(CH_3)$, $N(CH_3)_2$,

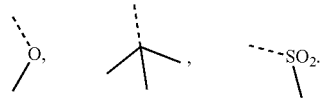

In certain embodiments of the present invention, the moiety

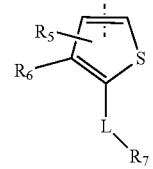

is selected from

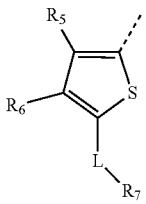 or 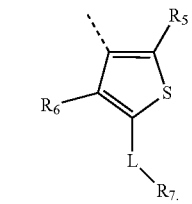

In certain embodiments of the present invention, $R_1$ is selected from H, or selected from the group consisting of $C_{1-3}$ alkyl and $C_{1-3}$ heteroalkyl, each of which is optionally substituted with 1, 2 or 3 of R.

In certain embodiments of the present invention, $R_1$ is selected from H, Me, Et.

In certain embodiments of the present invention, each of $R_2$, $R_3$ is independently selected from H, F, Cl, Br, I, OH, CN, $NH_2$, COOH, or independently selected from the group consisting of $C_{1-3}$ alkyl, $C_{1-3}$ heteroalkyl and phenyl, each of which is optionally substituted by 1, 2 or 3 of R.

In certain embodiments of the present invention, each of $R_2$, $R_3$ is independently selected from H, Me, Et,

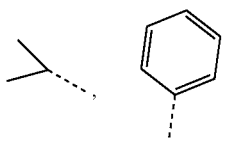

In certain embodiments of the present invention, $R_2$ and $R_3$ are linked together to form $C_{4-5}$ cycloalkyl, which is optionally substituted by 1, 2 or 3 of R.

In certain embodiments of the present invention, $R_2$ and $R_3$ are linked together, and the moiety

is selected from

In certain embodiments of the present invention, $R_5$ is selected from H, F, Cl, Br, I, OH, CN, $NH_2$, Me, Et.

In certain embodiments of the present invention, $R_6$ is selected from H, F, Cl, Br, I, OH, CN, $NH_2$, Me, Et.

In certain embodiments of the present invention, $R_5$ and $R_6$ are linked together, and the moiety

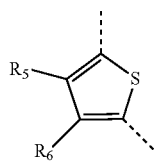

is selected from

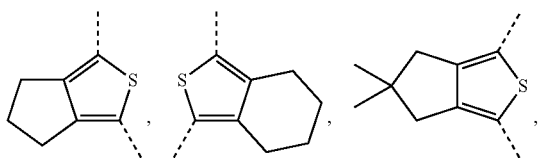

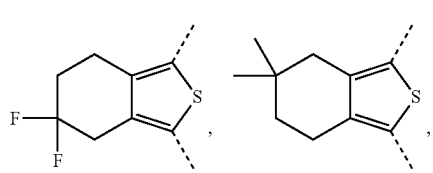

-continued

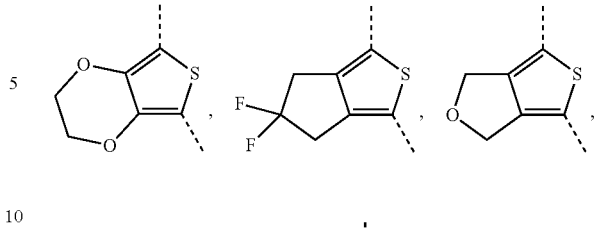

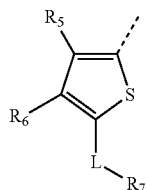

In certain embodiments of the present invention, $R_6$ and $R_7$ are linked together, and the moiety

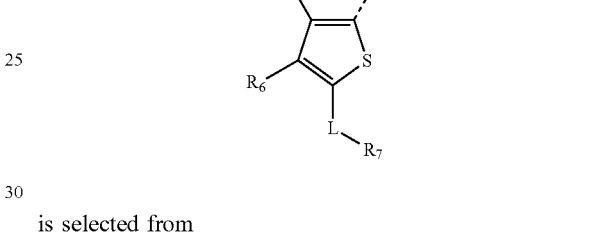

is selected from

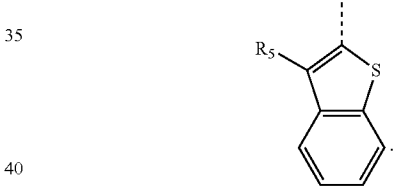

In certain embodiments of the present invention, $R_6$ and $R_7$ are linked together, and the moiety

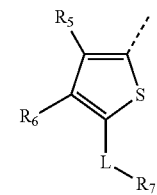

is selected from

In certain embodiments of the present invention, $R_6$ and $R_7$ are linked together, and the moiety

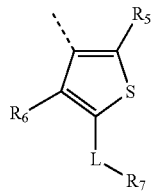

is selected from

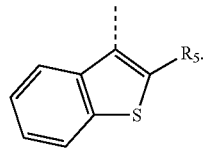

In certain embodiments of the present invention, $R_6$ and $R_7$ are linked, and the moiety

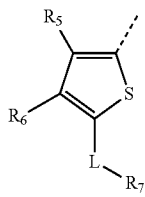

is selected from

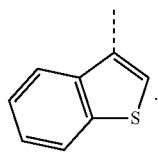

In certain embodiments of the present invention, $R_7$ is selected from H, F, Cl, Br, I, OH, CN, $NH_2$, COOH, or selected from the group consisting of $C_{1-3}$ alkyl, C(=O)$OC_{1-3}$ alkyl, C(=O)N($C_{1-3}$ alkyl)$C_{1-3}$ alkyl, $C_{3-6}$ cycloalkyl, phenyl, pyrazolyl, imidazolyl, thiazolyl, oxazolyl, isoxazolyl, isothiazolyl, pyridyl and pyrimidyl, each of which is optionally substituted by 1, 2 or 3 of R.

In certain embodiments of the present invention, $R_7$ is selected from H, F, Cl, Br, I, OH, CN, $NH_2$, COOH, or selected from

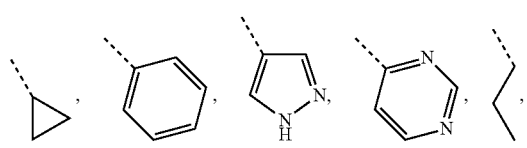

each of which is optionally substituted by 1, 2 or 3 of R.

In certain embodiments of the present invention, $R_7$ is selected from H, F, Cl, Br, I, OH, CN, $NH_2$, COOH,

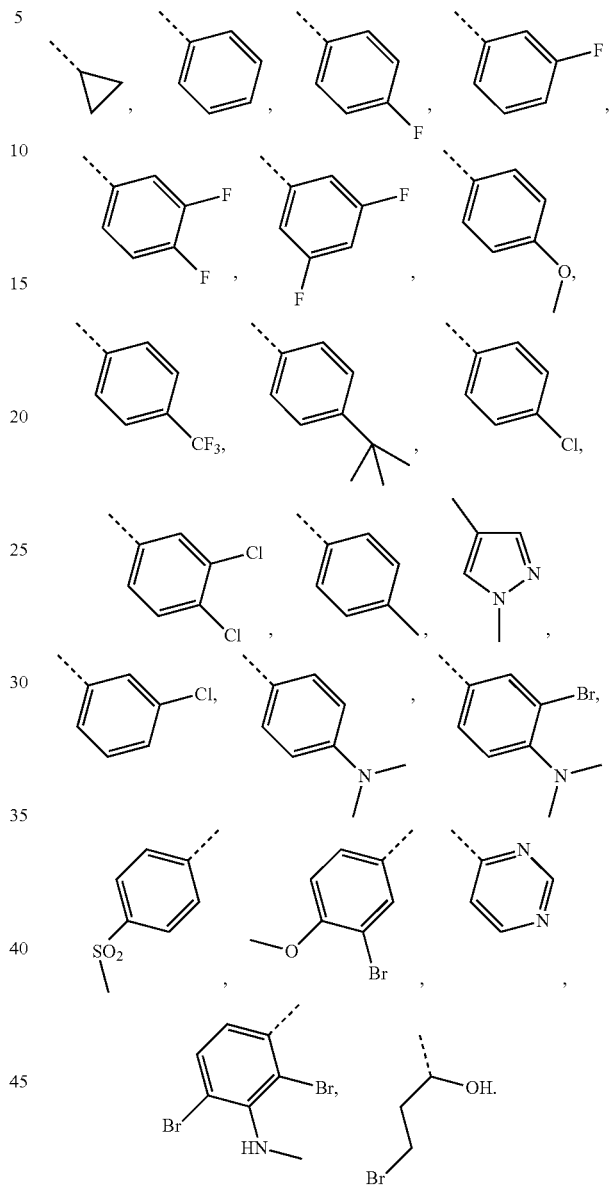

In certain embodiments of the present invention, the moiety -L-$R_7$ is selected from H,

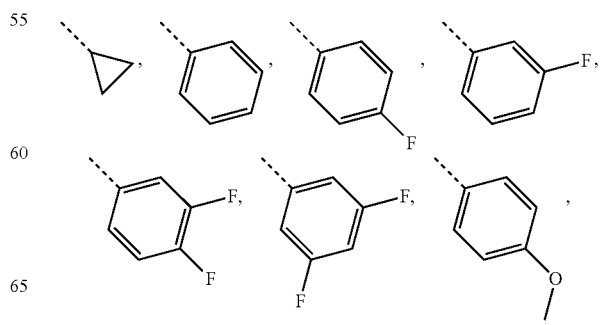

-continued

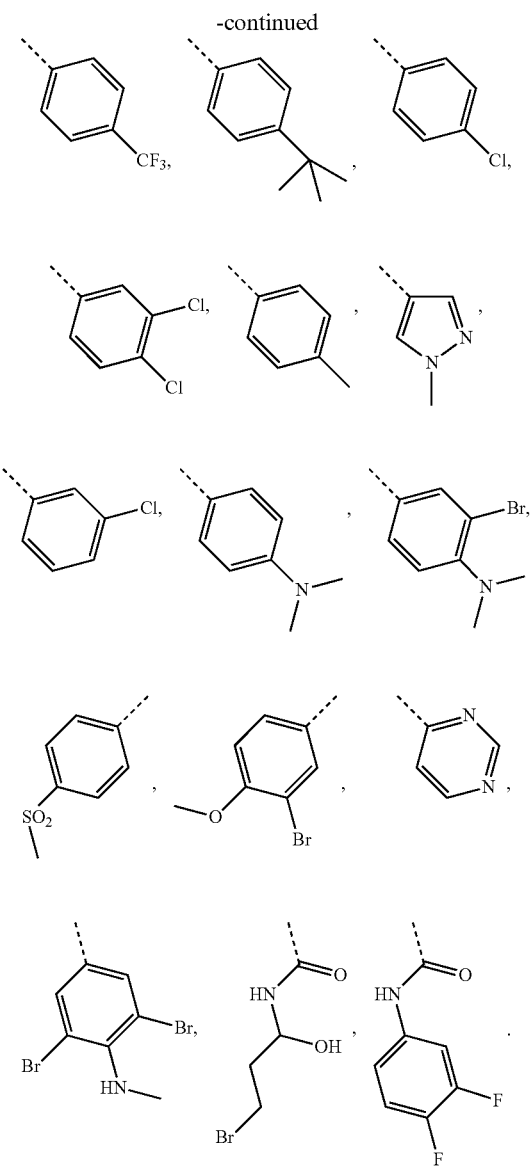

In certain embodiments of the present invention, $R_4$ is selected from F, Cl, Br, I, OH, CN, $NH_2$, COOH, Me, Et, n-propyl, i-propyl, $CF_3$, $CHF_2$, $CH_2F$, $NHCH_3$, $N(CH_3)_2$.

In certain embodiments of the present invention, R is selected from F, Cl, Br, I, OH, CN, $NH_2$, COOH, C(=O)$NH_2$, or selected from $C_{1-4}$ alkyl, N,N'-di($C_{1-2}$ alkyl)amino, $C_{1-3}$ alkyl-NH—, $C_{1-3}$ alkyl-O—, $C_{1-3}$ alkyl-S(=O)$_2$—, $C_{1-3}$ alkyl-S(=O)—, each of which is optionally substituted by 1, 2 or 3 of R', and other variables are as defined above.

In certain embodiments of the present invention, R is selected from F, Cl, Br, I, OH, CN, $NH_2$, COOH, C(=O)$NH_2$, Me, $CF_3$, Et, $NH(CH_3)$, $N(CH_3)_2$,

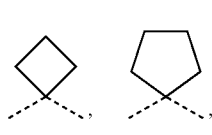

and other variables are as defined above.

In certain embodiments of the present invention, the moiety

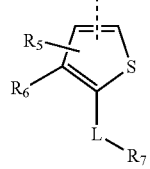

is selected from

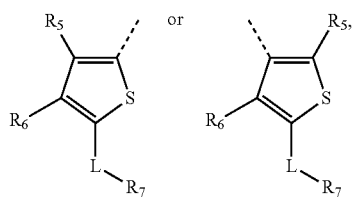

and other variables are as defined above.

In certain embodiments of the present invention, $R_1$ is selected from H, or selected from the group consisting of $C_{1-3}$ alkyl and $C_{1-3}$ heteroalkyl, each of which is optionally substituted by 1, 2 or 3 of R.

In certain embodiments of the present invention, $R_1$ is selected from H, Me, Et, and other variables are as defined above.

In certain embodiments of the present invention, each of $R_2$, $R_3$ is independently selected from H, F, Cl, Br, I, OH, CN, $NH_2$, COOH, or independently selected from the group consisting of $C_{1-3}$ alkyl, $C_{1-3}$ heteroalkyl and phenyl, each of which is optionally substituted with 1, 2 or 3 of R, and other variables are as defined above.

In certain embodiments of the present invention, each of $R_2$, $R_3$ is independently selected from H, Me, Et,

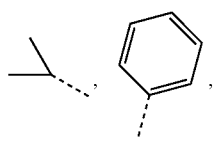

and other variables are as defined above.

In certain embodiments of the present invention, $R_2$ and $R_3$ are linked together to form $C_{4-5}$ cycloalkyl, which is optionally substituted by 1, 2 or 3 of R, and other variables are as defined above.

In certain embodiments of the present invention, $R_2$ and $R_3$ are linked together, and the moiety

is selected from

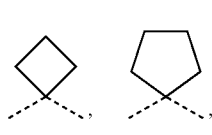

and other variables are as defined above.

In certain embodiments of the present invention, R₅ is selected from H, F, Cl, Br, I, OH, CN, NH₂, Me, Et, and other variables are as defined above.

In certain embodiments of the present invention, R₆ is selected from H, F, Cl, Br, I, OH, CN, NH₂, Me, Et, and other variables are as defined above.

In certain embodiments of the present invention, R₅ and R₆ are linked together, and the moiety

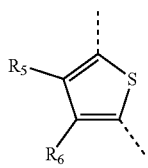

is selected from

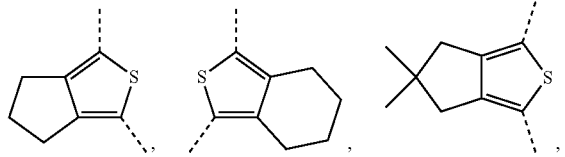

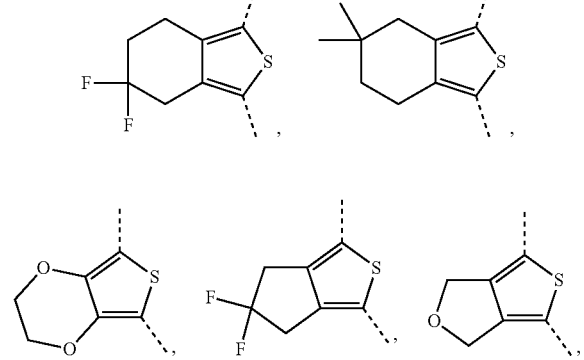

and other variables are as defined above.

In certain embodiments of the present invention, R₆ and R₇ are linked together, and the moiety

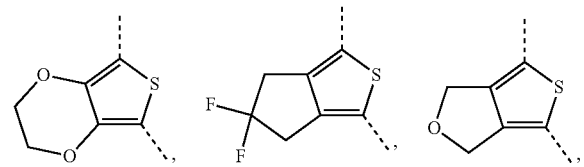

is selected from

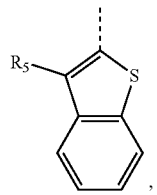

and other variables are as defined above.

In certain embodiments of the present invention, R₆ and R₇ are linked together, and the moiety

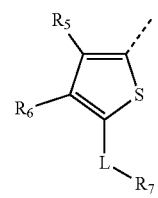

is selected from

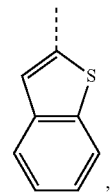

and other variables are as defined above.

In certain embodiments of the present invention, R₆ and R₇ are linked together, and the moiety

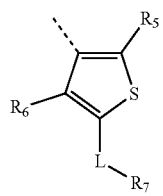

is selected from

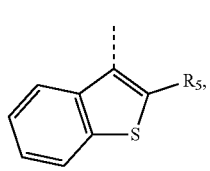

and other variables are as defined above.

In certain embodiments of the present invention, $R_6$ and $R_7$ are linked together, and the moiety

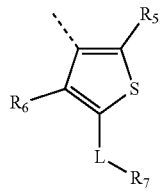

is selected from

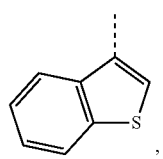

and other variables are as defined above.

In certain embodiments of the present invention, $R_7$ is selected from H, F, Cl, Br, I, OH, CN, $NH_2$, COOH, or selected from the group consisting of $C_{1-3}$ alkyl, $C(=O)OC_{1-3}$ alkyl, $C(=O)N(C_{1-3}$ alkyl$)C_{1-3}$ alkyl, $C_{3-6}$ cycloalkyl, phenyl, pyrazolyl, imidazolyl, thiazolyl, oxazolyl, isoxazolyl, isothiazolyl, pyridyl and pyrimidyl, each of which is optionally substituted by 1, 2 or 3 of R, and other variables are as defined above.

In certain embodiments of the present invention, $R_7$ is selected from H, F, Cl, Br, I, OH, CN, $NH_2$, COOH, or selected from

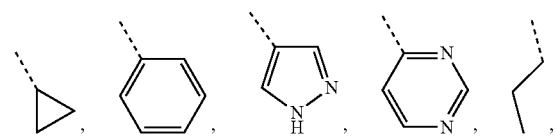

each of which is optionally substituted by 1, 2 or 3 of R, and other variables are as defined above.

In certain embodiments of the present invention, $R_7$ is selected from H, F, Cl, Br, I, OH, CN, $NH_2$, COOH,

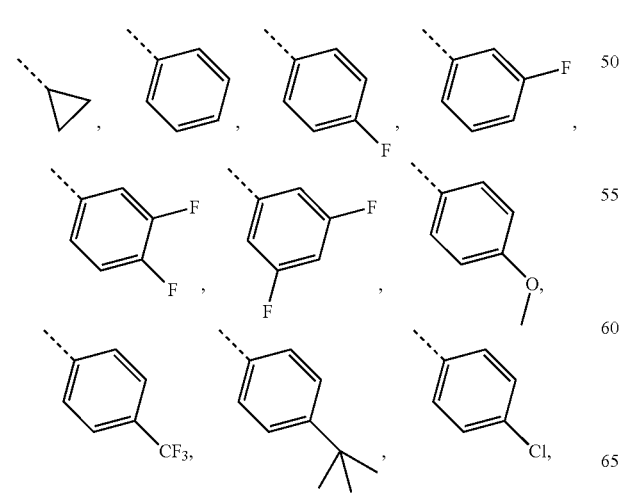

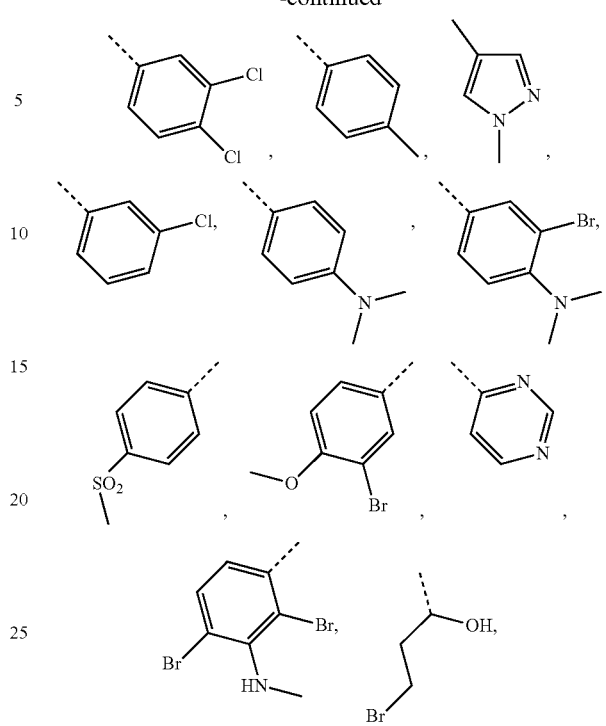

and other variables are as defined above.

In certain embodiments of the present invention, the moiety -L-$R_7$ is selected from H,

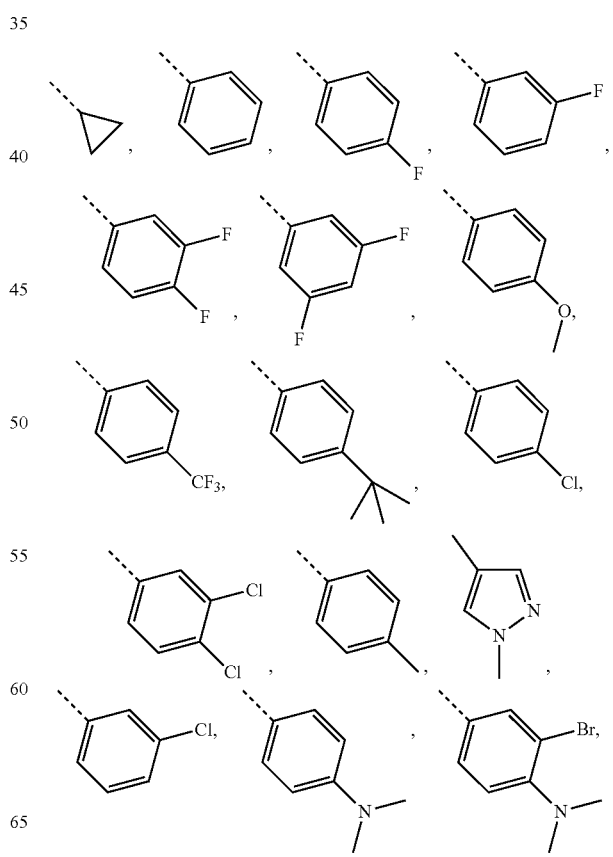

-continued

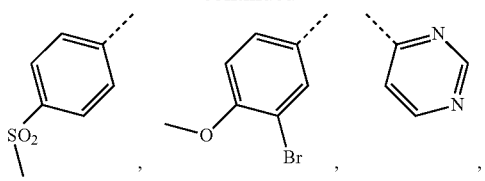

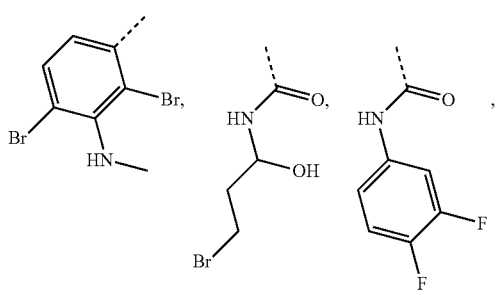

and other variables are as defined above.

In certain embodiments of the present invention, $R_4$ is selected from F, Cl, Br, I, OH, CN, $NH_2$, COOH, Me, Et, n-propyl, i-propyl, $CF_3$, $CHF_2$, $CH_2F$, $NHCH_3$, $N(CH_3)_2$, and other variables are as defined above.

In certain embodiments of the present invention, the compound, the pharmaceutically acceptable salt and the tautomer thereof, is selected from i.

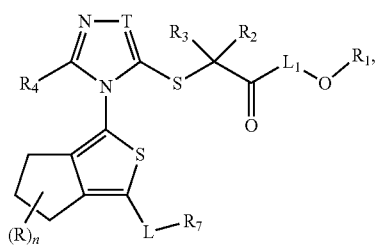
(I-1)

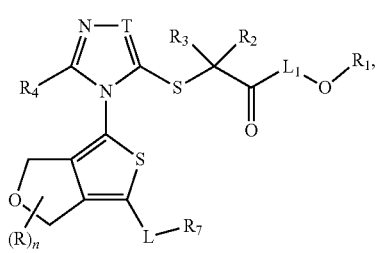
(I-2)

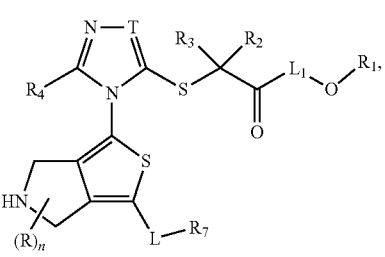
(I-3)

-continued

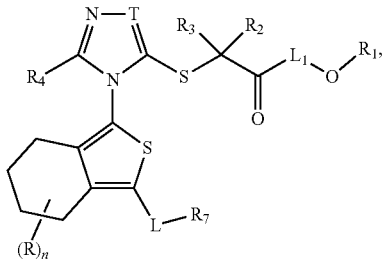
(I-4)

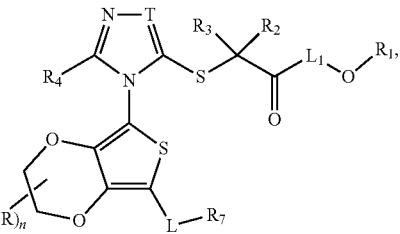
(I-5)

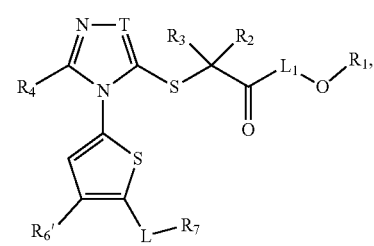
(I-6)

wherein,
n is selected from 0, 1, 2 or 3;
$R_6'$ is selected from H, F, Cl, Br, I, OH, $NH_2$, Me, Et, n-propyl, i-propyl, $CF_3$, $CHF_2$, $CH_2F$, $NHCH_3$, $N(CH_3)_2$;
$R_1$, $R_2$, $R_3$, $R_4$, $R_7$, T, L, $L_1$ are as defined above.

The present invention also contains other embodiments which are combined arbitrarily by the aforesaid variables.

The compound of the present invention is selected from the group consisting of

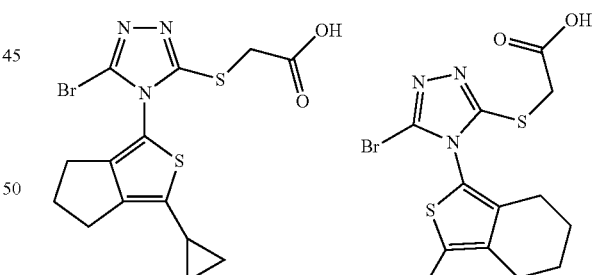

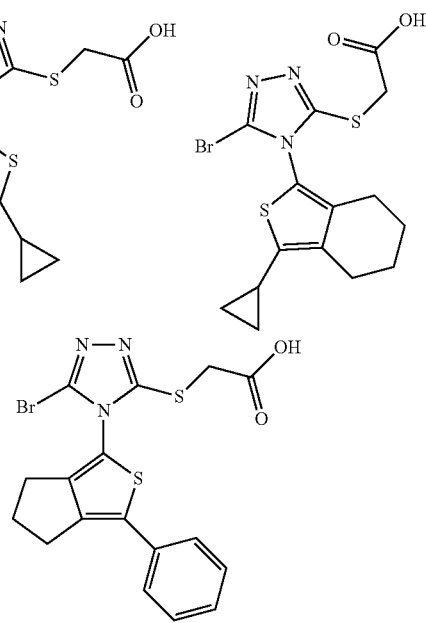

-continued
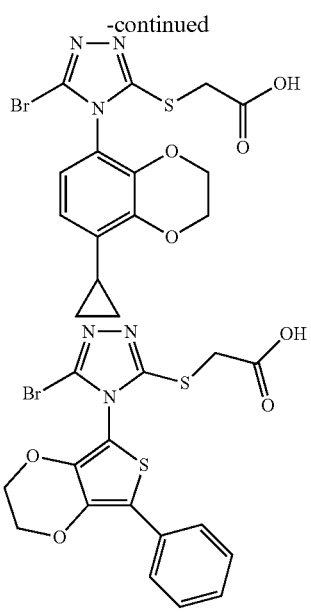
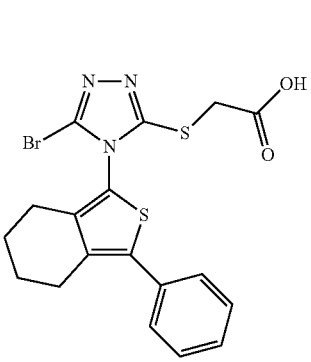
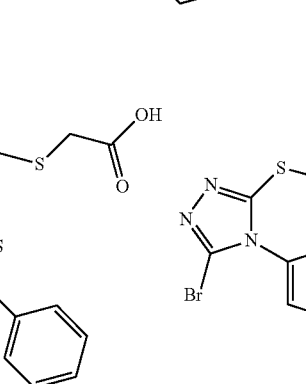
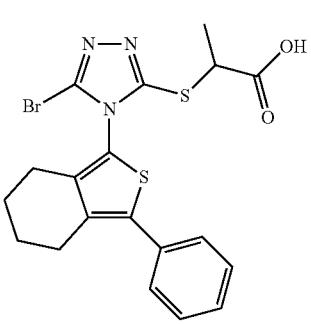
-continued
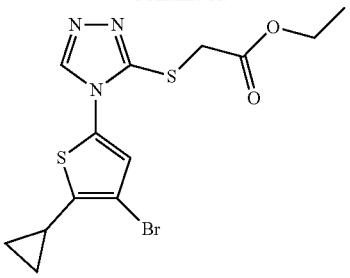
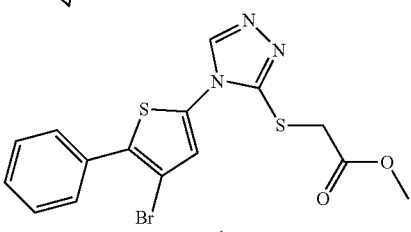
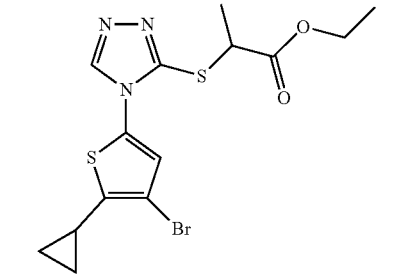
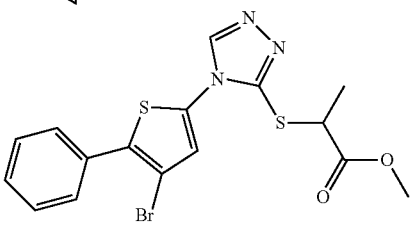
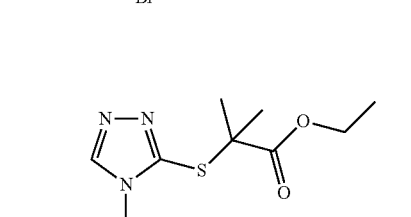
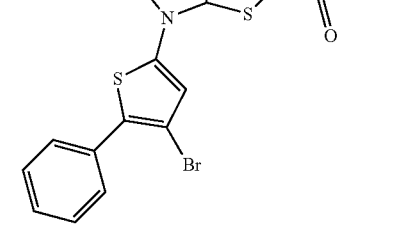

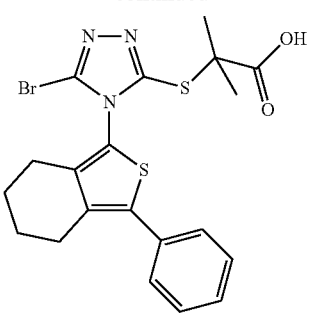
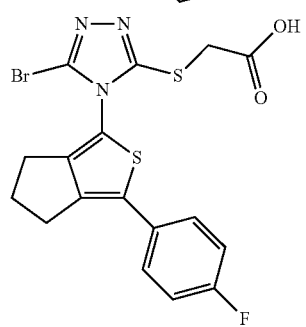
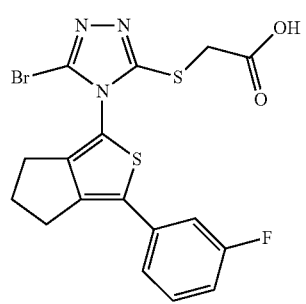
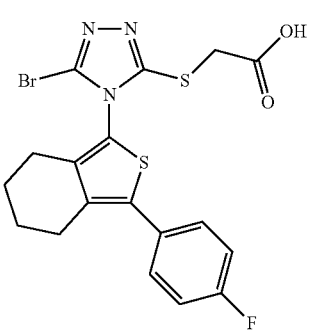
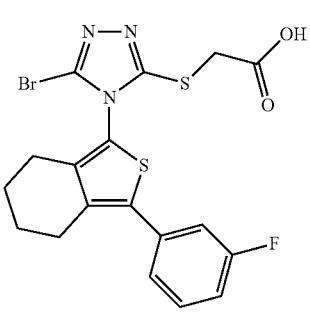
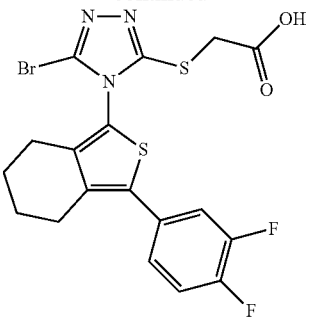
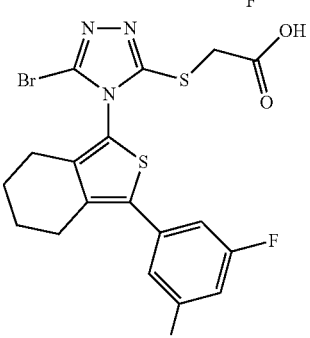
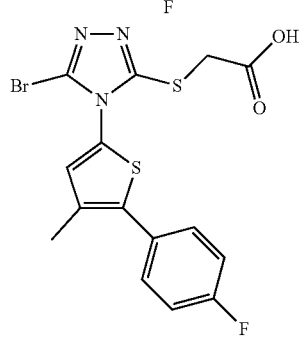
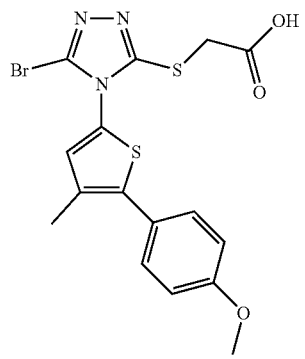
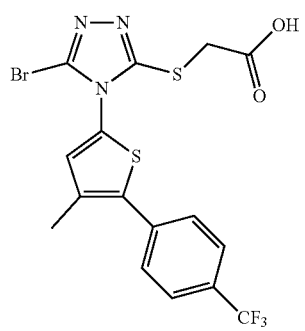

-continued
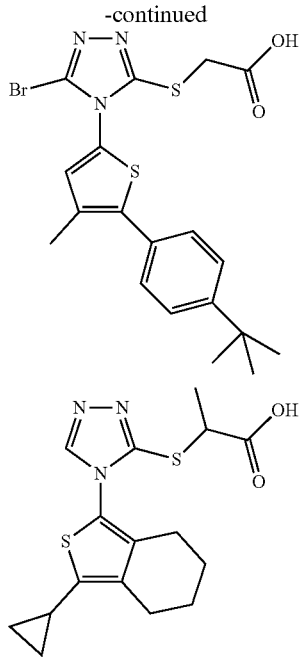
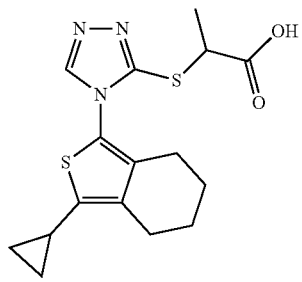
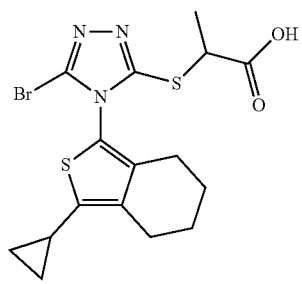
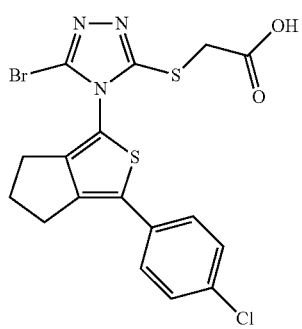
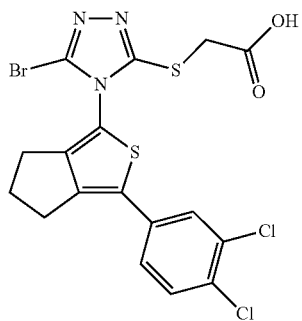
-continued
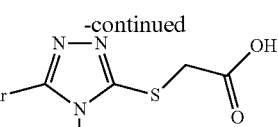
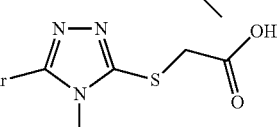
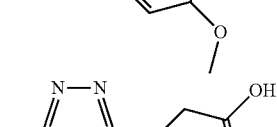
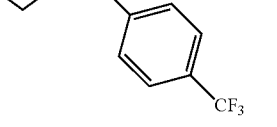
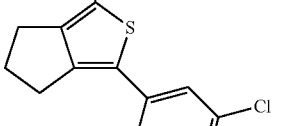
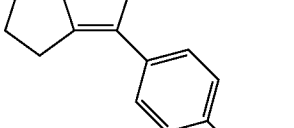

-continued
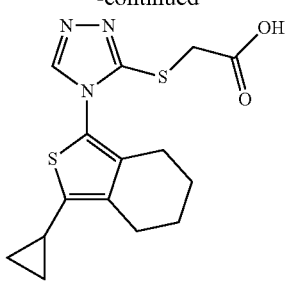
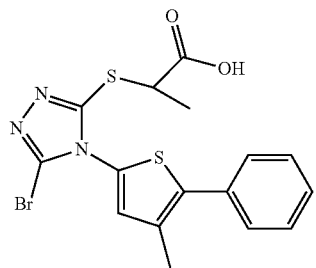
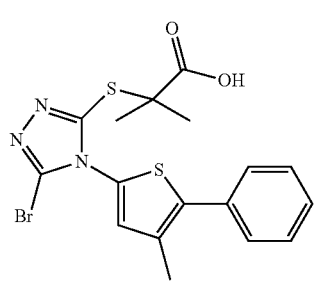
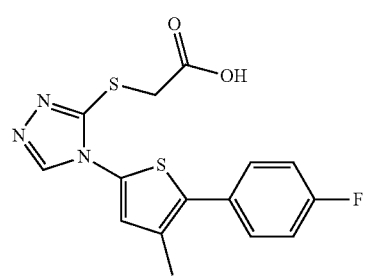
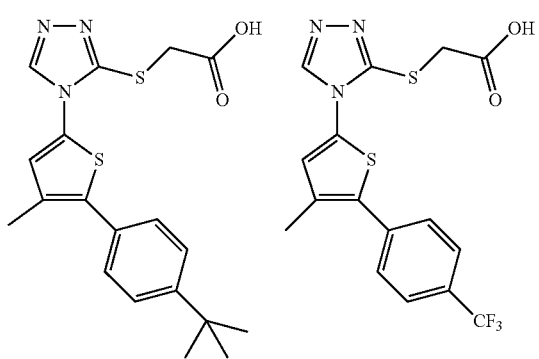
-continued
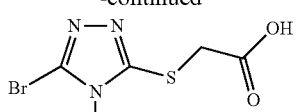
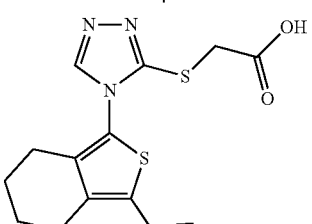
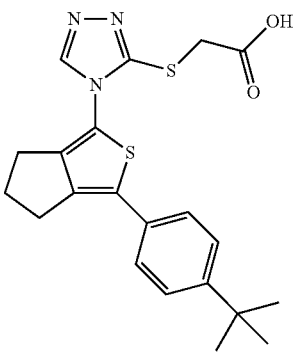
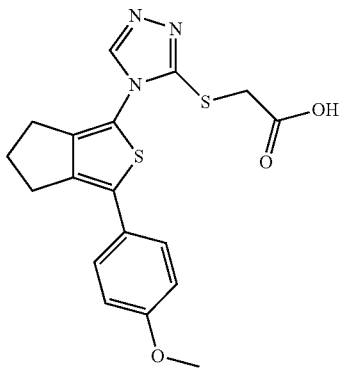
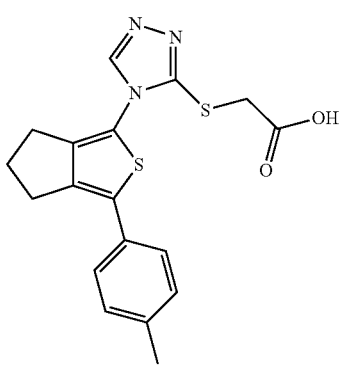

-continued
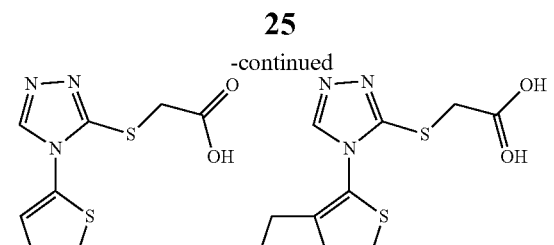
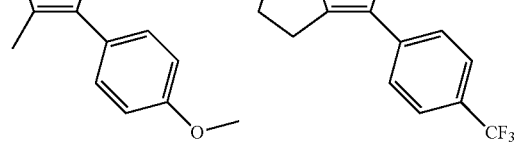
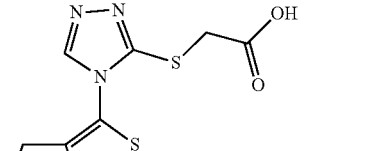
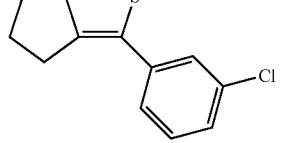
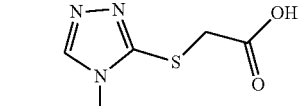
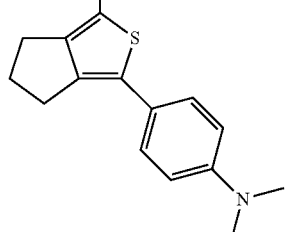
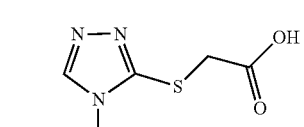
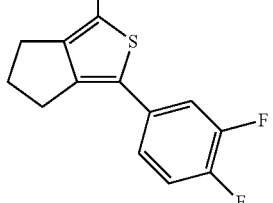
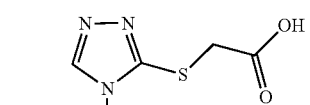
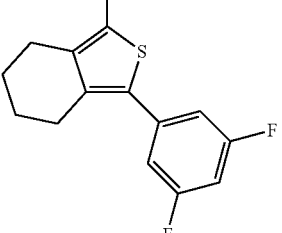
-continued
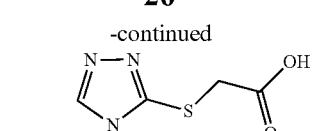
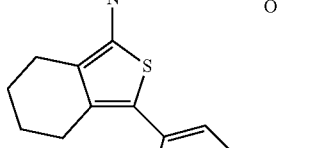
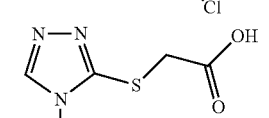
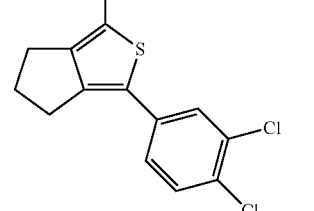
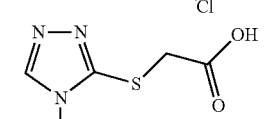
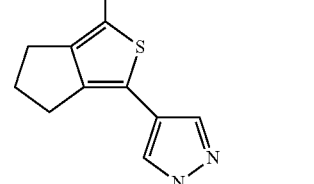
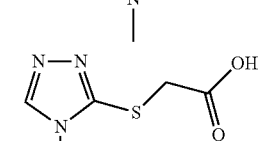
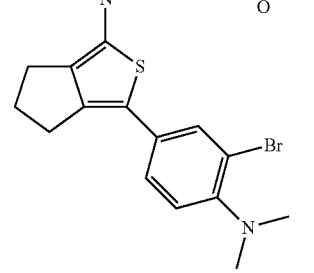
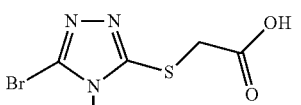
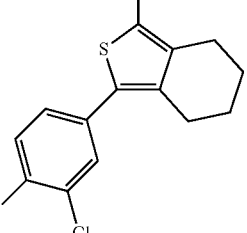

-continued
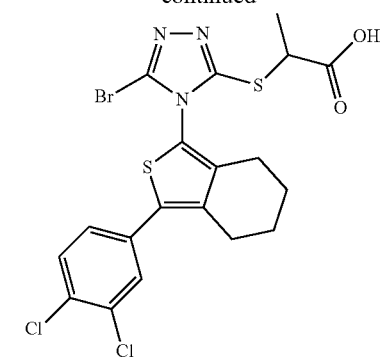
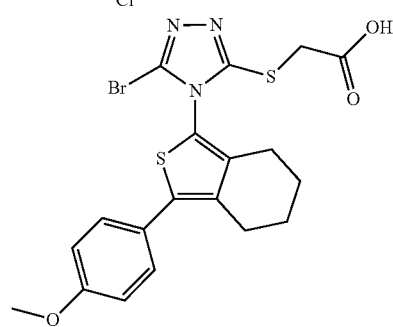
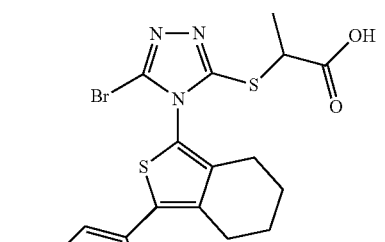
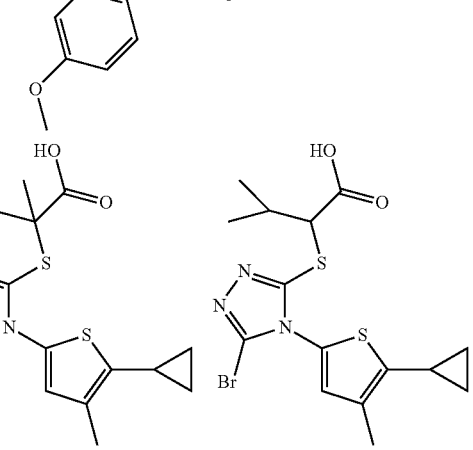
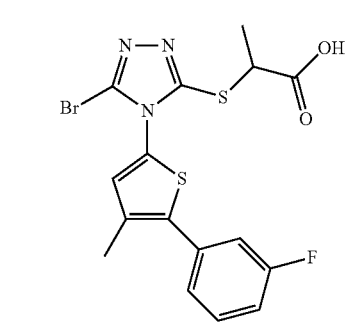
-continued
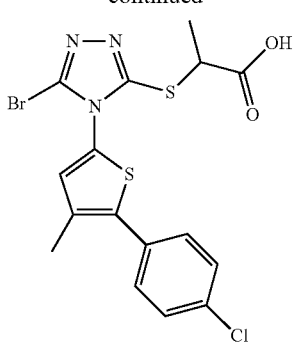
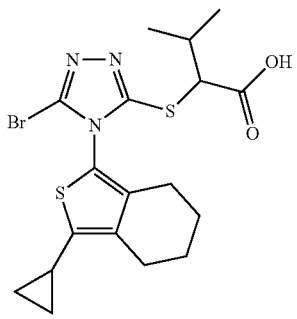
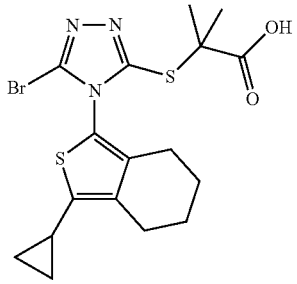
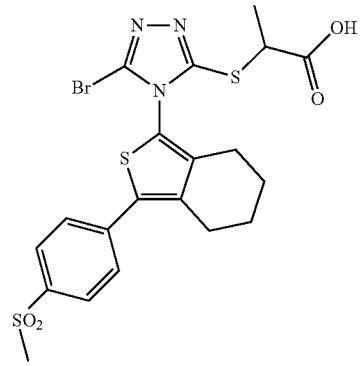
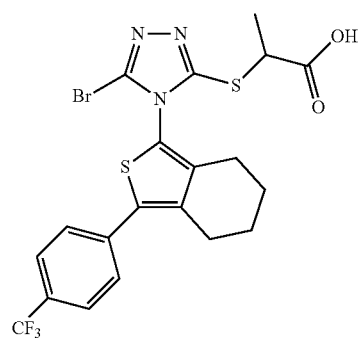

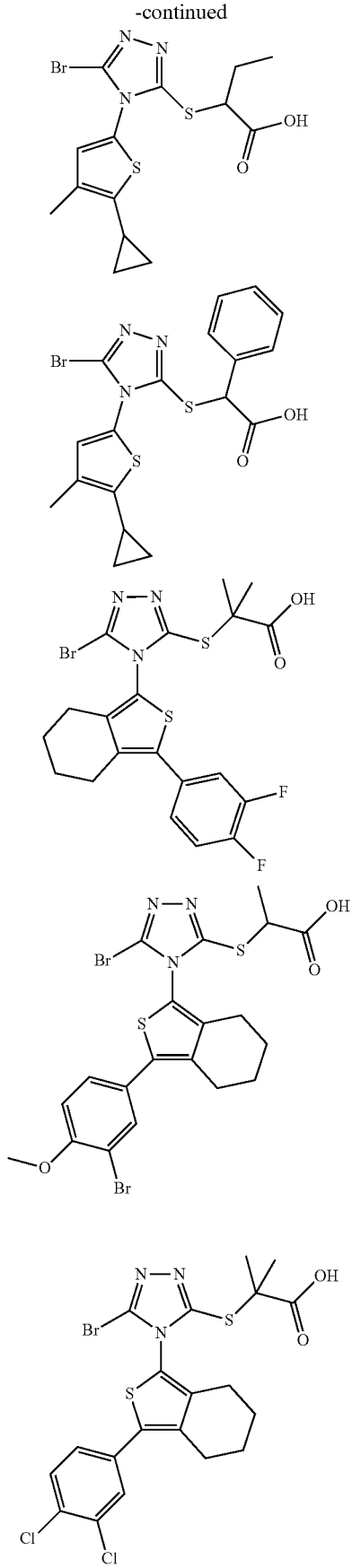
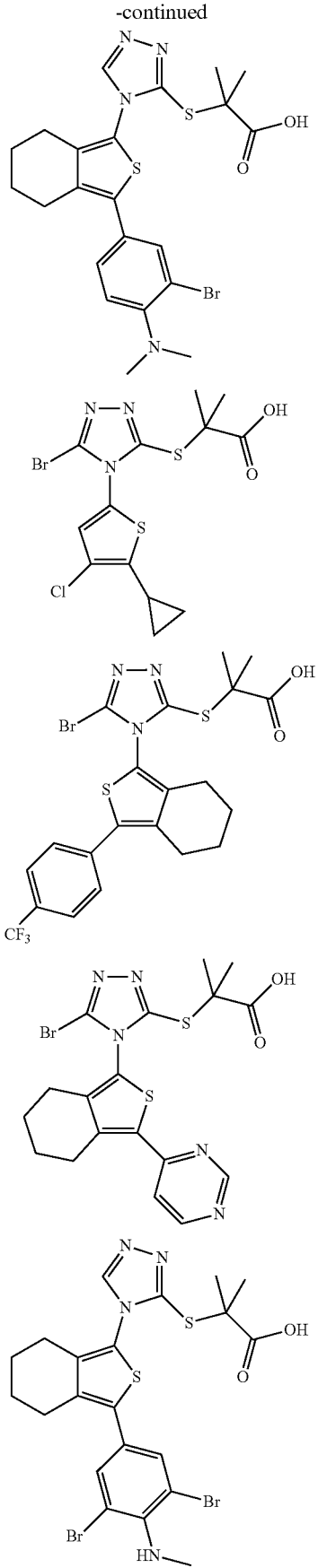

-continued
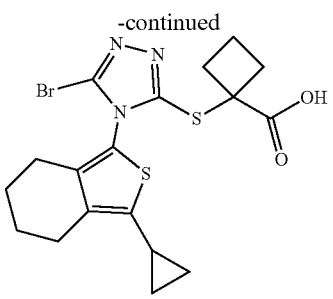
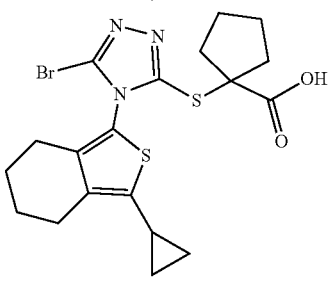
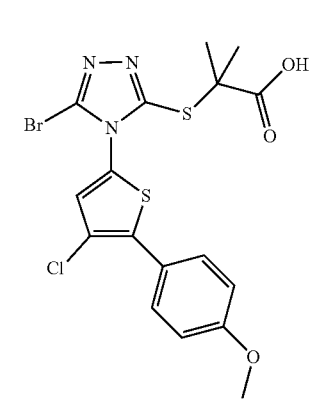
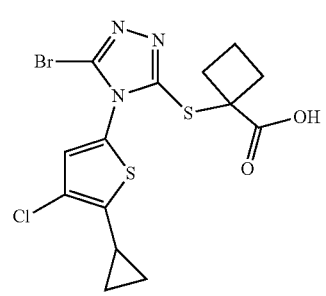
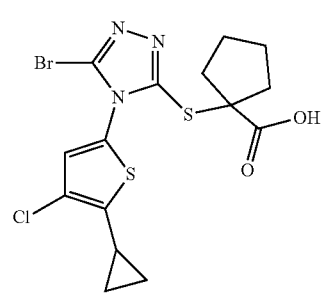
-continued
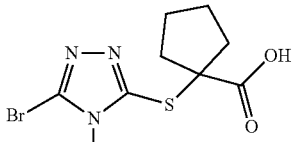
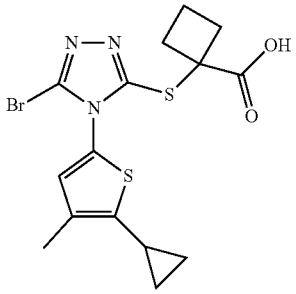
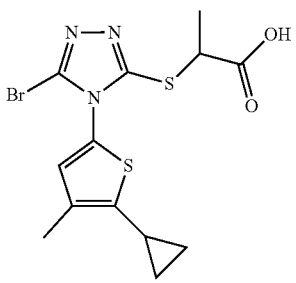 [SMILES: Cc1cc(-n2c(Br)nnc2SC(C)C(=O)O)sc1C1CC1]
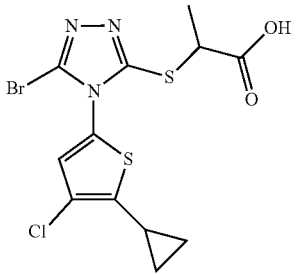
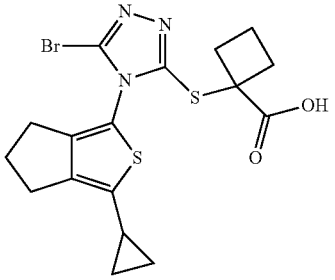
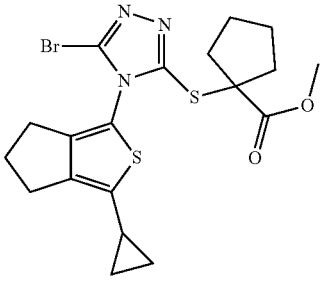

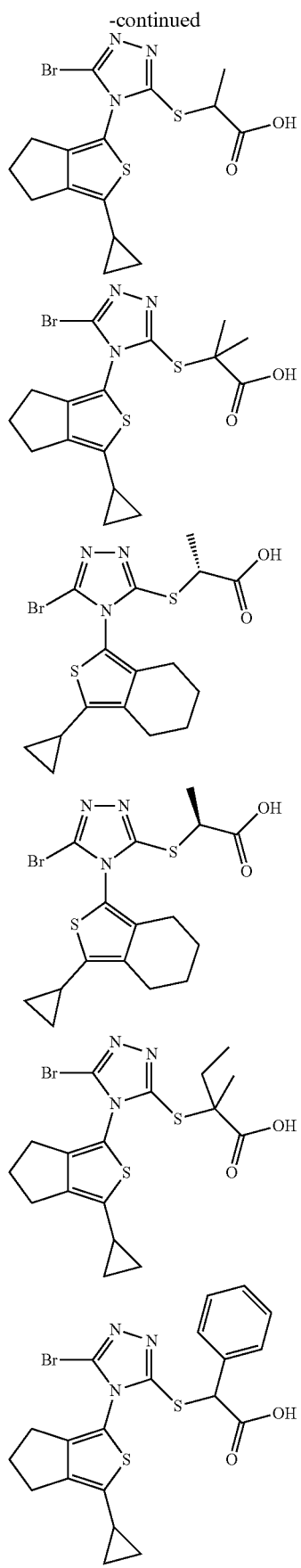
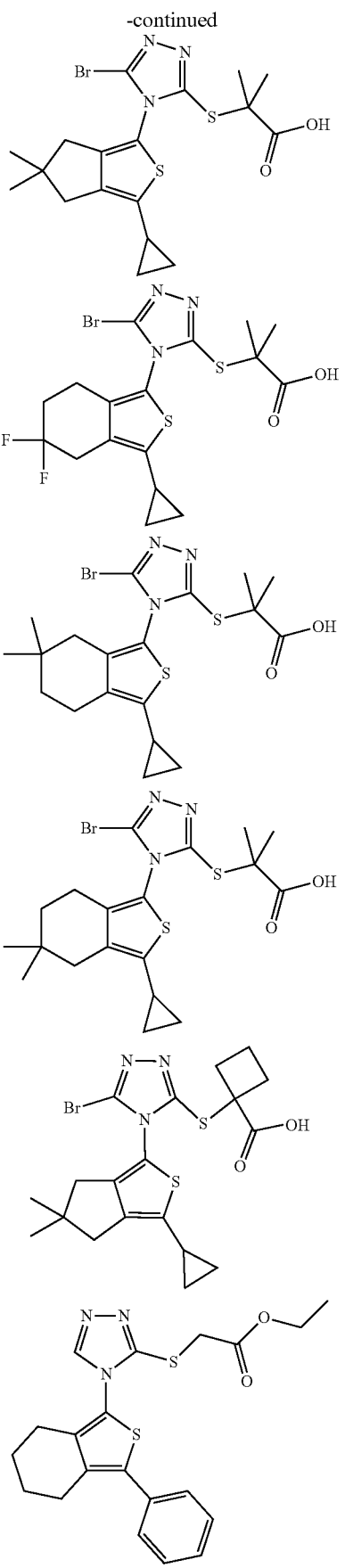

-continued
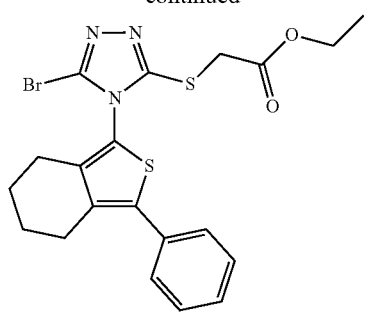
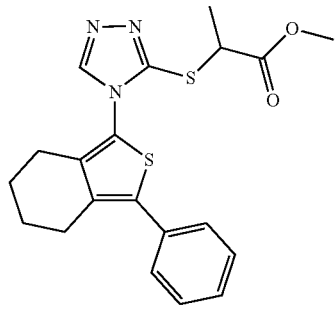
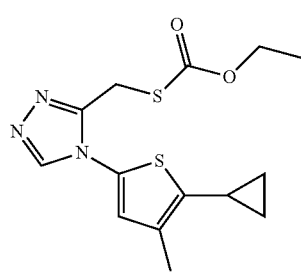
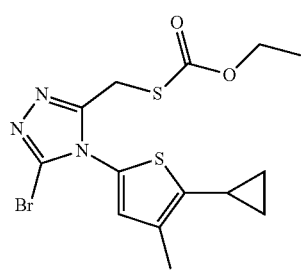
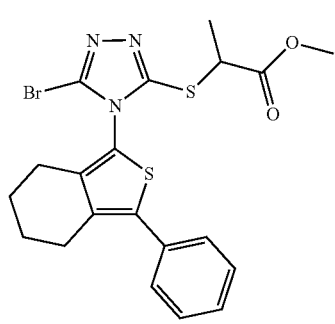
-continued
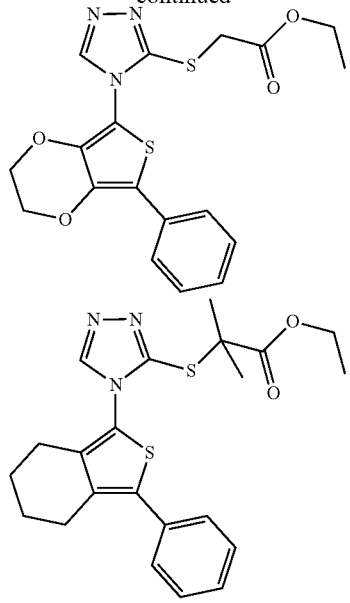
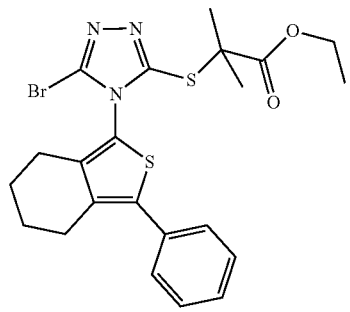
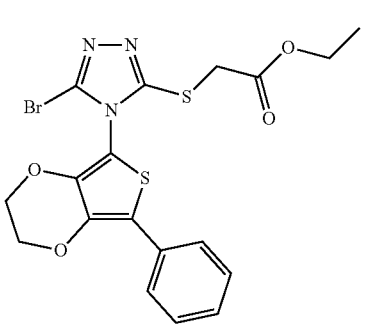
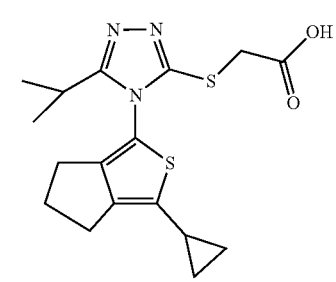

37
-continued
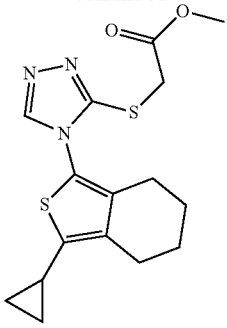
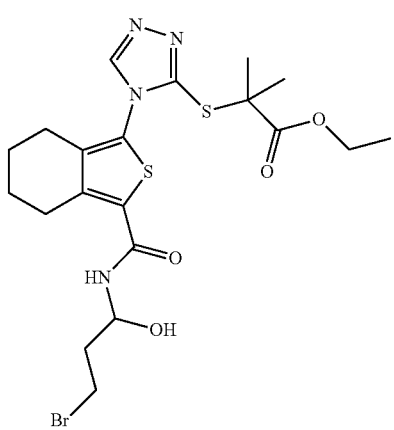
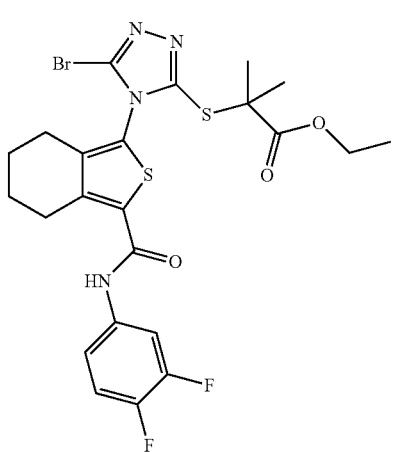
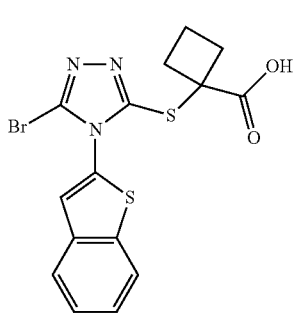
38
-continued
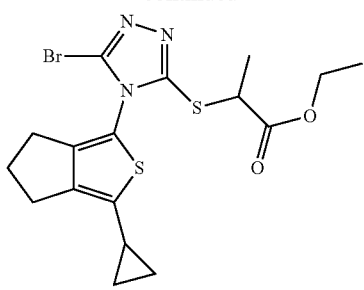
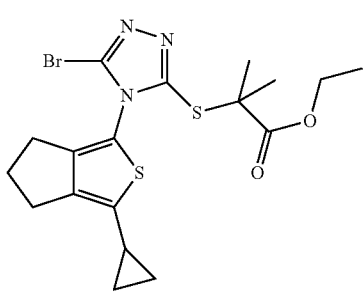
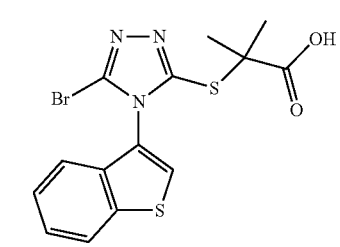
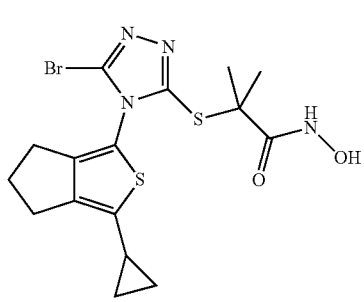
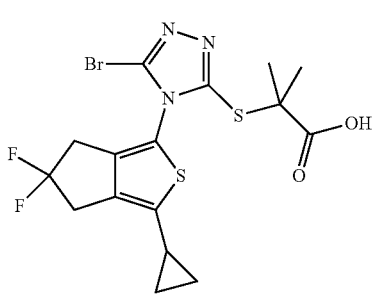

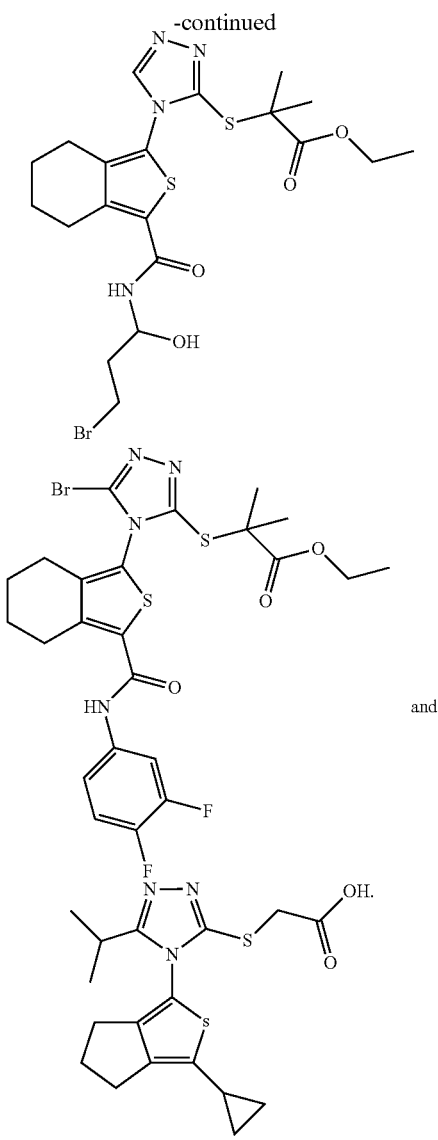

and

Definitions and Explanations

Unless otherwise stated, the terms and phrases used here have the meanings assigned thereto. One certain terms or phrases shouldn't be deemed as being uncertain or unclear without special definition, but should be understood according to normal meanings. Trade names used here refer to corresponding goods or their effective components. The term "pharmaceutically acceptable" used herein is in allusion to those compounds, materials, compositions and/or dosages which are applied to contact to human and animal tissues without excessive toxicity, irritation, anaphylaxis, or other issues or complication, and suit to rational interest and risk ratio within the bounds of reliable medical judgment.

The term "pharmaceutically acceptable salt" refers to salt of the compounds in this invention which are prepared by compounds with certain substituents and relatively nontoxic acids or alkalis. When compounds contain relatively acidic functional group, alkalis-additive salts are prepared by enough alkalis contacting with these compounds in neutral form in pure solutions or appropriate inertia solvents. Pharmaceutically acceptable alkalis-additive salts include sodium, potassium, calcium, ammonium or magnesium salts, or analogous salts. When compounds contain relatively alkaline functional group, acid-additive salts are prepared by enough acids contacting with these compounds in neutral form in pure solutions or appropriate inertia solvents. Examples of pharmaceutically acceptable acid-additive salts include inorganic acid salts, the aforesaid inorganic acids include hydrochloric acid, hydrobromic acid, nitric acid, carbonic acid, bicarbonate radical, phosphoric acid, monohydrogen phosphate, dihydrogen phosphate, sulphuric acid, bisulfate, hydroiodic acid, phosphorous acid and so on; and organic acid, the aforesaid organic acids include acetic acid, propionic acid, isobutyric acid, maleic acid, malonic acid, benzoic acid, succinic acid, octandioic acid, Fumaric acid, lactate, amygdalic acid, alizaric acid, benzenesulfonic acid, p-methylbenzenesulfonic acid, citric acid, tartaric acid, methylsulforic acid and so on; also include amino acid (like arginine) salts, and organic acid salts like glucuronic acid and so on (refer to Berge et al., "pharmaceutical Salts", Journal of pharmaceutical Science 66: 1-19 (1977)). The certain compounds containing alkaline and acidic functional groups in this invention can be transferred into any one of alkaline- or acidic-additive salts.

Preferably, salts contact with alkalis or acids in normal ways, and then maternal compounds are separated to give regenerated compounds in neutral form. The differences between maternal forms and various saline forms of compounds are certain physical properties, such as different solubility in polar solvents.

The term "pharmaceutically acceptable salts" used herein is derivatives of compounds in this invention, including, maternal compounds modified through salifying with acids or alkalis. Examples of pharmaceutically acceptable salts include, but are not limited to, alkali bases, such as inorganic acid salts or organic acid salts of amines, acid radicals, such as alkali metal salts or organic salts of carboxylic acids, and so on. Pharmaceutically acceptable salts include normal nontoxic salts or quaternary ammonium salts of maternal compounds, such as nontoxic salts formed from inorganic or organic acids. Normal nontoxic salts include, but are not limited to, those salts derived from inorganic or organic acids, and the aforesaid inorganic or organic acids are selected from 2-acetoxy benzoic acid, 2-hydroxyl ethanesulfonic acid, acetic acid, ascorbic acid, benzenesulfonic acid, benzoic acid, bicarbonate radical, carbonic acid, citric acid, edetic acid, ethanedisulfonic acid, ethanesulfonic acid, fumaric acid, glucoheptonic acid, gluconic acid, glutamic acid, glycolic acid, hydrobromic acid, hydrochloric acid, hydriodate, hydroxyl, hydroxy naphthalene, hydroxyethyl sulfonic acid, lactic acid, lactose, dodecyl sulfonic acid, maleic acid, malic acid, mandelic acid, methanesulfonic acid, nitric acid, oxalic acid, dihydroxy naphthalene acid, pantothenic acid, phenylacetic acid, phosphoric acid, polygalactose aldehyde, propionic acid, salicylic acid, stearic acid, subacetic acid, succinic acid, sulfamic acid, sulfanilic acid, sulfuric acid, tannin, tartaric acid and p-methylbenzenesulfonic acid.

Pharmaceutically acceptable salts in this invention can be synthesized through conventional chemical methods with maternal compounds containing acid radical or alkaline base. In general, the preparation methods of these salts is that in water or organic solvents or the mixture of both, dissociated acidic or alkaline forms of these compounds react with stoichiometric proper acids or alkalis to give salts. In general, preferably, ether, ethyl acetate, ethanol, isopropanol or acetonitrile, and the like non-aqueous media.

Including forms of salts, compounds provided in this invention also exist forms of prodrugs. Prodrugs of compounds described herein are transferred into compounds in this invention easily through chemical reaction in physiological conditions. Besides, prodrugs can be transferred into compounds in this invention easily through chemical or biochemical methods in vivo environment.

Certain compounds in this invention can exist in non-solvent or solvent forms, including hydrate forms. In general, solvent forms are comparable to non-solvent forms, which are included in this invention.

Certain compounds in this invention can contain the asymmetric carbon (optical center) or double bond. Racemic mixtures, asymmetric isomers, geometric isomers, and single isomers are all included in this invention.

The diagram method of racemates, ambiscalemic and scalemic or enantiomer pure compounds comes from Machr, J. Chem. Ed. 1985, 62: 114-120. 1985, 62: 114-120. Unless otherwise stated, the wedge key and dashed key represent a stereocentric absolute configuration. When the aforesaid compounds in this article contain olefinic double bonds or other geometric asymmetry centers, unless otherwise stated, they include E, Z geometrical isomers. Similarly, all the tautomeric forms are included in this invention.

The compounds in this invention can exist specific geometrical or stereo isomer forms. This invention conceives all this kind compounds, which include cis- and trans-isomers, (−)- and (+)-enantiomers, (R)- and (S)-enantiomers, diastereomers, (D)-isomers, (L)-isomers, their racemic mixtures and other mixtures, such as the mixture rich in symmetric isomers and diastereomers, and all these mixtures are included in this invention. Substituents such as alkyl may exist other asymmetric carbon. And all these isomers and their mixture are included in this invention.

The optically active (R)- and (S)-enantiomers, and (D)- and (L)-isomers can be prepared through chiral synthesis, or chiral reagents or other conventional techniques. If a kind of enantiomers is needed in this invention, they can be prepared through asymmetric synthesis or derivatization of chiral auxiliary, where obtained mixtures of diastereomers are separated and then auxiliary groups are ruptured to give pure needed enantiomers. Or, when compounds contain alkaline groups (such as amino) or acidic groups (such as carboxyl), they form salts of diastereomers with appropriate optically active acids or alkalis which are splitted through conventional methods known in this field to give pure enantiomers. Besides, the separate of enantiomers and diastereomers is through chromatography, and the aforesaid chromatography uses chiral stationary phases, and combines with chemical derivatization optionally (such as amine forming carbamate).

Compounds in this invention can contain unnatural ratio atomic isotopes in one or multi-atoms forming compounds. For example, compounds can be labeled with radioactive isotopes, such as tritium ($^3H$), iodine-125 ($^{125}I$) or carbon-14 ($^{14}C$). The conversion of all the isotopes constituting compounds in this invention, whether radioactivity or not, are included in this invention.

The term "pharmaceutically acceptable carrier" means any preparation or supported media that can deliver effective amount of active substance in this invention, don't interfere biological active of active substance and is nontoxic to hosts or patients, and representative carriers include water, oil, vegetable and mineral, cream base, lotion base, ointment base and so on. These bases include suspending agent, tackifier and penetration enhancer and so on. Their preparations are known to technicians in cosmetic and topical medication fields.

The term "excipient" usually means carrier, diluent and/or media which are needed for preparation of effective pharmaceutical compositions.

In allusion to medicine or pharmacological activator, the term "effective amount" or "therapeutically effective amount" means enough amount of medicine or agent which can achieve the desired affect without toxin. For the oral preparation in this invention, "effective amount" of a kind of active substance in compositions means the amount needed to achieve the desired affect when combining with another active substance in compositions. The effective amount varies with each individual, and depends on ages of receptors and general situations, also specific active substances. In individual cases, appropriate effective amount can be determined according to routine tests by technicians in this field.

The term "active constituent", "therapeutic agents", "active substance" or "active agent" mean a kind of chemical entities which treat targeted disorders, diseases or symptoms.

The term "substituted", as used herein, means that any one or more hydrogens on the designated atom is replaced with a selection from the indicated group, including deuterium "D" atom, a variant hydrogen, provided that the designated atom's normal valency is not exceeded, and that the substitution results in a stable compound. When a substituent is keto (i.e., =O), then two hydrogens on the atom are replaced. Keto substituents are not present on aromatic moieties. The term "optionally substituted", as used herein, means that the designated atom can be substituted or unsubstituted by the substituents, and unless otherwise stated, the species and numbers of the substituents are not defined provided that they can be achieved in Chemistry.

When any variable (e.g. R) occurs more than one time in any constituents or formula for a compound, its definition at each occurrence is independent of its definition at every other occurrence. Thus, for example, if a group is shown to be substituted with 0-2 R, then said group may optionally be substituted with up to two R groups and R at each occurrence is selected independently from the definition of R. Also, combinations of substituents and/or variables are permissible only if such combinations result in stable compounds.

When the number of a bonding group is zero, for example, —(CRR)$_0$—, then this bonding group is a single bond.

When one of variants is selected from single bond, then two groups bonding by this variant is bonded directly, for example, when "L" in "A-L-Z" represents a single bond, this formula is "A-Z" actually.

When a substituent is vacant, then this substituent doesn't exist, for example, when "X" in "A-X" is vacant, this formula is "A" actually.

When a bond to a substituent is shows to cross a bond connecting more than one atoms in a ring, then such substituent may be bonded to any atom on the ring. For example, structural units

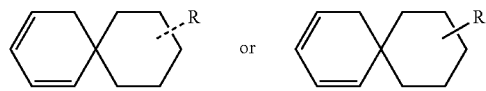

mean any site of cyclohexyl or cyclohexadiene can be substituted. When a substituent is listed without indicating the atom via which such substituent is bonded to the rest of compound of a given formula, then such substituent may be bonded via any atom in such substituent. For example, pyridyl can be connected to the group substituted as a substituent through any carbon atom on the pyridyl. When a bonded group is listed without indicating the connecting direction, the connecting direction is arbitrary. For example, connecting bond L in

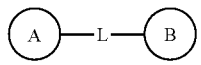

is -M-W—, then -M-W— can be regarded as

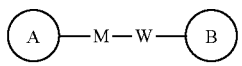

connected by ring A and ring B which is read from left to right, or -M-W— can be regarded as

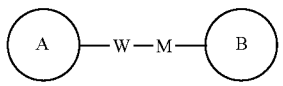

connected by ring A and ring B which is read from right to left. Combinations of substituents and/or variables are permissible only if such combinations result in stable compounds.

The term "hetero", mean, unless otherwise stated, "heteroatom" or "heteroadical" (namely radical containing heteroatom), including atoms other than carbon (C) and hydrogen (H), also including the radicals containing these aforesaid heteroatoms. Examples include oxygen (O), nitrogen (N), sulfur (S), silicon (Si), germanium (Ge), aluminum (Al), and boron (B), also include optically substituted —C(=O)N(H)—, —N(H)—, —C(=NH)—, —S(=O)$_2$N(H)—, or —S(=O)N(H)—.

"Ring" as used herein, means a substituted or unsubstituted cycloalkyl, hetero-cyclalkyl, cycloalkenyl, hetero-cycloalkenyl, cycloalkynyl, hetero-cycloalkybyl, aryl, or heteroaryl. A ring includes mono, bi, sprio, fused, and bridged ring moieties. The number of atoms in a ring is typically defined by the number of the members in the ring. For example, a "5- to 7-membered ring", means there are 5 to 7 atoms in the encircling arrangement. Unless otherwise specified, the ring optically includes one to three heteroatoms. Thus, the term "5- to 7-membered ring" includes, for example, phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heterocycle" or "heterocyclic group" is intended to mean a stable monocyclic, bicyclic, or tricyclic ring containing heteroatom or heteroradical, which is saturated, partially saturated or unsaturated (aromatic), and which consists of carbon atoms and 1, 2, 3, or 4 ring heteroatoms independently selected from the groups consisting of N, O and S and including any bicyclic groups in which any of the above-defined heterocyclic rings is fused to a benzene ring. The nitrogen and sulfur heteroatoms may optically be oxidized (i.e. NO and S(O) p, p is 1 or 2). The nitrogen atom may be substituted or unsubstituted (i.e. N or NR wherein R is H or another substituent, if define). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not more than 1. As used herein, the term "aromatic heterocyclic group" or "heteroaryl" is tended to mean a stable 5, 6, or 7-membered monocyclic or bicyclic or 7, 8, 9 or 10-membered bicyclic heterocyclic aromatic ring which consists of carbon atoms and 1, 2, 3 or 4 heteroatoms independently selected from the group consisting of N, O and S. The nitrogen atom may be substituted or unsubstituted (o.e. N or NR wherein R is H or another substituent, if defined). The nitrogen and sulfur heteroatoms may optionally be oxidized (i.e., NO and S(O) p, p is 1 or 2). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen, two nitrogen atoms, and a carbon-nitrogen group. It is noted that a bridge always converts a monocyclic ring into a tricyclic ring. When a ring is bridged, the substituents recited for the ring may also be present on the bridge.

Example of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, dihydrobenzofuran, chromenyl, decahydroquinolinyl, 2H,6H-1,5-2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indoliziny, indolyl, 3H-indolyl, isobenzofuranyl, isoindolinyl, isoindolyl, isoquinolinyl, isothiazolyl, isoxazolyl, methylenedioxyphenyl, morpholiny, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxyindolyl, pyrimidinyl, phenanthridinyl, phenanthrolinyl, phenazinyl, phenothiazinyl, benzodiazepinyl, phenoloxazinyl phthalazinyl, piperazinyl, piperidinyl, piperidonyl, 4-piperidonyl, piperonyl, pteridinyl, purinyl, pyranyl, pyrazinyl, pyrazolidinyl, pyrodazinyl, pyrazolyl, pyridazinyl, pyridooxazole, pyridoimidazole, pyridothiazole, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroidoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthiophenyl, thienooxazolyl, thienothiazolyl, thienoimidazole, thienyl, triazinyl, 1,2,3-triazolyl, 1,2,4-triazolyl, 1,2,5-triazolyl, 1,3,4-triazolyl, and xanthenyl. Also included are fused ring and spiro compounds.

The term "hydrocarbyl" or it lower concept (such as alkyl, alkenyl, alkynyl and phenyl etc.) by itself or as part of another substituent, means, unless otherwise stated, a straight or branched chain, or cyclic hydrocarbon radical, or combination thereof, which may be fully saturated (such as alkyl), unitary or polyunsaturated (such as alkenyl, alkynyl, phenyl), may be mono-substituted, di-substituted, or poly-substituted, and may be monovalent (such as methyl), divalent (such as methylene), or polyvalent (such as methine), may include divalent or polyvalent radicals, and have a specified number of carbon atoms (e.g., $C_1$-$C_{12}$ represents 1 to 12 carbons, $C_1$-$C_{12}$ are selected from the group of $C_1$, $C_2$, $C_3$, $C_4$, $C_5$, $C_6$, $C_7$, $C_8$, $C_9$, $C_{10}$, $C_{11}$ and $C_{12}$; $C_{3-12}$ selected from the group of $C_3$, $C_4$, $C_5$, $C_6$, $C_7$, $C_8$, $C_9$, $C_{10}$, $C_{11}$ and $C_{12}$). "hydrocarbyl" include, but are not limited to, aliphatic hydrocarbyl and aromatic hydrocarbyl, and the aliphatic hydrocarbyl include linear and cyclic ones, specifically including but not limited to, alkyl, alkenyl, and alkynyl, and the aromatic hydrocarbyl includes, but is not limited to, 6-12 membered aromatic hydrocarbyl, for example, benzene, and naphthalene. In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, isobutyl, cyclohexyl, (cyclohexyl)methyl, cyclopropylmethyl, homologs and isomers of, for example, n-pentyl, n-hexyl, n-octyl, and the like. An unsaturated alkyl group is one having one or more double bonds or triple bonds. Examples of unsaturated alkyl groups include, but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "heterohydrocarbyl" or its lower concept (such as heteroalkyl, heteroalkeneyl, heteroalkynyl and heteroaryl etc.) by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl", by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein the nitrogen and sulfur atoms may optionally be oxidized and the nitrogen heteroatom may optionally be quaternized. The heteroatom or heteroatom group may be located at any internal position of the heterohydrocarbyl (including the position where the hydrocarbyl is attached to the rest of the molecule), but term "alkoxy", "alkylamino", "alkylsulfur" (thioxyl) are idiomatic expressions which means those alkyl groups are attached to the remainder of molecule through a O, NH or S. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$.

The term "cyclohydrocarbyl", "heterocyclohydrocarbyl", or their lower concept (such as aryl, heteroaryl, cycloalkyl, heterocycloalkyl, cycloalkenyl, heterocycloalkenyl, cycloalkynyl, and heterocycloalkynyl etc.) by themselves or in combination with other terms mean cyclized hydrocarbyl and heterohydrocarbyl, respectively. Additionally, for heterohydrocarbyl or heterocyclohydrocarbyl (such as heteroalkyl and heterocycloalkyl), a heteroatom can occupy the position at which the heterocycle is attached to the remainder of the molecule. Example of cycloalkyl include, but are not limited to, cyclopentyl, cyclohexyl, 1-cyclohexenyl, 3-cyclohexenyl, cycloheptyl, and the like. Non-limiting examples of heterocycloalkyl moieties include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl and 2-piperazinyl.

Unless otherwise stated, the terms "alkyl" means linear or branched saturated hydrocarbyl, which may be mono-substituted (such as —$CH_2F$) or poly-substituted (such as —$CF_3$), and may be monovalent (such as methyl), divalent (such as methylene), or polyvalent (such as methine). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl), etc.

Unless otherwise stated, the terms "alkenyl" means an alkyl having one or more carbon-carbon double bonds at any position of the chain, which may be mono-substituted, di-substituted, or poly-substituted, and may be monovalent, divalent, or polyvalent. Examples of alkenyl include vinyl, propenyl, butenyl, pentenyl, hexenyl, butadienyl, piperylene, hexadienyl, etc.

Unless otherwise specified, the term "alkynyl" means an alkyl having one or more carbon-carbon triple bonds at any position of the chain, which may be mono-substituted, di-substituted, or poly-substituted, and may be monovalent, divalent, or polyvalent. Examples of alkynyl include ethynyl, propynyl, butynyl, pentynyl, etc.

Unless otherwise stated, the cycloalkyl includes any stable cyclic or polycyclic hydrocarbon group, and any carbon atom is saturated, which may be mono-substituted or poly-substituted, and may be monovalent, divalent, or polyvalent. Examples of cycloalkyl include, but are not limited to, cyclopropyl, norbornyl, [2.2.2]bicyclooctane, [4.4.0]bicyclononane, etc.

Unless otherwise stated, the cycloalkenyl includes any stable cyclic or polycyclic hydrocarbon group containing one or more unsaturated carbon-carbon double bonds at any position of the ring, which may be mono-substituted or poly-substituted, and may be monovalent, divalent, or polyvalent. Examples of cycloalkenyl include, but are not limited to, cyclopentenyl, cyclohexenyl, etc.

Unless otherwise stated, the cycloalkynyl includes any stable cyclic or polycyclic hydrocarbon group containing one or more unsaturated carbon-carbon triple bonds at any position of the ring, which may be mono-substituted or poly-substituted, and may be monovalent, divalent, or polyvalent.

Unless otherwise stated, the term "halo" or "halogen" by itself or as part of another substituent denotes a fluorine, chlorine, bromine, or iodine atom. In addition, the term "haloalkyl" is meant to include monohaloalkyl and polyhaloalkyl. For example, the term "halo($C_1$-$C_4$)alkyl" is meant to include but not limited to trifluoromethyl, 2,2,2-trifluoroethyl, 4-chlorobutyl, 3-bromopropyl, and the like. Unless otherwise stated, examples of haloalkyl include, but are not limited to, trifluoromethyl, trichloromethyl, pentafluoroethyl, and pentachloroethyl.

"Alkoxy" represents the above alkyl having a specified number of carbon atoms attached through an oxygen bridge, and unless otherwise specified, $C_{1-6}$ alkoxy includes alkoxy of $C_1$, $C_2$, $C_3$, $C_4$, $C_5$ and $C_6$. Examples of alkoxy include, but are not limited to, methoxy, ethoxy, n-propoxy, isopropoxy, n-butoxy, sec-butoxy, tert-butoxy, n-pentyloxy and S-pentyloxy. Unless otherwise stated, the term "aryl" refers to a polyunsaturated aromatic hydrocarbon substituent, which may be mono- or poly-substituted, and may be monovalent, divalent, or polyvalent, and may be monocyclic or polycyclic rings (such as 1 to 3 rings; at least one of which is aromatic), being fused together or covalently linked. The term "heteroaryl" refers to an aryl group (or ring) containing one to four heteroatoms. In one illustrative example, the heteroatom is selected from the group consisting of B, N, O, and S, wherein the nitrogen and sulfur atoms are optionally oxidized and the nitrogen atom is optionally quaternized. A heteroaryl can be attached to the rest of the molecule through a heteroatom. Non-limiting examples of aryl or heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolinyl, 5-isoquinolinyl, 2-quinoxalinyl, 5-quinoxalinyl, 3-quinolinyl, and 6-quinolinyl. The substituents for any of the above aryl and heteroaryl ring systems are selected from the acceptable substituents described below.

Unless otherwise stated, the term "aryl" when used in combination with other terms (e.g., aryloxy, arylthio, aralkyl) includes both aryl and heteroaryl rings as defined above. Thus, the term "aralkyl" is meant to include those radicals in which an aryl group is attached to an alkyl group (e.g., benzyl, phenethyl, pyridylmethyl and the like) including those alkyl group in which a carbon atom (e.g., a methylene group) has been replaced by, for example, an oxygen atom, for examples, phenoxymethyl, 2-pyridyloxymethyl, 3-(1-naphthyloxy)propyl, and the like.

The term "leaving group" means a functional group or atom which can be displaced by another functional group or atom in a substitution reaction (such as a nucleophilic substitution reaction). By way of example, representative leaving groups include triflate: chloro, bromo and iodo group; sulfobic ester groups: such as mesylate, tosylate, brosylate, nosylate and the like; and acyloxy groups, such as acetoxy, trifluoroacetoxy and the like.

The term "protecting group" includes but is not limited to "amino-protecting group", "hydroxyl-protecting group" and "thiol-protecting group". The term "amino-protecting group" means a protecting group suitable for preventing undesired reactions at an amino nitrogen. Representative amino-protecting groups include, but are not limited to, formyl; acyl group, for example alkanoyl groups, such as acetyl, trichloroacetul or trifluoroacetyl; alkoxycarbonyl groups, such as tert-butoxycarbonyl (Boc); arylmethoxycarbonyl groups, such as benzyloxycarbobyl (Cbz) and 9-fluorenylmethoxycarbonyl (Fmoc); arylmethyl groups, such as benzyl (Bn), trityl (Tr), and 1,1-di-(4'-methoxyphenyl) methyl; silyl groups, such as trimethylsilyl (TMS) and tert-butylsimethylsilyl (TBS); and the like. The term "hydroxyl-protecting group" means a protecting group suitable for preventing undesired reactions at a hydroxyl group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyl (TMS) and tert-butylsimethylsilyl (TBS); and the like.

The compounds of this invention can be prepared in a number of ways known to one skilled in the art of organic synthesis. The examples of this invention can be synthesized using the methods described below, together with synthetic methods known in the art of synthetic organic chemistry, or by variations thereon as appreciated by those skilled in the art. Concrete methods include, but are not limited to, those describe below.

All solvents used are commercially available. This present invention adopts following abbreviating words: aq means aqueous; HATU means 2-(7-Azabenzotriazol-1-yl)-N,N,N',N'-tetramethyluroniumhexafluorophosphate; EDC means N-(3-Dimethylaminopropyl)-N'-ethylcarbodiimide hydrochloride; m-CPBA means 3-chloroperoxybenzoic acid; eq means equivalent; CDI means carbonyldiimidazole; DCM means dichloromethane; PE means petroleum ether; DIAD means diisopropyl azodiformate; DMF means N,N-dimethylformamide; DMSO means dimethyl sulfoxide; EtOAc means ethyl acetate; EtOH means ethanol; MeOH means methanol; CBz means carbobenzyloxy, a kind of protecting group for amine; BOC means t-butyloxy carbonyl, a kind of protecting group for amine; HOAc means acetic acid; NaCNBH$_3$ means sodium cyanoborohydride; r.t. means room temperature; O/N means overnight; THF means tetrahydrofuran; Boc$_2$O means di-tert-butyl dicarbonate; TFA means atrifluoroacetic acid; DIPEA means ethyldiisopropylamine; SOCl$_2$ means thionyl chloride; CS$_2$ means carbon disulfide; TsOH means p-toluenesulfonic acid; NFSI means N-Fluorobenzenesulfonimide; NCS means N-Chlorosuccinimide; n-Bu$_4$NF means tetrabutylammonium fluoride; iPrOH means 2-propanol; mp means melting point; LDA means lithium diisopropylamide.

Compounds are named either manually or by using ChemDraw®, or using vendors catalogue name if commercially available.

Technical Effect

Compared to lesinurad, the compound of the present invention demonstrated more significant inhibitory activity in vitro for $^{14}$C uric acid transportation mediated by URAT1 on HEK293 cell line stably transfected with the URAT1(uric acid transporter) gene.

DETAILED DESCRIPTION OF THE PREFERRED EMBODIMENT

The present invention will be specifically described below by way of embodiments, but the scope of the present invention is not limited thereto. The present invention has been described in detail and the embodiments are disclosed as well, any modification of the embodiment without departing from the spirit of the present invention should be considered obviousness.

Reference Embodiment 1: Fragment BB-1

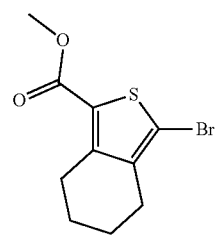

Synthetic Route:

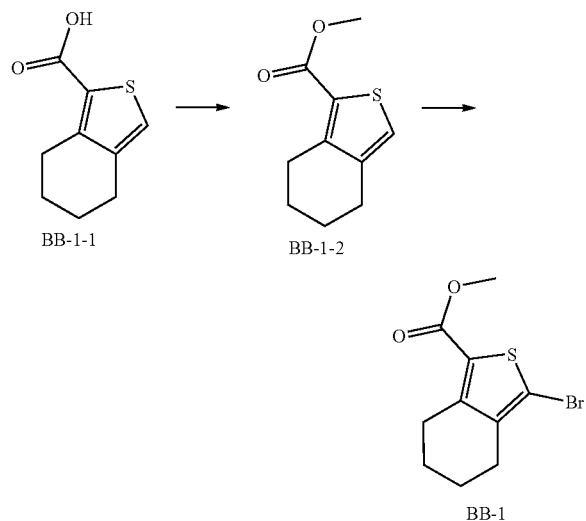

Step 1: Synthesis of Compound BB-1-2

To a solution of compound BB-1-1 (50.00 mg, 274.36 umol, 1.00 eq) in methanol (5.00 mL) was added concentrated sulfuric acid (1.84 g, 18.76 mmol, 1.00 mL, 68.38 eq), and then the reaction mixture was refluxed for 16 h in an oil bath of 80° C. After the reaction was finished, the mixture was cooled to 15° C., and then extracted with PE (3 mL×7). The organic phases were combined, dried over anhydrous Na$_2$SO$_4$, the drier was filtered out and the filtrate was concentrated to give compound BB-1-2 as colorless clear liquid (51.20 mg, 260.87 umol, crude product). Nuclear magnetism as follow: $^1$H NMR (400 MHz, CDCl$_3$) δ: 7.08 (s, 1H), 3.85 (s, 3H), 3.04 (m, 2H), 2.71 (m, 2H), 1.80-1.71 (m, 4H).

Step 2: Synthesis of Compound BB-1

To a solution of compound BB-1-2 (50.00 mg, 254.75 umol, 1.00 eq) in acetic acid (5.00 mL) was added liquid bromine (48.85 mg, 305.70 umol, 15.76 uL, 1.20 eq), and the reaction mixture was reacted for 2 h at 20° C. After the reaction was finished, the mixture was concentrated to remove liquid bromine and acetic acid to give compound BB-1 as yellow solid (70.10 mg, 254.76 umol, 100.00% yield). Solid nuclear magnetism as follow: $^1$H NMR (400 MHz, CDCl$_3$) δ: 3.86 (s, 3H), 3.03 (m, 2H), 2.56 (m, 2H), 1.82-1.70 (m, 4H).

Reference Embodiment 2: Fragment BB-2

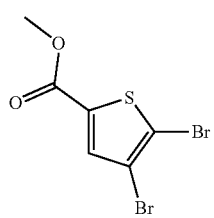

Synthetic Route:

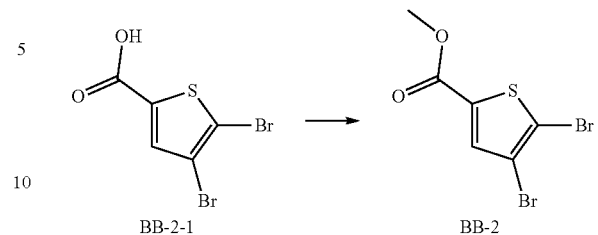

Step 1: Synthesis of Compound BB-2

To a solution of compound BB-2-1 (5.0 g, 17.49 mmol) in methanol (20 mL) was added concentrated sulfuric acid (3.00 mL) slowly, and then the reaction mixture was warmed to 80° C. and stirred for 12 h. After the reaction was finished, the mixture was cooled to room temperature and concentrated under reduced pressure to remove solvent, and the residue was added into water (50 mL) and extracted with EtOAc (100 mL×3). The organic phases were combined and washed with sat.aq NaCl (20 mL), dried over anhydrous Na$_2$SO$_4$, the drier was filtered out and the filtrate was concentrated under reduced pressure. The residue was purified by flash column chromatography eluted with EtOAc/PE (2-10%) to give compound BB-2 (4.8 g, 16.00 mmol, 91.49% yield) as white solid. $^1$H NMR (400 MHz, CDCl$_3$) δ: 7.59 (s, 1H), 3.89 (s, 3H).

Reference Embodiment 3: Fragment BB-3

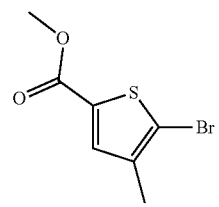

Synthetic Route:

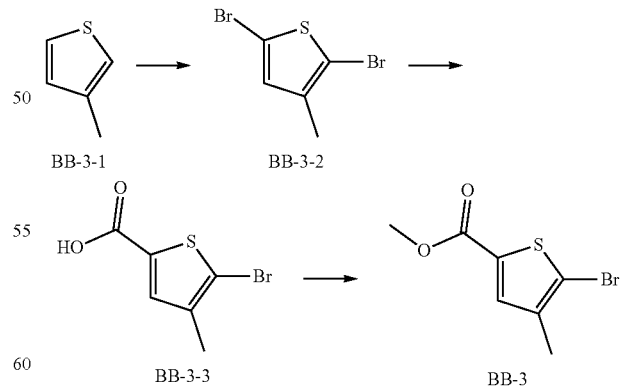

Step 1: Synthesis of Compound BB-3-2

To a solution of 3-methylthiophene BB-3-1 (25.00 g, 254.66 mmol, 1.00 eq) in acetic acid (250 mL) was added N-bromosuccinimide (113.31 g, 636.65 mmol, 2.50 eq) at room temperature and then was stirred for 3 h at room temperature. After the reaction was finished, the mixture was concentrated under reduced pressure to remove solvent, and the residue was added water (100 mL) and extracted with EtOAc (100 mL×3). The organic phases were combined and washed sequentially with water (100 mL) and sat.aq NaCl (20 mL), dried over anhydrous $Na_2SO_4$, the drier was filtered out and the filtrate was concentrated under reduced pressure to give compound BB-3-2 (50.00 g, 195.34 mmol, 76.71% yield) as yellow oil which could be used for next step without further purification. $^1$H NMR (400 MHz, DMSO-$d_6$) δ: 2.12 (s, 3H) 7.12 (s, 1H).

Step 2: Synthesis of Compound BB-3-3

To a solution of compound BB-3-2 (27.00 g, 105.49 mmol, 1.00 Eq) in THF (400 mL) was added n-BuLi (46.4 mL, 2.5 M, 116.03 mmol, 1.10 Eq) in n-hexane at −78° C., and after addition, the mixture was stirred for further 1 h at −78° C. The excess dry carbon dioxide was bubbled into the mixture until the reaction was finished (about 3 h). The reaction system was quenched with water (100 mL), adjusted pH to 3-4 with 1 M hydrochloric acid solution and lots of brown solid was precipitated. The solid was filtered and the filter cake was washed with methyl tert-butyl ether (100 mL) and dried in vacuo to give compound BB-3-3 (16.00 g, 72.38 mmol, 68.61% yield) as brown solid. $^1$H NMR (400 MHz, DMSO-$d_6$) δ: 2.17 (s, 3H) 7.54 (s, 1H).

Step 3: Synthesis of Compound BB-3

To a solution of compound BB-3-3 (6.80 g, 30.76 mmol, 1.00 Eq) in methanol (100 mL) was added concentrated sulfuric acid (6.03 g, 61.52 mmol, 2.00 Eq) dropwise, and then the reaction mixture was stirred for 12 h at 80° C. After the reaction was finished, the mixture was concentrated under reduced pressure to remove solvent, and the residue was added into water (40 mL) and extracted with EtOAc (50 mL×2). The organic phases were combined and washed sequentially with water (30 mL) and sat.aq NaCl (30 mL), dried over anhydrous $Na_2SO_4$, the drier was filtered out and the filtrate was concentrated under reduced pressure to give the compound as yellow oil. The yellow oil was purified by flash column chromatography eluted with EtOAc/PE (5-10%) to give compound BB-3 (7.00 g, 29.77 mmol, 96.78% yield) as yellow solid. $^1$H NMR (400 MHz, CDCl$_3$) δ: 2.22 (s, 3H) 3.88 (s, 3H) 7.49 (s, 1H).

Reference Embodiment 4: Fragment BB-4

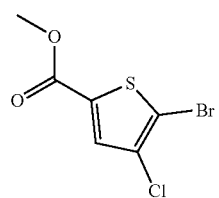

Synthetic Route:

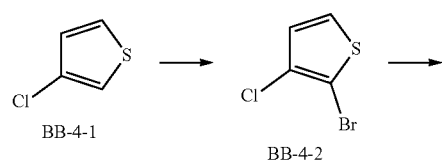

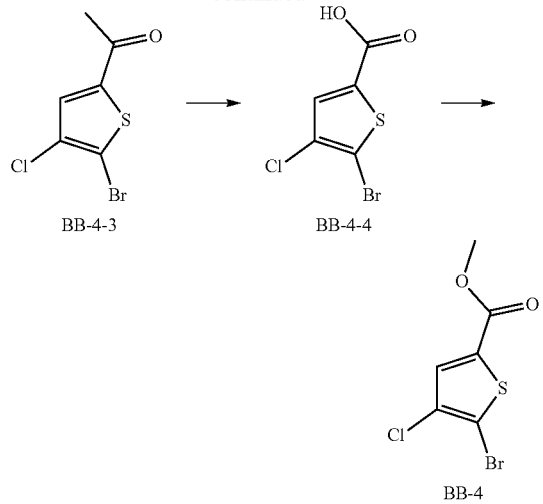

Step 1: Synthesis of Compound BB-4-2

3-chlorothiophene BB-4-1 (50.00 g, 421.66 mmol, 1.00 eq) was solved in CHCl$_3$ (200.00 mL) and acetic acid (200.00 mL), and the mixture was added N-bromosuccinimide (75.05 g, 421.66 mmol, 1.00 eq). The reaction mixture was stirred for 30 min at 20° C., warmed to 100° C. and refluxed for 2 h, and the mixture turned to brown clarified liquid from yellow muddy. Then the mixture was poured into water (200 mL) and extracted with DCM (150 mL×3). The DCM phases were combined, washed with sat.aq Na$_2$CO$_3$ (150 mL) and then with sat.aq NaCl (100 mL), dried over anhydrous Na$_2$SO$_4$, the drier was filtered out and the filtrate was concentrated under reduced pressure to remove solvents and give crude product, compound BB-4-2 (80.00 g, 405.10 mmol, 96.07% yield) as yellow oil which could be used for next step without further purification. $^1$H NMR (400 MHz, CDCl$_3$) δ: 7.28 (d, J=2.0 Hz, 1H), 6.89 (d, J=2.0 Hz, 1H).

Step 2: Synthesis of Compound BB-4-3

To a solution of compound BB-4-2 (80.00 g, 405.10 mmol, 1.00 eq) and acetyl chloride (47.70 g, 607.65 mmol, 1.50 eq) in anhydrous DCM (500.00 mL) was added anhydrous aluminium chloride (64.82 g, 486.12 mmol, 1.20 eq) in batches and then the reaction mixture was stirred for 12 h at 15° C. After TLC detected that the reaction was finished, the mixture was poured into ice-water (500 mL) and extracted with DCM (200 mL×2). The organic phases were combined, dried over anhydrous Na$_2$SO$_4$, the drier was filtered out and the solution was concentrated under reduced pressure to remove solvents and give product BB-4-3 (90.00 g, 375.75 mmol, 92.76% yield) as offwhite solid which could be used for next step without further purification. $^1$H NMR (400 MHz, DMSO-$d_6$) δ: 8.07 (s, 1H), 2.53 (s, 3H).

Step 3: Synthesis of Compound BB-4-4

To a solution of NaOH (327.66 g, 4.10 mol, 10.90 eq) in water (500.00 mL) was cooled to 0° C. while stirring and then the mixture was added liquid bromine (198.16 g, 1.24 mol, 3.30 eq) dropwise, following added compound BB-4-3 (90.00 g, 375.75 mmol, 1.00 eq) in dioxane (500.00 mL) dropwise. The reaction mixture was stirred for 15 h at 15° C., and then was cooled to 0° C., adjusted pH to 2-3 with concentrated hydrochloric acid and extracted with EtOAc (300 mL×3). The organic phases were combined and dried over moderate anhydrous Na$_2$SO$_4$, the drier was filtered out and the solution was concentrated under reduced pressure to remove solvents and give beige solid. The beige solid was slurried with PE (300 mL), and then the mixture was filtered and the filter cake was dried in vacuo to give product BB-4-4 (65.00 g, 269.16 mmol, 71.63% yield) as faint yellow solid. $^1$H NMR (400 MHz, DMSO-d$_6$) δ: 7.72 (s, 1H).

Step 4: Synthesis of Compound BB-4

To a solution of compound BB-4-4 (40.00 g, 165.64 mmol, 1.00 eq) in methanol (300.00 mL) was added concentrated sulfuric acid (1.62 g, 16.56 mmol, 0.10 eq) dropwise while stirring. And then the reaction mixture was heated to 100° C. and reacted for 15 h. The reaction mixture was concentrated under reduced pressure to remove solvents and the residue was added water (150 mL). The mixture was stirred to disperse product and then filtered, the filter cake was dried to give product BB-4 (38.00 g, 148.72 mmol, 89.78% yield) as khaki solid. $^1$H-NMR (400 MHz, DMSO-d$_6$) δ: 7.84 (s, 1H), 3.89-3.81 (m, 3H).

Reference Embodiment 5-9: Fragment BB-5-BB-9

Reference embodiments listed in table below were synthesized according to step 1-2 in reference embodiments 1

| Reference embodiment | BB | Structure | NMR & MS |
|---|---|---|---|
| Reference embodiment 5 | BB-5 | 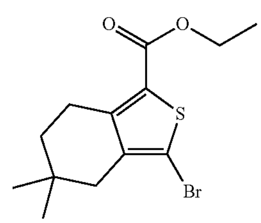 [SMILES: CCOC(=O)c1sc(Br)c2c1CCC(C)(C)C2] | $^1$H NMR (400 MHz, CDCl$_3$) δ: 4.28 (q, J = 7.2 Hz, 2H), 3.03 (t, J = 6.8 Hz, 2H), 2.30 (s, 2H), 1.59-1.46 (m, 2H), 1.36 (t, J = 7.2 Hz, 3H), 0.99 (s, 6H). |
| Reference embodiment 6 | BB-6 | 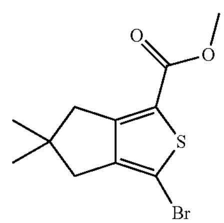 | $^1$H NMR (400 MHz, CDCL$_3$) δ: 3.75 (s, 3H), 2.74 (s, 2H), 2.35 (s, 2H), 1.11 (s, 6H). MS m/z: 288.9, 290.8 |
| Referenece emboiment 7 | BB-7 | 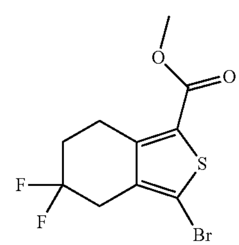 [SMILES: COC(=O)c1sc(Br)c2c1CCC(F)(F)C2] | $^1$H NMR: (400 MHz, CDCl$_3$) δ: 3.78 (s, 3H), 3.19 (t, J = 7.2 Hz, 2H), 2.96 (t, J = 14.4 Hz, 2H), 2.18-2.08 (m, 2H). MS m/z: 310.8, 312.9 |
| Reference embodiment 8 | BB-8 | 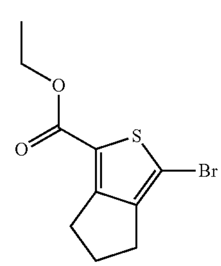 | $^1$H NMR (400 MHz, CDCl$_3$) δ: 4.31 (q, J = 7.2 Hz, 2H), 3.01 (t, J = 7.2 Hz, 2H), 2.65-2.58 (m, 2H), 2.43 (q, J = 7.2 Hz, 2H), 1.36 (t, J = 7.2 Hz, 3H). MS m/z: 274.8, 276.9 |
| Reference embodiment 9 | BB-9 | 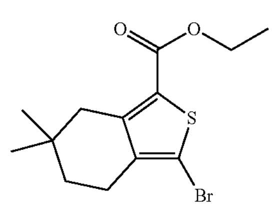 [SMILES: CCOC(=O)c1sc(Br)c2c1CC(C)(C)CC2] | $^1$H NMR (400 MHz, CDCl$_3$) δ: 4.30 (q, J = 7.2 Hz, 2H), 2.81 (s, 2H), 2.56 (t, J = 6.8 Hz, 2H), 1.59-1.54 (m, 2H), 1.36 (t, J = 7.2 Hz, 3H), 0.99 (s, 6H). MS m/z: 317.0, 318.9 |

| Reference embodiment | BB | Structure | NMR & MS |
|---|---|---|---|
| Reference embodiment 10 | BB-10 | 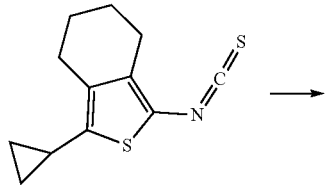 | $^1$H NMR (400 MHz, DMSO-$d_6$): δ: 4.41-4.31 (m, 4H), 3.87 (s, 3H) |
Embodiment 1: WX001, WX001A, WX001B
Synthetic Route:
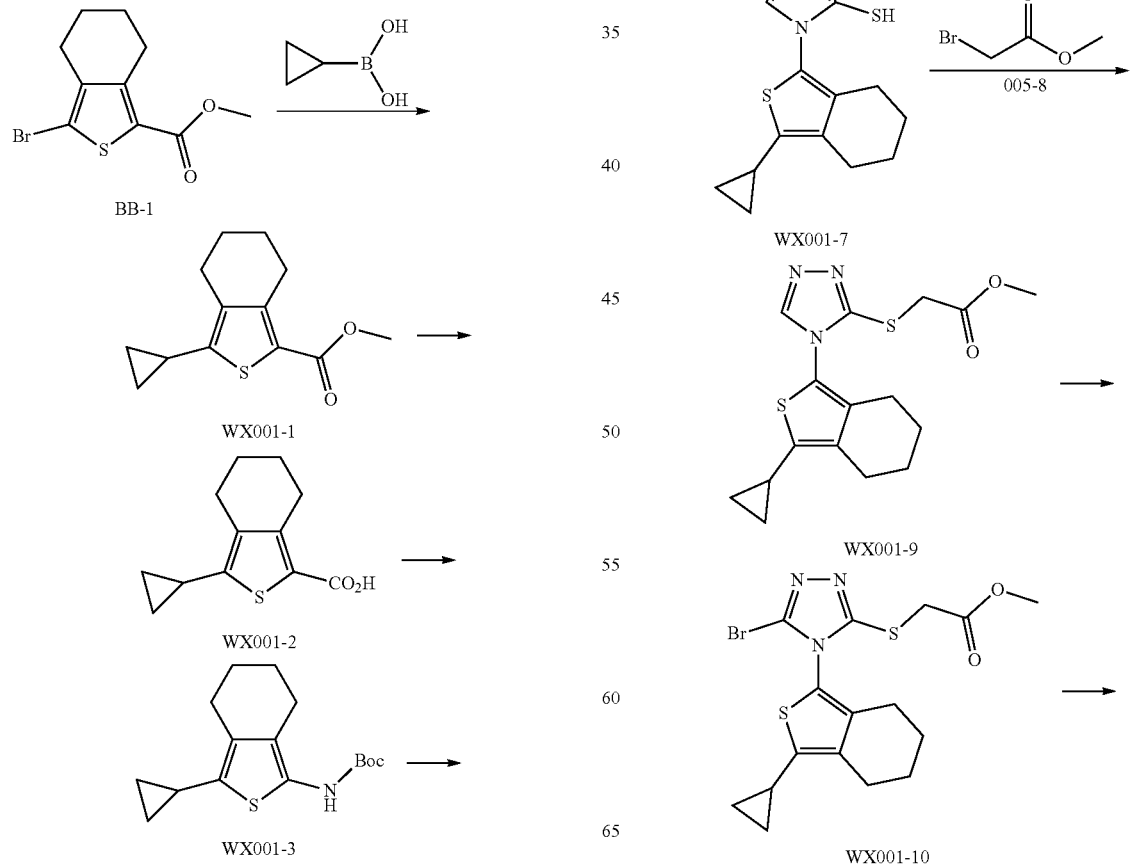

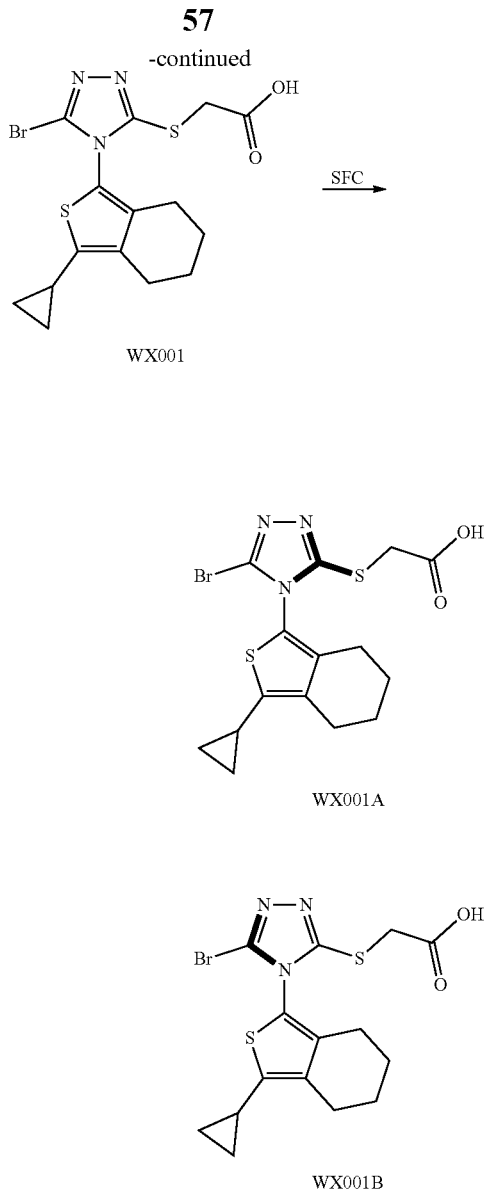

WX001

WX001A

WX001B

Step 1: Synthesis of Compound WX001-1

To a solution of compound BB-1 (5.00 g, 18.17 mmol), cyclopropylboronic acid (2.03 g, 23.62 mmol), tricyclohexyl-phosphine (1.53 g, 5.45 mmol) and tripotassium phosphate (13.89 g, 65.41 mmol) in toluene (60 mL) and water (3 mL) was added palladium acetate (407.93 mg, 1.82 mmol), and then was heated to 80-100° C. under $N_2$ and stirred overnight. After the reaction was finished, the mixture was cooled to room temperature, filtered and the filter cake was washed with EtOAc (10 mL). The filtrate was concentrated to dry under reduced pressure. The residue was purified by flash column chromatography eluted with EtOAc/PE(0-20%) to give target compound WX001-1 (brown oil, 3.20 g, 74.5% yield). $^1$H NMR (400 MHz, CDCl$_3$) δ: 3.82 (s, 3H), 3.03-3.01 (m, 2H), 2.70-2.68 (m, 2H), 1.98-1.78 (m, 1H), 1.78-1.76 (m, 4H), 1.08-1.04 (m, 2H), 0.77-0.75 (m, 2H).

Step 2: Synthesis of Compound WX001-2

The solution of compound WX001-1 (3.20 g, 13.54 mmol) and NaOH (1.08 g, 27.08 mmol) in methanol (40 mL) and water (40 mL) was heated to 70-80° C. and stirred overnight. After the reaction was finished, the reaction mixture was concentrated under reduced pressure to remove solvent. The residue was dissolved in water (50 mL), adjusted pH to 3-4 with dilute hydrochloric acid (1 M), and white solid was precipitated. Then the mixture was extracted with EtOAc (150 mL×3). The three organic phases were combined and dried over anhydrous Na$_2$SO$_4$, the drier was filtered out and the filtrate was concentrated under reduced pressure to remove solvents and give target compound WX001-2 (white solid, 3.00 g, 99.67% yield). $^1$H NMR (400 MHz, DMSO-d$_6$) δ: 2.89-2.88 (m, 2H), 2.64-2.63 (m, 2H), 2.06-2.03 (m, 1H), 1.73-1.62 (m, 4H), 1.07-1.02 (m, 2H), 0.66-0.63 (m, 2H).

Step 3: Synthesis of Compound WX001-3

The solution of compound WX001-2 (3.00 g, 13.50 mmol), diphenylphosphoryl azide (5.57 g, 20.25 mmol) and trimethylamine (4.10 g, 40.50 mmol) in t-butanol (50 mL) was heated to 80-100° C. under $N_2$ and stirred overnight. After the reaction was finished, the reaction mixture was concentrated under reduced pressure to remove solvent. The oily residue was purified by flash column chromatography eluted with EtOAc/PE (0-20%) to give target compound WX001-3 (green solid, 2.50 g, 63.11% yield). $^1$H NMR (400 MHz, CDCl$_3$) δ: 6.29 (brs, 1H), 2.68-2.60 (m, 2H), 2.49-2.36 (m, 2H), 1.87-1.84 (m, 1H), 1.82-1.57 (m, 4H), 1.50 (s, 9H), 0.90-0.86 (m, 2H), 0.66-0.73 (m, 2H).

Step 4: Synthesis of Compound WX001-4

To a solution of compound WX001-3 in EtOAc (20.0 mL) was added HCl in EtOAc (4 M, 40.0 mL) and the reaction mixture was stirred for 2 h at room temperature. After the reaction was finished, the reaction mixture was concentrated under reduced pressure to remove solvents and give compound WX001-4 (brown solid, 1.90 g, 97.06% yield) which could be used for next step without further purification. MS-ESI m/z: 193.9 [M+H]$^+$.

Step 5: Synthesis of Compound WX001-6

To a solution of compound WX001-4 (690.00 mg, 3.00 mmol) in DCM (20.00 mL) was added isopropyl ethyl amine (1.16 g, 9.01 mmol), and the mixture was cooled to 0° C. in ice bath and then added compound WX001-5 (517.93 mg, 4.50 mmol) and stirred for 15 min at 0° C. After the reaction was finished, the mixture was warmed to room temperature, quenched with dilute hydrochloric acid (1 M, 5 mL). The organic phase was separated, dried over anhydrous Na$_2$SO$_4$, the drier was filtered out and the filtrate was concentrated under reduced pressure to remove solvents and the residue was targeted compound WX001-6 (brown oil, 700 mg, 99.13% yield) which could be used for next step without further purification.

Step 6: Synthesis of Compound WX001-7

The solution of compound WX001-6 (700.00 mg, 2.97 mmol) and hydrazine hydrate (446.64 mg, 8.92 mmol) in DMF (10.00 mL) was heated to 80-100° C. and stirred for 2 h, and then was added N,N-dimethylformamidedimethylacetal (49.99 mg, 2.38 mmol). The reaction mixture was stirred at 80-100° C. overnight. After the reaction was finished, the mixture was cooled to room temperature, and poured into water (5 mL) and extracted with EtOAc (10 mL×2). The two organic phases were combined, dried over anhydrous Na$_2$SO$_4$, the drier was filtered out and the filtrate was concentrated under reduced pressure to remove solvents. The residue was purified by flash column chromatography eluted with EtOAc/PE (0-50%) to give targeted compound WX001-7 (orange oil, 90.00 mg, 10.92% yield). MS-ESI m/z: 277.9 [M+H]$^+$.

Step 7: Synthesis of Compound WX001-9

The solution of compound WX001-7 (10.00 mg, 36.05 umol), methyl bromoacetate WX001-8 (6.62 mg, 39.65 umol) and potassium carbonate (5.48 mg, 39.65 umol) in DMF (3.00 mL) was stirred overnight at room temperature. After the reaction was finished, the mixture was concentrated under reduced pressure to remove solvent. The residue was separated by prep-HPLC to give targeted compound WX001-9 (transesterification methyl ester product compound) (5.00 mg, 38.16% yield). $^1$H NMR (400 MHz, CDCl$_3$) δ: 8.15 (s, 1H), 4.12 (s, 1H), 3.77 (s, 3H), 2.72-2.69 (m, 2H), 2.38-2.37 (m, 2H), 1.98-1.94 (m, 1H), 1.79-1.67 (m, 4H), 1.04-1.01 (m, 2H), 0.71-0.67 (m, 2H). MS-ESI m/z: 349.9 [M+H]$^+$.

Step 8: Synthesis of Compound WX001-10

To a solution of compound WX001-9 (25.00 mg, 68.78 umol) in acetonitrile (5.00 mL) was added pyridine (6.53 mg, 82.54 umol) at room temperature, the mixture was cooled to 0° C. in ice bath and then was added liquid bromine (32.98 mg, 206.34 umol) dropwise, and the reaction mixture was stirred for 5 h at 20° C. After the reaction mixture was warmed to room temperature, the mixture was quenched with sat.aq sodium bisulfite (1 mL) and concentrated under reduced pressure to remove solvents. The residue was purified by flash column chromatography eluted with EtOAc/PE (0%-75%) to give targeted compound WX001-10 (colorless oil, 10.00 mg, 32.86% yield). MS-ESI m/z: 442.0 [M+H]$^+$, 444.0 [M+H+2]$^+$.

Step 9: Synthesis of Compound WX001

The solution of compound WX001-10 (10.00 mg, 22.60 umol) in ethanol (1.00 mL), THF (1.00 mL) and water (1.00 mL) was cooled to 0° C. in ice bath and then was added LiOH (649.52 ug, 27.12 umol), and the reaction mixture was stirred for 1 h at 0° C. After the reaction was finished, the mixture was adjusted pH to 3-4 with dilute hydrochloric acid (1 M) at 0° C. and then concentrated under reduced pressure to remove solvents. The residue was separated by prep-HPLC to give targeted compound WX001 (1.40 mg, 14.95% yield). $^1$H NMR (400 MHz, Methanol-d$_4$) δ: 4.12-4.01 (m, 2H), 2.77-2.75 (m, 2H), 2.33-2.09 (m, 2H), 2.07-2.06 (m, 1H), 1.84-1.75 (m, 4H), 1.10-1.08 (m, 2H), 0.73-0.70 (m, 2H). MS-ESI m/z: 413.9 [M+H]$^+$, 415.9 [M+H+2]$^+$.

Step 10: Synthesis of Compound WX001A and WX001B

Compound WX001 was separated by supercritical fluid chromatography to give rotational isomers WX001A and WX001B whose retention time was 4.409 min and 4.599 min, respectively and ratio was 1:1 (separation condition: Column: Chiralpak AD-3 150×4.6 mm I.D., 3 um; Mobile phase: A: CO$_2$ B:ethanol (0.05% DEA); Gradient: from 5% to 40% of B in 5.0 min and hold 40% for 2.5 min, then 5% of B for 2.5 min; Flow rate: 2.5 mL/min; Column temperature: 35° C.; Wavelength: 220 nm).

Embodiment 2: WX002

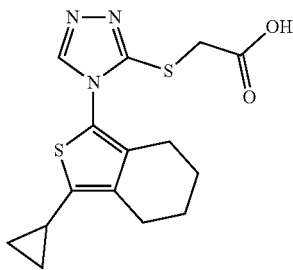 [SMILES: O=C(O)CSc1nncn1-c1sc(C2CC2)c2c1CCCC2]

Synthetic Route:

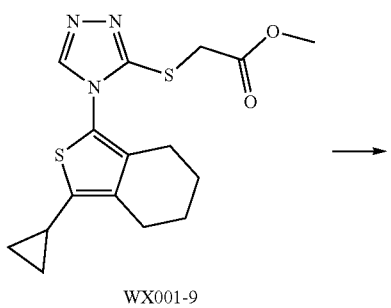

WX001-9

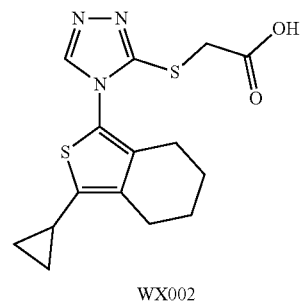

WX002

Step 1: Synthesis of Compound WX002

The solution of compound WX001-9 (14.00 mg, 38.51 umol) in ethanol (1.00 mL), THF (1.00 mL) and water (1.00 mL) was cooled to 0° C. in ice bath and then was added LiOH.H$_2$O (1.11 mg, 46.21 umol), and the reaction mixture was stirred for 30 min at 0° C. After the reaction was finished, the mixture was adjusted pH to 6-7 with dilute hydrochloric acid (1 M) at 0° C. and then concentrated under reduced pressure to remove solvents. The residue was separated by prep-HPLC to give targeted compound WX002 (2.90 mg, 22.45% yield). $^1$H NMR (400 MHz, Methanol-d$_4$) δ: 9.04 (s, 1H) 4.15-4.09 (m, 2H), 2.78-2.75 (m, 2H), 2.46-2.45 (m, 2H), 2.08-2.04 (m, 1H), 1.83-1.75 (m, 4H), 1.09-1.06 (m, 2H), 0.72-0.68 (m, 2H). MS-ESI m/z: 335.9 [M+H]$^+$.

Embodiments listed in table below were synthesized according to step 1-10 in embodiments 1. The structures in the table represent their potential rotational isomers and chiral isomers.

TABLE 1
| Embodiments | Fragment 1 | Structure | Compound |
|---|---|---|---|
| 3 | BB-1 | 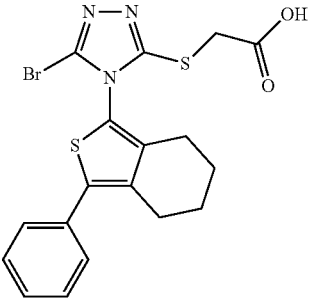 [SMILES: O=C(O)CSc1nnc(Br)n1-c1sc(-c2ccccc2)c2c1CCCC2] | WX003 |
| 4 | BB-1 | 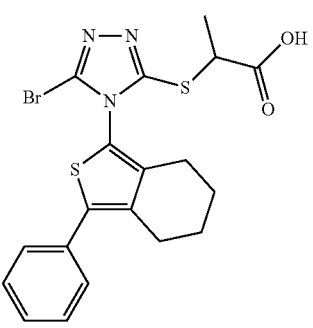 [SMILES: CC(Sc1nnc(Br)n1-c1sc(-c2ccccc2)c2c1CCCC2)C(=O)O] | WX004 |
| 5 | BB-1 | 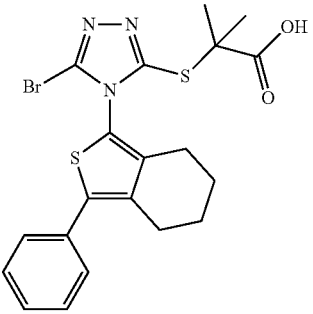 [SMILES: CC(C)(Sc1nnc(Br)n1-c1sc(-c2ccccc2)c2c1CCCC2)C(=O)O] | WX005 |
| 6 | BB-1 | 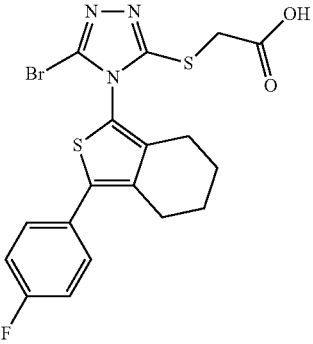 [SMILES: O=C(O)CSc1nnc(Br)n1-c1sc(-c2ccc(F)cc2)c2c1CCCC2] | WX006 |

TABLE 1-continued

| Embodiments | Fragment 1 | Structure | Compound |
|---|---|---|---|
| 7 | BB-1 | 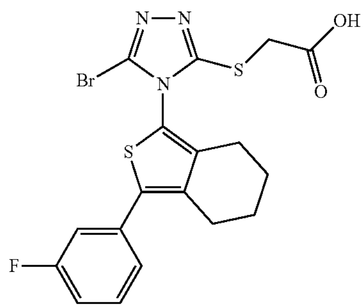 [SMILES: O=C(O)CSc1nnc(Br)n1-c1sc(-c2cccc(F)c2)c2c1CCCC2] | WX007 |
| 8 | BB-1 | 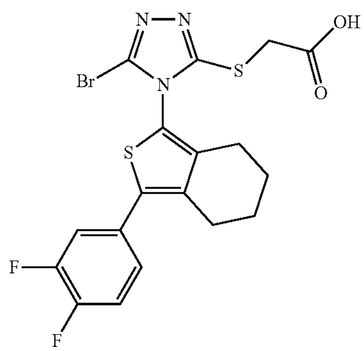 [SMILES: O=C(O)CSc1nnc(Br)n1-c1sc(-c2ccc(F)c(F)c2)c2c1CCCC2] | WX008 |
| 9 | BB-1 | 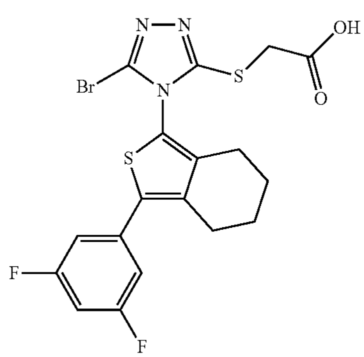 [SMILES: O=C(O)CSc1nnc(Br)n1-c1sc(-c2cc(F)cc(F)c2)c2c1CCCC2] | WX009 |
| 10 | BB-1 | 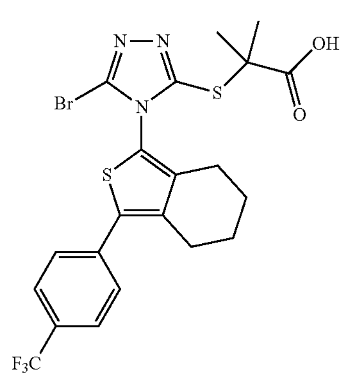 [SMILES: CC(C)(Sc1nnc(Br)n1-c1sc(-c2ccc(C(F)(F)F)cc2)c2c1CCCC2)C(=O)O] | WX010 |

TABLE 1-continued

| Embodiments | Fragment 1 | Structure | Compound |
|---|---|---|---|
| 11 | BB-1 | 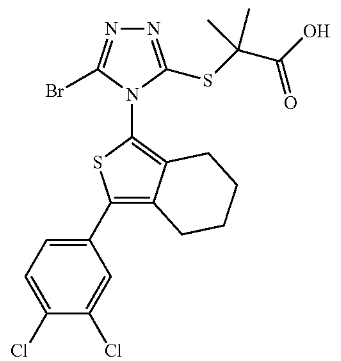 [SMILES: CC(C)(Sc1nnc(Br)n1-c1sc(-c2ccc(Cl)c(Cl)c2)c2c1CCCC2)C(=O)O] | WX011 |
| 12 | BB-1 | 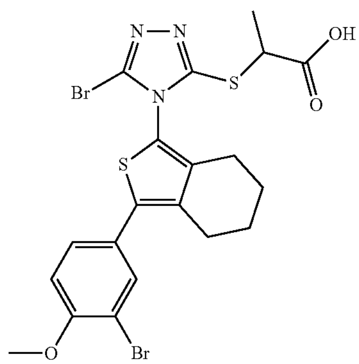 [SMILES: COc1ccc(-c2sc(-n3c(Br)nnc3SC(C)C(=O)O)c3c2CCCC3)cc1Br] | WX012 |
| 13 | BB-1 | 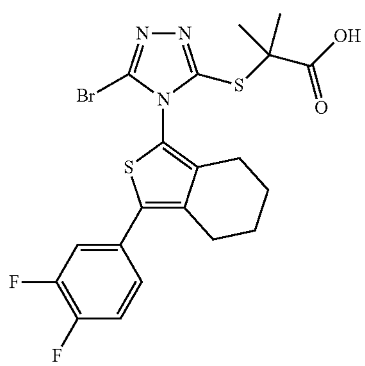 [SMILES: CC(C)(Sc1nnc(Br)n1-c1sc(-c2ccc(F)c(F)c2)c2c1CCCC2)C(=O)O] | WX013 |
| 14 | BB-1 | 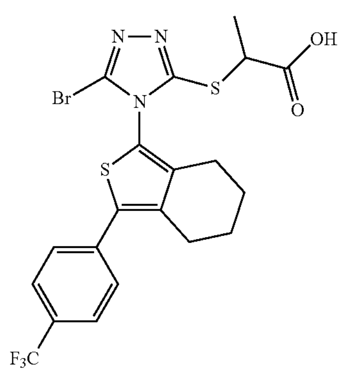 [SMILES: CC(Sc1nnc(Br)n1-c1sc(-c2ccc(C(F)(F)F)cc2)c2c1CCCC2)C(=O)O] | WX014 |

TABLE 1-continued

| Embodiments | Fragment 1 | Structure | Compound |
|---|---|---|---|
| 15 | BB-1 | 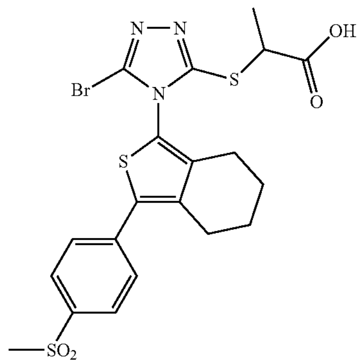 [SMILES: CC(Sc1nnc(Br)n1-c1sc(-c2ccc(S(C)(=O)=O)cc2)c2c1CCCC2)C(=O)O] | WX015 |
| 16 | BB-1 | 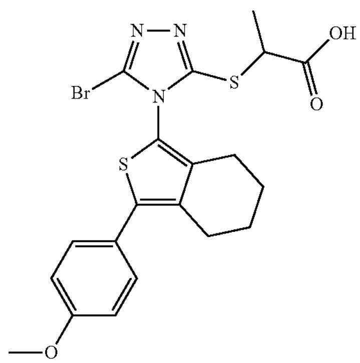 [SMILES: COc1ccc(-c2sc(-n3c(Br)nnc3SC(C)C(=O)O)c3c2CCCC3)cc1] | WX016 |
| 17 | BB-1 | 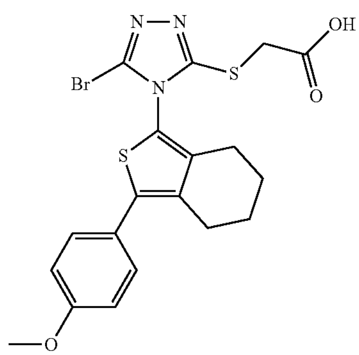 [SMILES: COc1ccc(-c2sc(-n3c(Br)nnc3SCC(=O)O)c3c2CCCC3)cc1] | WX017 |
| 18 | BB-1 | 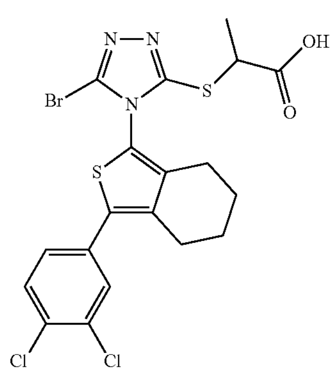 [SMILES: CC(Sc1nnc(Br)n1-c1sc(-c2ccc(Cl)c(Cl)c2)c2c1CCCC2)C(=O)O] | WX018 |

TABLE 1-continued
| Embodiments | Fragment 1 | Structure | Compound |
|---|---|---|---|
| 19 | BB-1 | 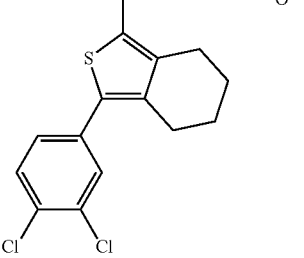 | WX019 |
| 25 | BB-1 | 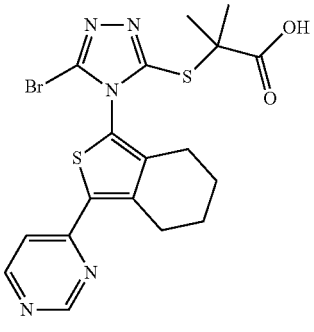 [SMILES: CC(C)(Sc1nnc(Br)n1-c1sc(-c2ccncn2)c2c1CCCC2)C(=O)O] | WX025 |
| 26 | BB-1 | 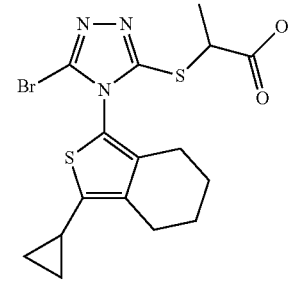 | WX026 |
| 27 | BB-1 | 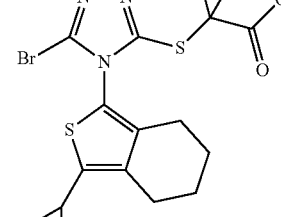 | WX027 |

TABLE 1-continued

| Embodiments | Fragment 1 | Structure | Compound |
|---|---|---|---|
| 28 | BB-1 | 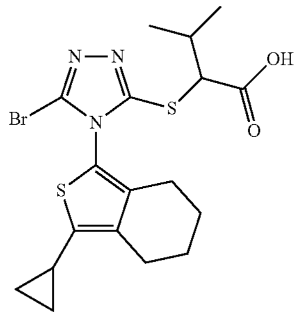 [SMILES: CC(C)C(Sc1nnc(Br)n1-c1sc(C2CC2)c2c1CCCC2)C(=O)O] | WX028 |
| 29 | BB-1 | 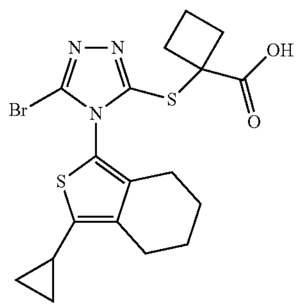 [SMILES: O=C(O)C1(Sc2nnc(Br)n2-c2sc(C3CC3)c3c2CCCC3)CCC1] | WX029 |
| 30 | BB-1 | 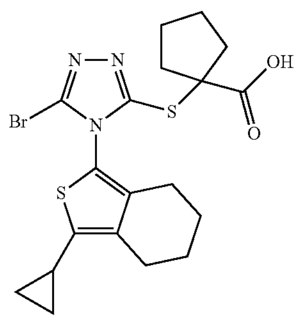 [SMILES: O=C(O)C1(Sc2nnc(Br)n2-c2sc(C3CC3)c3c2CCCC3)CCCC1] | WX030 |
| 31 | BB-1 | 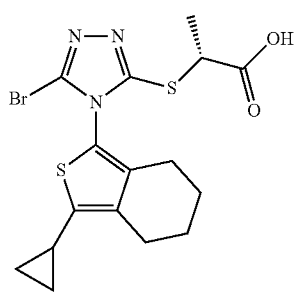 [SMILES: C[C@@H](Sc1nnc(Br)n1-c1sc(C2CC2)c2c1CCCC2)C(=O)O] | WX031 |
| 32 | BB-1 | 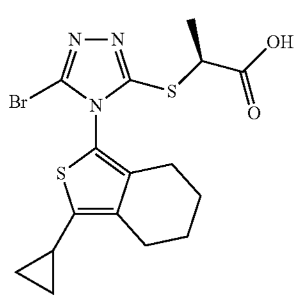 [SMILES: C[C@H](Sc1nnc(Br)n1-c1sc(C2CC2)c2c1CCCC2)C(=O)O] | WX032 |

TABLE 1-continued

| Embodiments | Fragment 1 | Structure | Compound |
|---|---|---|---|
| 33 | BB-7 | 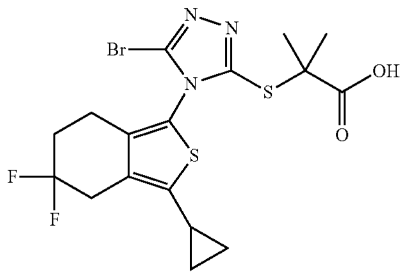 [SMILES: CC(C)(Sc1nnc(Br)n1-c1sc(C2CC2)c2c1CCC(F)(F)C2)C(=O)O] | WX033 |
| 34 | BB-9 | 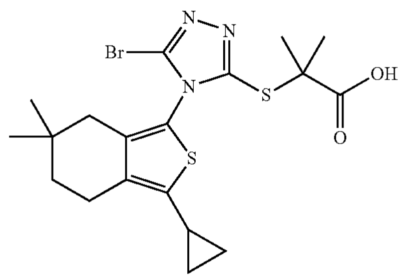 [SMILES: CC1(C)CCc2c(C3CC3)sc(-n3c(Br)nnc3SC(C)(C)C(=O)O)c2C1] | WX034 |
| 35 | BB-5 | 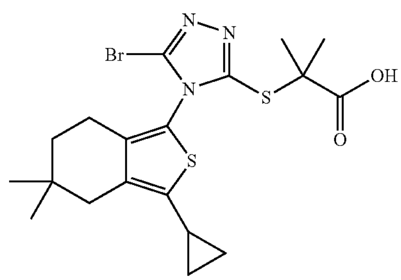 [SMILES: CC1(C)CCc2c(-n3c(Br)nnc3SC(C)(C)C(=O)O)sc(C3CC3)c2C1] | WX035 |
| 37 | BB-8 | 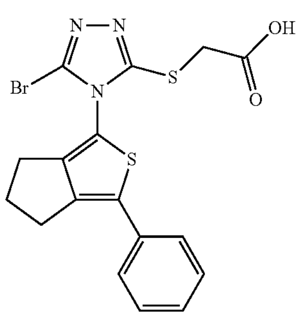 [SMILES: O=C(O)CSc1nnc(Br)n1-c1sc(-c2ccccc2)c2c1CCC2] | WX037 |
| 38 | BB-8 | 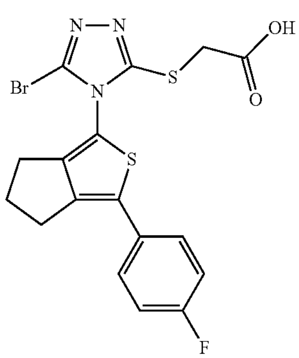 [SMILES: O=C(O)CSc1nnc(Br)n1-c1sc(-c2ccc(F)cc2)c2c1CCC2] | WX038 |

TABLE 1-continued
| Embodiments | Fragment 1 | Structure | Compound |
|---|---|---|---|
| 39 | BB-8 | 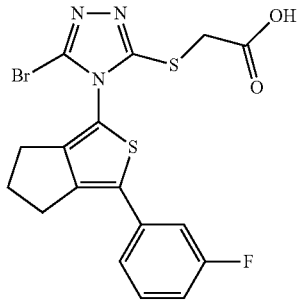 [SMILES: O=C(O)CSc1nnc(Br)n1-c1sc(-c2cccc(F)c2)c2c1CCC2] | WX039 |
| 40 | BB-8 | 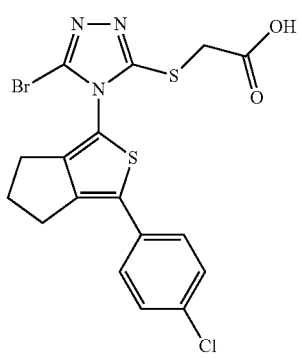 [SMILES: O=C(O)CSc1nnc(Br)n1-c1sc(-c2ccc(Cl)cc2)c2c1CCC2] | WX040 |
| 41 | BB-8 | 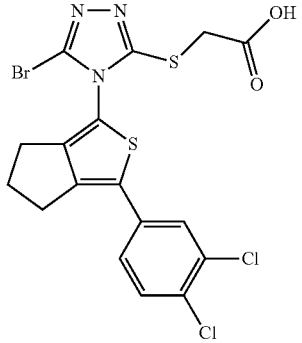 [SMILES: O=C(O)CSc1nnc(Br)n1-c1sc(-c2ccc(Cl)c(Cl)c2)c2c1CCC2] | WX041 |
| 42 | BB-8 | 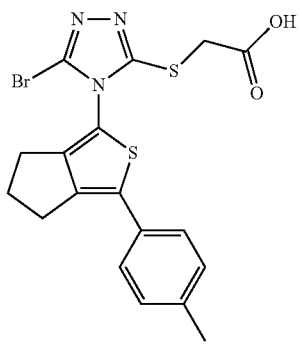 [SMILES: Cc1ccc(-c2sc(-n3c(Br)nnc3SCC(=O)O)c3c2CCC3)cc1] | WX042 |

TABLE 1-continued
| Embodiments | Fragment 1 | Structure | Compound |
|---|---|---|---|
| 43 | BB-8 | 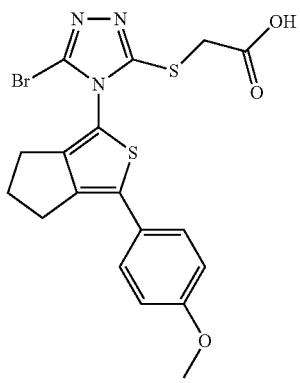 [SMILES: COc1ccc(-c2sc(-n3c(Br)nnc3SCC(=O)O)c3c2CCC3)cc1] | WX043 |
| 44 | BB-8 | 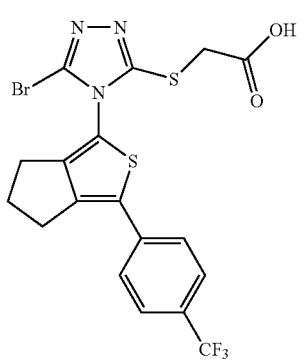 [SMILES: O=C(O)CSc1nnc(Br)n1-c1sc(-c2ccc(C(F)(F)F)cc2)c2c1CCC2] | WX044 |
| 45 | BB-8 | 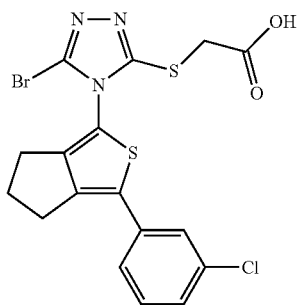 | WX045 |
| 46 | BB-8 | 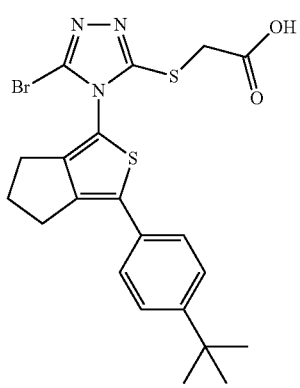 [SMILES: CC(C)(C)c1ccc(-c2sc(-n3c(Br)nnc3SCC(=O)O)c3c2CCC3)cc1] | WX046 |

TABLE 1-continued

| Embodiments | Fragment 1 | Structure | Compound |
|---|---|---|---|
| 47 | BB-8 | 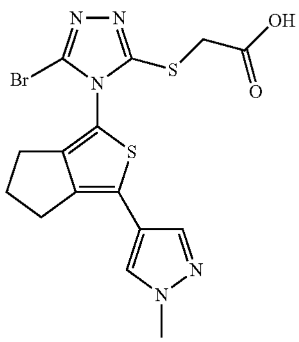 [SMILES: Cn1cc(-c2sc(-n3c(Br)nnc3SCC(=O)O)c3c2CCC3)cn1] | WX047 |
| 58 | BB-8 | 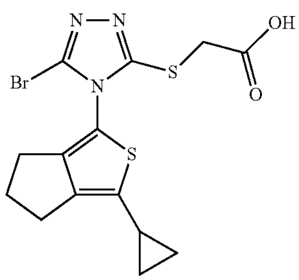 [SMILES: O=C(O)CSc1nnc(Br)n1-c1sc(C2CC2)c2c1CCC2] | WX058 |
| 59 | BB-8 | 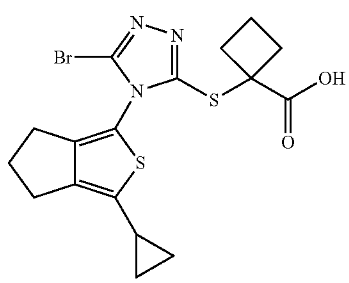 [SMILES: O=C(O)C1(Sc2nnc(Br)n2-c2sc(C3CC3)c3c2CCC3)CCC1] | WX059 |
| 60 | BB-8 | 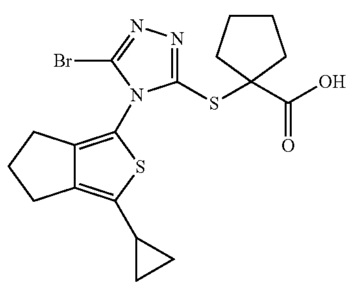 [SMILES: O=C(O)C1(Sc2nnc(Br)n2-c2sc(C3CC3)c3c2CCC3)CCCC1] | WX060 |
| 61 | BB-8 | 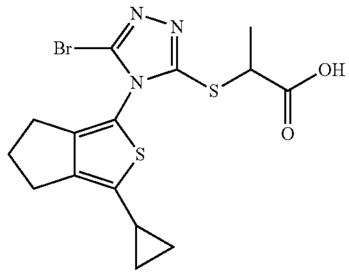 [SMILES: CC(Sc1nnc(Br)n1-c1sc(C2CC2)c2c1CCC2)C(=O)O] | WX061 |

TABLE 1-continued
| Embodiments | Fragment 1 | Structure | Compound |
|---|---|---|---|
| 62 | BB-8 | 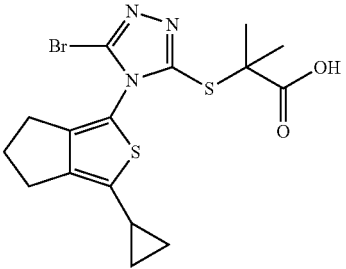 [SMILES: CC(C)(Sc1nnc(Br)n1-c1sc(C2CC2)c2c1CCC2)C(=O)O] | WX062 |
| 63 | BB-8 | 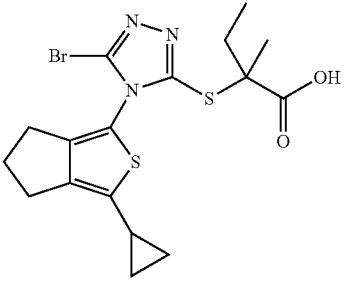 [SMILES: CCC(C)(Sc1nnc(Br)n1-c1sc(C2CC2)c2c1CCC2)C(=O)O] | WX063 |
| 64 | BB-8 | 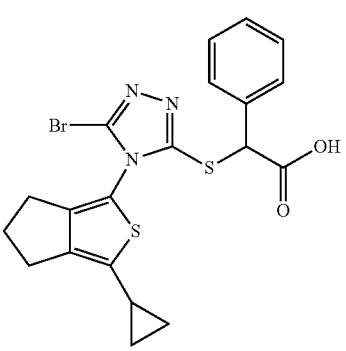 [SMILES: O=C(O)C(Sc1nnc(Br)n1-c1sc(C2CC2)c2c1CCC2)c1ccccc1] | WX064 |
| 65 | BB-6 | 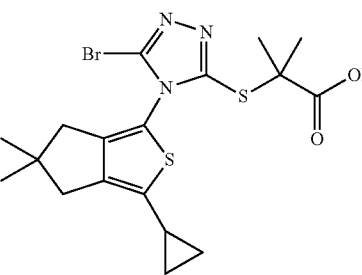 | WX065 |
| 66 | BB-6 | 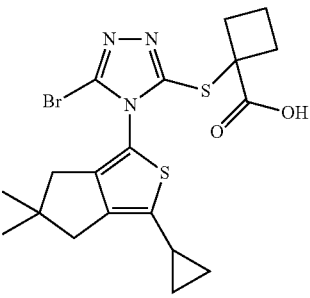 [SMILES: CC1(C)Cc2c(C3CC3)sc(-n3c(Br)nnc3SC3(C(=O)O)CCC3)c2C1] | WX066 |

TABLE 1-continued

| Embodiments | Fragment 1 | Structure | Compound |
|---|---|---|---|
| 67 | BB-4 | 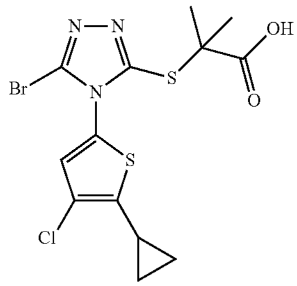 [SMILES: CC(C)(Sc1nnc(Br)n1-c1cc(Cl)c(C2CC2)s1)C(=O)O] | WX067 |
| 68 | BB-4 | 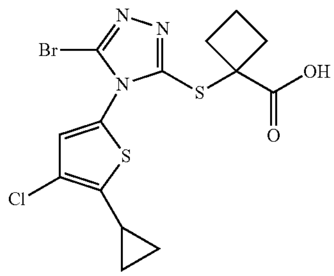 [SMILES: O=C(O)C1(Sc2nnc(Br)n2-c2cc(Cl)c(C3CC3)s2)CCC1] | WX068 |
| 69 | BB-4 | 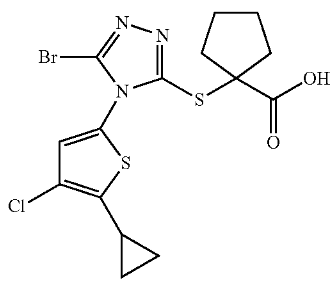 [SMILES: O=C(O)C1(Sc2nnc(Br)n2-c2cc(Cl)c(C3CC3)s2)CCCC1] | WX069 |
| 70 | BB-4 | 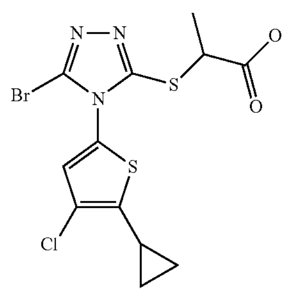 [SMILES: CC(Sc1nnc(Br)n1-c1cc(Cl)c(C2CC2)s1)C(=O)O] | WX070 |
| 71 | BB-4 | 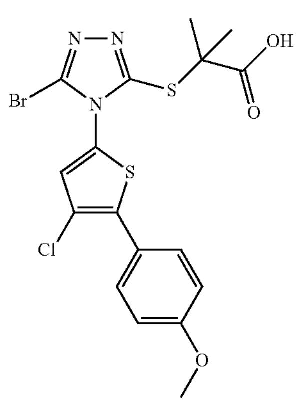 [SMILES: COc1ccc(-c2sc(-n3c(Br)nnc3SC(C)(C)C(=O)O)cc2Cl)cc1] | WX071 |

TABLE 1-continued

| Embodiments | Fragment 1 | Structure | Compound |
|---|---|---|---|
| 78 | BB-3 | (structure) | WX078 |
| 79 | BB-3 | (structure) | WX079 |
| 80 | BB-3 | (structure) | WX080 |
| 81 | BB-3 | (structure) | WX081 |

TABLE 1-continued

| Embodiments | Fragment 1 | Structure | Compound |
|---|---|---|---|
| 82 | BB-3 | 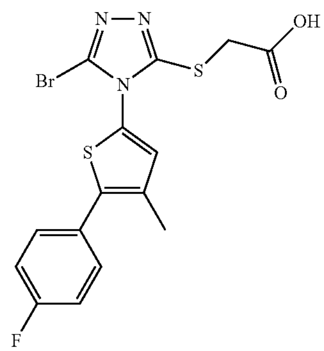 [SMILES: Cc1cc(-n2c(Br)nnc2SCC(=O)O)sc1-c1ccc(F)cc1] | WX082 |
| 83 | BB-3 | 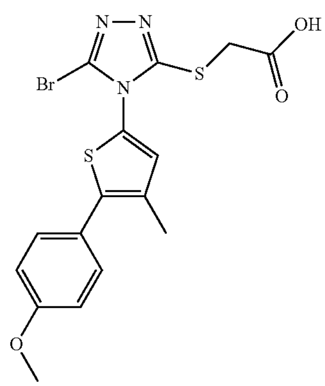 [SMILES: COc1ccc(-c2sc(-n3c(Br)nnc3SCC(=O)O)cc2C)cc1] | WX083 |
| 84 | BB-3 | 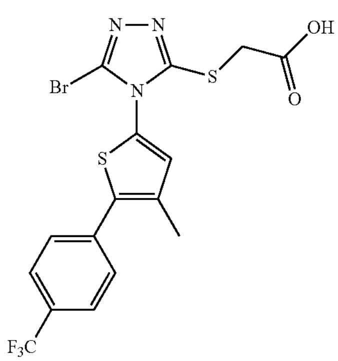 [SMILES: Cc1cc(-n2c(Br)nnc2SCC(=O)O)sc1-c1ccc(C(F)(F)F)cc1] | WX084 |
| 85 | BB-3 | 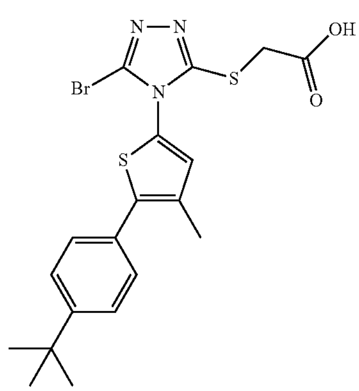 [SMILES: Cc1cc(-n2c(Br)nnc2SCC(=O)O)sc1-c1ccc(C(C)(C)C)cc1] | WX085 |

TABLE 1-continued
| Embodiments | Fragment 1 | Structure | Compound |
|---|---|---|---|
| 86 | BB-3 | 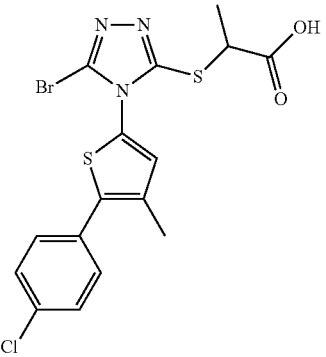 [SMILES: Cc1cc(-n2c(Br)nnc2SC(C)C(=O)O)sc1-c1ccc(Cl)cc1] | WX086 |
| 87 | BB-3 | 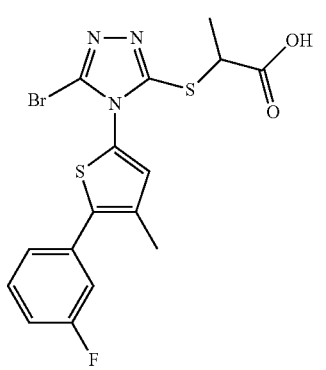 [SMILES: Cc1cc(-n2c(Br)nnc2SC(C)C(=O)O)sc1-c1cccc(F)c1] | WX087 |
| 88 | BB-3 | 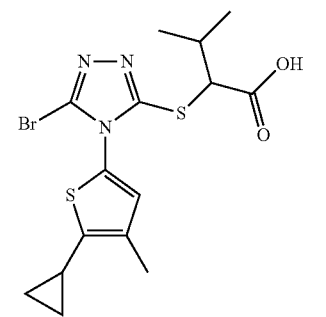 [SMILES: Cc1cc(-n2c(Br)nnc2SC(C(=O)O)C(C)C)sc1C1CC1] | WX088 |
| 89 | BB-3 | 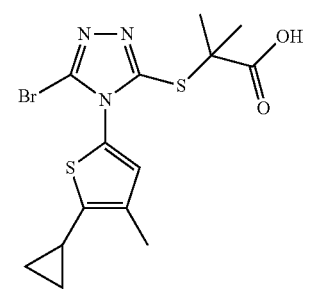 [SMILES: Cc1cc(-n2c(Br)nnc2SC(C)(C)C(=O)O)sc1C1CC1] | WX089 |

TABLE 1-continued

| Embodiments | Fragment 1 | Structure | Compound |
|---|---|---|---|
| 90 | BB-3 | 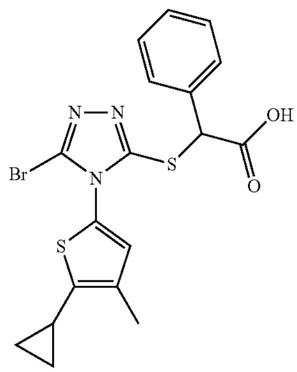 [SMILES: Cc1cc(-n2c(Br)nnc2SC(C(=O)O)c2ccccc2)sc1C1CC1] | WX090 |
| 91 | BB-3 | 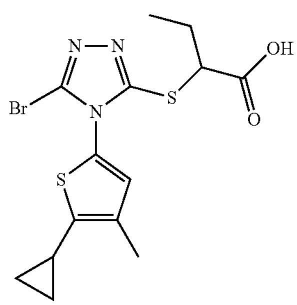 [SMILES: CCC(Sc1nnc(Br)n1-c1cc(C)c(C2CC2)s1)C(=O)O] | WX091 |
| 92 | BB-3 | 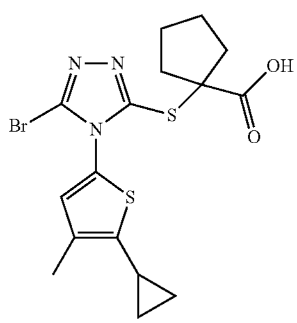 [SMILES: Cc1cc(-n2c(Br)nnc2SC2(C(=O)O)CCCC2)sc1C1CC1] | WX092 |
| 93 | BB-3 | 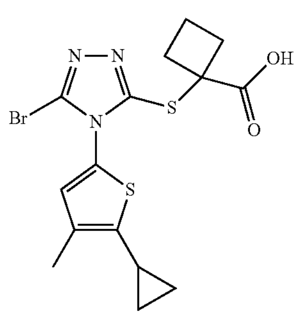 [SMILES: Cc1cc(-n2c(Br)nnc2SC2(C(=O)O)CCC2)sc1C1CC1] | WX093 |

TABLE 1-continued

| Embodiments | Fragment 1 | Structure | Compound |
|---|---|---|---|
| 94 | BB-3 | 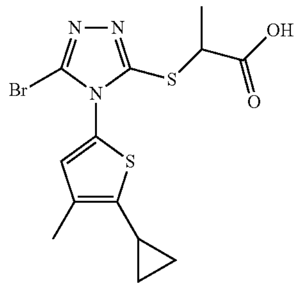 [SMILES: Cc1cc(-n2c(Br)nnc2SC(C)C(=O)O)sc1C1CC1] | WX094 |
| 99 | BB-10 | 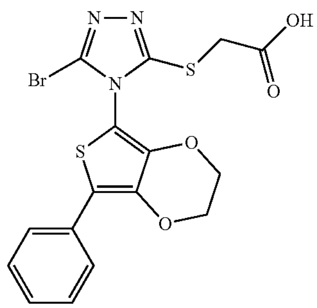 | WX099 |
| 100 | BB-1 | 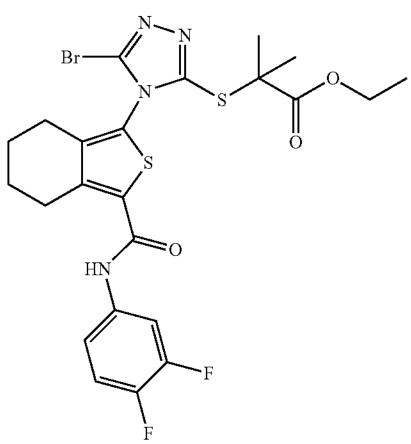 [SMILES: CCOC(=O)C(C)(C)Sc1nnc(Br)n1-c1sc(C(=O)Nc2ccc(F)c(F)c2)c2c1CCCC2] | WX100 |
| 101 | BB-8 | 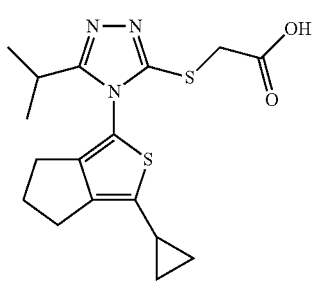 [SMILES: CC(C)c1nnc(SCC(=O)O)n1-c1sc(C2CC2)c2c1CCC2] | WX101 |

TABLE 1-continued
| Embodiments | Fragment 1 | Structure | Compound |
|---|---|---|---|
| 102 | BB-8 | 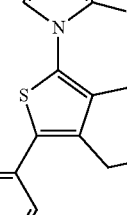 | WX102 |
Embodiments listed in table below were synthesized according to step 1-7 in embodiments 1 and step 1 in embodiments 2. The structures in the table represent their potential rotational isomers and chiral isomers.
TABLE 2
| Embodiments | Fragment | Structure | Compound |
|---|---|---|---|
| 20 | BB-1 | 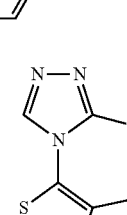 | WX020 |
| 21 | BB-1 | 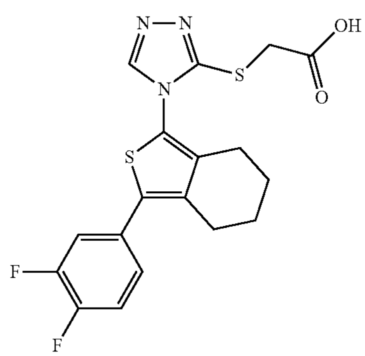 [SMILES: O=C(O)CSc1nncn1-c1sc(-c2ccc(F)c(F)c2)c2c1CCCC2] | WX021 |
| 22 | BB-1 | 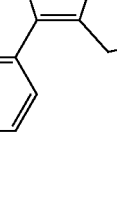 | WX022 |

TABLE 2-continued
| Embodiments | Fragment | Structure | Compound |
|---|---|---|---|
| 23 | BB-1 | 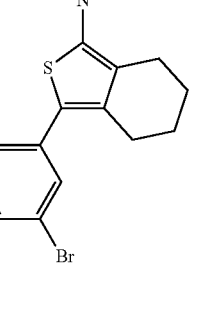 | WX023 |
| 24 | BB-1 | 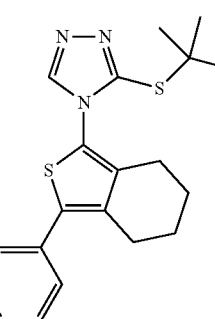 | WX024 |
| 36 | BB-1 | 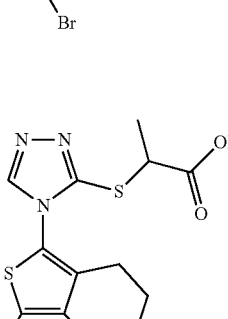 | WX036 |
| 48 | BB-8 | 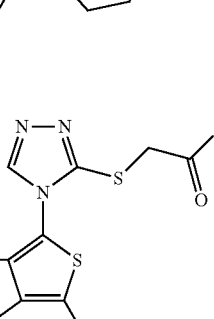 | WX048 |

TABLE 2-continued

| Embodiments | Fragment | Structure | Compound |
|---|---|---|---|
| 49 | BB-8 | 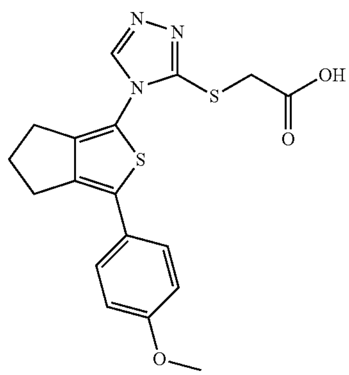 [SMILES: COc1ccc(-c2sc(-n3cnnc3SCC(=O)O)c3c2CCC3)cc1] | WX049 |
| 50 | BB-8 | 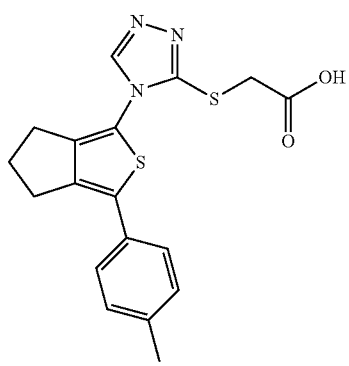 [SMILES: Cc1ccc(-c2sc(-n3cnnc3SCC(=O)O)c3c2CCC3)cc1] | WX050 |
| 51 | BB-8 | 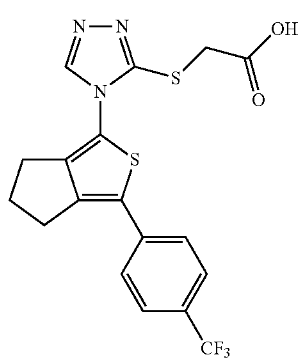 [SMILES: O=C(O)CSc1nncn1-c1sc(-c2ccc(C(F)(F)F)cc2)c2c1CCC2] | WX051 |
| 52 | BB-8 | 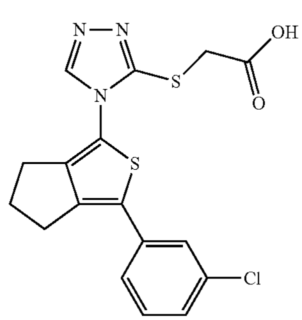 [SMILES: O=C(O)CSc1nncn1-c1sc(-c2cccc(Cl)c2)c2c1CCC2] | WX052 |

TABLE 2-continued
| Embodiments | Fragment | Structure | Compound |
|---|---|---|---|
| 53 | BB-8 | 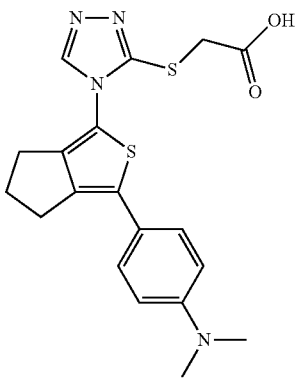 [SMILES: CN(C)c1ccc(-c2sc(-n3cnnc3SCC(=O)O)c3c2CCC3)cc1] | WX053 |
| 54 | BB-8 | 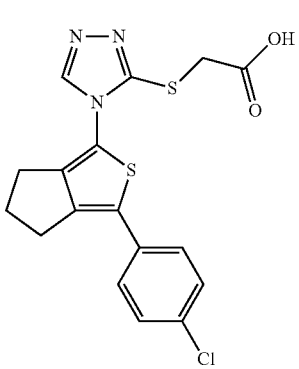 [SMILES: O=C(O)CSc1nncn1-c1sc(-c2ccc(Cl)cc2)c2c1CCC2] | WX054 |
| 55 | BB-8 | 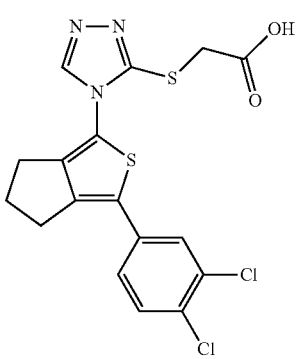 [SMILES: O=C(O)CSc1nncn1-c1sc(-c2ccc(Cl)c(Cl)c2)c2c1CCC2] | WX055 |
| 56 | BB-8 | 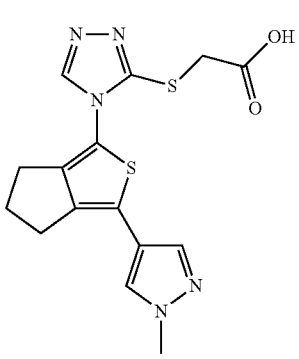 [SMILES: Cn1cc(-c2sc(-n3cnnc3SCC(=O)O)c3c2CCC3)cn1] | WX056 |

TABLE 2-continued
| Embodiments | Fragment | Structure | Compound |
|---|---|---|---|
| 57 | BB-8 | 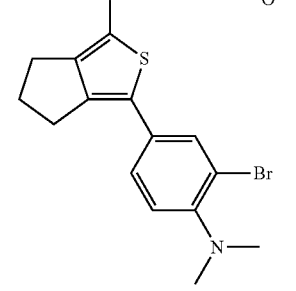 | WX057 |
| 95 | BB-3 | 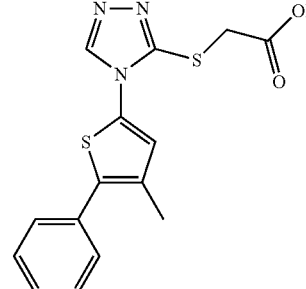 | WX095 |
| 96 | BB-3 | 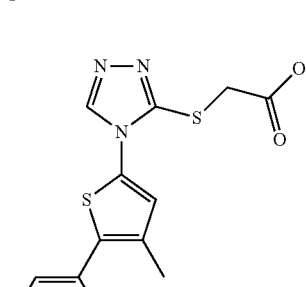 | WX096 |
| 97 | BB-3 | 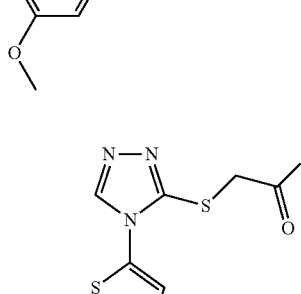 | WX097 |

TABLE 2-continued

| Embodiments | Fragment | Structure | Compound |
|---|---|---|---|
| 98 | BB-3 | (structure) | WX098 |

Embodiments listed in table below were synthesized according to step 1-7 in embodiments 1. The structures in the table represent their potential rotational isomers and chiral isomers.

TABLE 3

| Embodiments | Fragment | Structure | Compound |
|---|---|---|---|
| 72 | BB-2 | (structure) | WX072 |
| 73 | BB-2 | (structure) | WX073 |
| 74 | BB-2 | (structure) | WX074 |

TABLE 3-continued
| Embodiments | Fragment | Structure | Compound |
|---|---|---|---|
| 75 | BB-2 | 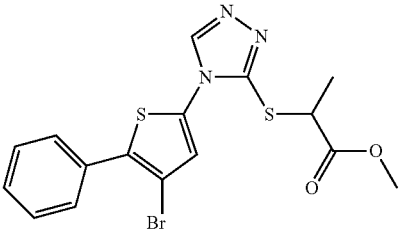 [SMILES: COC(=O)C(C)Sc1nncn1-c1cc(Br)c(-c2ccccc2)s1] | WX075 |
| 76 | BB-2 | 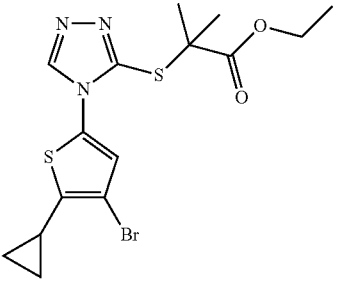 [SMILES: CCOC(=O)C(C)(C)Sc1nncn1-c1cc(Br)c(C2CC2)s1] | WX076 |
| 77 | BB-2 | 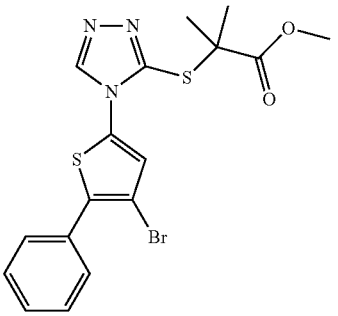 [SMILES: COC(=O)C(C)(C)Sc1nncn1-c1cc(Br)c(-c2ccccc2)s1] | WX077 |
| 103 | BB-1 | 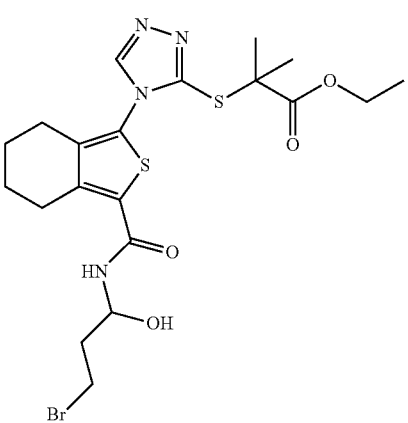 [SMILES: CCOC(=O)C(C)(C)Sc1nncn1-c1sc(C(=O)NC(O)CCBr)c2c1CCCC2] | WX103 |

NMR and MS Data Summarized of all Embodiments

TABLE 4

| Embodiment | Compound | NMR | MS m/z: |
|---|---|---|---|
| 1 | WX001 | $^1$H NMR (400 MHz, Methanol-d$_4$) δ: 4.13-4.01 (m, 2H), 2.77-2.75 (m, 2H), 2.33-2.09 (m, 2H), 2.07-2.06 (m, 1H), 1.84-1.75 (m, 4H), 1.10-1.08 (m, 2H), 0.73-0.70 (m, 2H) | 413.9, 415.9 |
| 2 | WX002 | $^1$H NMR (400 MHz, Methanol-d$_4$) δ: 9.04 (s, 1H), 4.15-4.09 (m, 2H), 2.78-2.75 (m, 2H), 2.46-2.45 (m, 2H), 2.08-2.04 (m, 1H), 1.83-1.75 (m, 4H), 1.09-1.06 (m, 2H), 0.72-0.68 (m, 2H) | 335.9 |
| 3 | WX003 | $^1$H NMR (400 MHz, Methanol-d$_4$) δ: 7.56-7.55 (m, 2H), 7.50-7.47 (m, 2H), 7.43-7.41 (m, 1H), 4.17-4.05 (m, 2H), 2.86-2.85 (m, 2H), 2.58-2.52 (m, 1H), 2.44-2.40 (m, 1H), 1.81-1.77 (m, 4H). | 449.9, 451.8 |
| 4 | WX004 | $^1$H NMR (400 MHz, Methanol-d$_4$) δ: 7.60-7.55 (m, 2H), 7.50-7.47 (m, 2H), 7.43-7.41 (m, 1H), 4.46-4.41 (m, 1H), 2.85-7.75 (m, 2H), 2.50-2.43 (m, 2H), 1.80-1.65 (m, 4H), 1.65 (d, J = 6.8 Hz, 3H) | 463.9, 465.7 |
| 5 | WX005 | $^1$H NMR (400 MHz, Methanol-d$_4$) δ: 7.56-7.54 (m, 2H), 7.49-7.46 (m, 2H), 7.42-7.40 (m, 1H), 2.84 (brs, 2H), 2.30-2.45 (m, 2H), 1.85-1.7 (m, 4H), 1.70 (d, J = 8.0 Hz, 6H). | 477.9, 479.7 |
| 6 | WX006 | $^1$H NMR (400 MHz, Methanol-d$_4$) δ: 7.50 (dd, J = 5.2, J = 8.4 Hz, 2H), 7.16 (t, J = 8.8 Hz, 2H), 4.10-3.99 (m, 2H), 2.68-2.78 (m., 2H), 2.57-2.27 (m, 2H), 1.79-1.68 (m., 4H) | 467.9, 469.8 |
| 7 | WX007 | $^1$H NMR (400 MHz, Methanol-d$_4$) δ: 7.57-7.45 (m, 1H), 7.42-7.34 (m, 1H), 7.34-7.25 (m, 1H), 7.22-7.11 (m, 1H), 4.20-4.02 (m, 2H), 2.87-2.80 (m, 2H), 2.65-2.34 (m, 2H), 1.89-1.75 (m, 4H) | 467.8, 469.9, 489.9 |
| 8 | WX008 | $^1$H NMR (400 MHz, DMSO-d$_6$) δ: 7.36-7.31 (m, 3H), 4.03-3.98 (m, 2H), 2.85 (s, 2H), 2.55-2.40 (m, 2H), 1.71 (s, 4H). | 485.9, 487.8 |
| 9 | WX009 | $^1$H NMR (400 MHz, DMSO-d$_6$) δ: 7.71-7.66 (m, 1H), 7.60-7.53 (m, 1H), 7.42(s, 1H), 4.25-3.98 (m, 2H), 2.81 (s, 2H), 2.55-2.30 (m, 2H), 1.71 (brs, 4H). | 485.9, 487.9 |
| 10 | WX010 | $^1$H NMR (400 MHz, Methanol-d$_4$) δ: 7.81-7.78 (m, 4H), 2.95-2.85 (m, 2H), 2.45-2.35 (m, 2H), 1.85-1.75 (m, 4H), 1.71 (d, J = 10.8 Hz, 6H) | 545.9, 547.8 |
| 11 | WX011 | $^1$H NMR (400 MHz, Methanol-d$_4$) δ: 7.73 (d, J = 4.0 Hz, 1H), 7.65 (d, J = 8.0 Hz 1H), 7.55-7.47 (m, 1H), 2.89-2.79 (m, 2H), 2.46-2.34 (m, 2H), 1.85-1.77 (m., 4H), 1.70 (d, J = 12.0 Hz, 6H) | 545.8, 547.8 |
| 12 | WX012 | $^1$H NMR (400 MHz, Methanol-d$_4$) δ: 7.89 (s, 1H), 7.51-7.49 (m, 1H), 7.14 (d, J = 8.4 Hz, 1H), 4.43-4.40 (m, 1H), 3.93 (s, 3H), 2.85-2.75 (m, 2H), 2.50-2.30 (m, 2H), 1.80-1.65 (m, 4H), 1.63 (d, J = 7.2 Hz, 3H) | 571.8, 572.9, 574.1 |
| 13 | WX013 | $^1$H NMR (400 MHz, Methanol-d$_4$) δ: 7.55-7.47 (m, 1H), 7.45-7.34 (m, 2H), 2.87-2.79 (m, 2H), 2.43-2.33 (m, 2H), 1.84-1.77 (m, 4H), 1.70 (d, J = 11.2 Hz, 6H) | 513.9, 515.8 |
| 14 | WX014 | $^1$H NMR (400 MHz, Methanol-d$_4$) δ: 7.81-7.76 (m, 4H), 4.46-4.41 (m, 1H), 2.95-2.80 (m, 2H), 2.65-2.35 (m, 2H), 1.85-1.75 (m, 4H), 1.66-1.64 (m, 3H) | 531.9, 532.9 |
| 15 | WX015 | $^1$H NMR (400 MHz, Methanol-d$_4$) δ: 8.08 (d, J = 8.4 Hz, 2H), 7.85 (d, J = 8.8 Hz, 2H), 4.46-4.41 (m, 1H), 3.19 (s, 3H), 2.95-2.85 (m, 2H), 2.55-2.45 (m, 2H), 1.85-1.75 (m, 4H), 1.70-1.64 (m, 3H) | 541.9, 543.9 |
| 16 | WX016 | $^1$H NMR (400 MHz, Methanol-d$_4$) δ: 7.48 (d, J = 8.8 Hz, 2H), 7.04 (, J = 8.8 Hz, 2H), 4.46-4.42 (m, 1H), 3.87 (s, 1H), 3.45-3.25 (m, 2H), 2.45-2.35 (m, 1H), 1.85-1.75 (m, 4H), 1.66-1.64 (m, 3H), 1.35-1.25 (m, 1H). | 493.9, 495.8 |
| 17 | WX017 | $^1$H NMR (400 MHz, Methanol-d$_4$) δ: 7.49 (d, J = 8.8 Hz, 2H), 7.04 (J = 8.8 Hz, 2H), 4.15-4.04 (m, 1H), 3.87 (d, J = 5.2 Hz, 2H), 2.80-2.75 (m, 2H), 2.40-2.52 (m, 1H), 1.80-1.65 (m, 4H). | 479.9, 451.9 |
| 18 | WX018 | $^1$H NMR (400 MHz, Methanol-d$_4$) δ: 7.74-7.70 (m, 1H), 7.68-7.61 (m, 1H), 7.54-7.47 (m, 1H), 4.45-4.40 (m, 1H), 2.88-2.80 (m, 2H), 2.52-2.37 (m, 2H), 1.85-1.77 (m., 4H), 1.67-1.62 (m, 3H) | 531.8, 533.8 |
| 19 | WX019 | $^1$H NMR (400 MHz, Methanol-d$_4$) δ: 7.74-7.71 (m, 1H), 7.68-7.63 (m, 1H), 7.54-7.48 (m, 1H), 4.13-4.10 (m, 2H), 2.87-2.83 (m, 2H), 2.55-2.44 (m, 2H), 1.85-1.79 (m, 4H) | 517.8, 519.8 |
| 20 | WX020 | $^1$H NMR (400 MHz, Methanol-d$_4$) δ: 7.51-7.39 (m, 1H), 7.36-7.17 (m, 2H), 7.15-7.03 (m, 1H), 2.84-2.75 (m., 2H), 1.82-1.71 (m., 4H), 1.34-1.21 (m, 4H). | 390 |

TABLE 4-continued

| Embodiment | Compound | NMR | MS m/z: |
|---|---|---|---|
| 21 | WX021 | $^1$H NMR (400 MHz, DMSO-d$_6$) δ: 8.83 (s, 1H), 7.65-7.51 (m, 2H), 7.37 (s, 1H), 4.01 (s, 2H), 2.76 (s, 2H), 2.41 (s, 2H), 1.67 (s, 4H). | 407.9 |
| 22 | WX022 | $^1$H NMR (400 MHz, DMSO-d$_6$) δ: 8.86 (s, 1H), 7.31-7.26 (m, 3H), 4.05 (s, 2H), 2.81 (s, 2H), 2.42 (s, 2H), 1.68 (s, 4H). | 407.9 |
| 23 | WX023 | $^1$H NMR (400 MHz, Methanol-d$_4$) δ: 8.88-8.74 (m, 1H), 7.71 (d, J = 2.0 Hz, 1H), 7.52-7.45 (m, 1H), 7.25 (d, J = 8.4 Hz, 1H), 2.88-2.75 (m, 8H), 2.46 (brs, 2H), 1.79 (brs, 4H), 1.67 (s, 6H) | 520.9 522.9 |
| 24 | WX024 | $^1$H NMR (400 MHz, Methanol-d$_4$) δ: d = 8.79 (s, 1H), 7.67 (s, 2H), 3.03 (s, 3H), 2.86-2.75 (m, 2H), 2.51-2.40 (m, 2H), 1.79 (brs, 4H), 1.66 (s, 6H) | 584.9 588.6 |
| 25 | WX025 | $^1$H NMR (400 MHz, Methanol-d$_4$) δ: 9.41 (s, 1H), 9.25-8.91 (m, 1H), 8.31-8.15 (m, 1H), 3.24 (t, J = 6.0 Hz, 2H), 2.50-2.38 (m, 2H), 2.03-1.90 (m, 2H), 1.86-1.82 (m, 2H), 1.68 (d, J = 7.6 Hz, 6H). | 479.0 481.7 |
| 26 | WX026 | $^1$H NMR (400 MHz, Methanol-d$_4$) δ: 4.51-4.28 (m, 1H), 2.86-2.67 (m, 2H), 2.45-2.19 (m, 2H), 2.13-2.04 (m, 1H), 1.91-1.70 (m, 4H), 1.62 (d, J = 6.8 Hz, 3H), 1.09-1.07 (m, 2H), 0.71-0.70 (m, 2H) | 427.8, 429.9 |
| 27 | WX027 | $^1$H NMR (400 MHz, DMSO-d$_6$) δ: 2.68 (t, J = 6.8 Hz, 2H), 2.16 (t, J = 6.8 Hz, 2H), 2.10-2.00 (m, 1H), 1.75-1.58 (m, 4H), 1.56 (s, 6H), 1.06-0.98 (m, 2H), 0.68-0.57 (m, 2H) | 442.1, 444.1, 465.8 |
| 28 | WX028 | $^1$H NMR (400 MHz, Methanol-d$_4$) δ: 4.25-4.11 (m, 1H), 2.83-2.72 (m, 2H), 2.46-2.24 (m, 3H), 2.12-2.03 (m, 1H), 1.86-1.72 (m, 4H), 1.12-1.01 (m, 8H), 0.75-0.67 (m, 2H) | 455.9, 457.9 |
| 29 | WX029 | $^1$H NMR (400 MHz, Methanol-d$_4$) δ: 2.87-2.75 (m, 4H), 2.40-2.31 (m, 4H), 2.20-2.08 (m, 2H), 1.83-1.73 (m, 4H), 1.09-1.07 (m, 2H), 0.75-0.71 (m, 2H). | 453.8 455.8 |
| 30 | WX030 | $^1$H NMR (400 MHz, Methanol-d$_4$) δ: 2.84-2.66 (m, 2H), 2.56-2.41 (m, 1H), 2.40-2.24 (m, 3H), 2.18-1.98 (m, 3H), 1.93-1.66 (m, 8H), 1.12-1.04 (m, 2H), 0.76-0.66 (m, 2H) | 467.9 469.9 |
| 31 | WX031 | $^1$H NMR (400 MHz, Methanol-d$_4$) δ: 4.35-4.29 (m, 1H), 2.76 (t, J = 6.0 Hz, 2H), 2.46-2.24 (m, 2H), 2.12-2.01 (m, 1H), 2.10-2.01 (m, 1H), 1.85-1.70 (m, 4H), 1.64 (d, J = 7.2 Hz, 3H), 1.12-1.03 (m, 2H), 0.71-0.68 (m, 2H) | 427.9 429.7 |
| 32 | WX032 | $^1$H NMR (400 MHz, Methanol-d$_4$) δ: 4.38-4.32 (m, 1H), 2.85-2.70 (m, 2H), 2.44-2.22 (m, 2H), 2.12-2.03 (m, 1H), 1.89-1.68 (m, 4H), 1.67-1.51 (m, 3H), 1.15-1.00 (m, 2H), 0.72-0.69 (m, 2H). | 427.9 429.8 |
| 33 | WX033 | $^1$H NMR (400 MHz, Methanol-d$_4$) δ: 3.31-3.23 (m, 2H), 2.55-2.51 (m 2H), 2.31-2.14 (m, 2H), 2.12-1.99 (m, 1H), 1.68 (s, 6H), 1.15-1.10 (m, 2H), 0.80-0.68 (m, 2H). | 477.9 479.9 |
| 34 | WX034 | $^1$H NMR (400 MHz, Methanol-d$_4$) δ: 2.77 (t, J = 6.8 Hz, 2H), 2.11-1.94 (m, 3H), 1.70-1.56 (m, 8H), 1.11-1.03 (m, 2H), 0.98-0.93 (m, 6H), 0.75-0.65 (m, 2H). | 469.9 472.0 |
| 35 | WX035 | $^1$H NMR (400 MHz, Methanol-d$_4$) δ: 2.53 (s, 2H), 2.39-2.27 (m, 2H), 1.68 (d, J = 4.4 Hz, 6H), 1.56 (t, J = 6.8 Hz, 2H), 1.09-1.06 (m, 2H), 1.04 (d, J = 7.6 Hz, 6H), 0.73-0.68 (m, 2H). | 469.9 471.9 |
| 36 | WX036 | $^1$H NMR (400 MHz, Methanol-d$_4$) δ: 8.63 (s, 1H), 4.44-4.26 (m, 1H), 2.77-2.74 (m, 2H), 2.46-2.33 (m, 2H), 2.10-2.04 (m, 1H), 1.86-1.67 (m, 4H), 1.60 (d, J = 7.2 Hz, 3H), 1.11-1.01 (m, 2H), 0.70-0.68 (m, 2H) | 350.3 |
| 37 | WX037 | $^1$H NMR (400 MHz, CDCl$_3$) δ: 7.52-7.27 (m, 5H), 4.04 (d, J = 12.0 Hz, 2 H), 2.98 (s, 2H), 2.70-2.34 (m, 4 H). | 435.9 437.9 |
| 38 | WX038 | $^1$H NMR (400 MHz, Methanol-d$_4$) δ: 7.65-7.61 (m, 2 H), 7.21 (t, J = 8.8 Hz, 2 H), 4.10 (d, J = 8.0 Hz, 2 H), 3.04-2.90 (m, 2 H), 2.77-2.57 (m, 2 H), 2.53-2.50 (m, 2 H). | 453.9 456.8 453.9 |
| 39 | WX039 | $^1$H NMR (400 MHz, Methanol-d$_4$) δ: 7.52-7.28 (m, 3 H), 7.17-7.03 (m, 1 H), 4.02 (s, 2 H), 3.01 (t, J = 7.2 Hz, 2 H), 2.80-2.58 (m, 2 H), 2.57-2.44 (m, 2 H). | 456.8 |
| 40 | WX040 | $^1$H NMR (400 MHz, DMSO-d$_6$) δ: 7.61-7.53 (m, 4H), 4.07 (s, 2H), 2.99-2.95 (m, 2H), 2.61-2.55 (m, 2H), 2.46-2.41 (m, 2H). | 469.9 472.2 |
| 41 | WX041 | $^1$H NMR (400 MHz, DMSO-d$_6$) δ: 7.76-7.72 (m, 2H), 7.57-7.55 (m, 1H), 4.07 (s, 2H), 3.01-2.97 (m, 2H), 2.62-2.56 (m, 2H), 2.45-2.41 (m, 2H). | 503.9 505.9 |
| 42 | WX042 | $^1$H NMR (400 MHz, DMSO-d$_6$) δ: 7.43-7.49 (m, 2 H), 7.30-7.28 (m, 2 H), 4.05 (s, 2 H) 2.94 (t, J = 7.2 Hz, 2 H), 2.52-2.58 (m, 2 H), 2.37-2.42 (m, 2 H), 2.33 (s, 3 H). | 449.8 451.8 |
| 43 | WX043 | $^1$H NMR (400 MHz, Methanol-d$_4$) δ: 7.50 (d, J = 8.8 Hz, 2 H), 7.00 (d, J = 8.8 Hz, 2 H), 4.08 (d, J = 8., 4 Hz, 2 H), 3.84 (s, 3 H), 2.9, 6-2.93 (m, 2 H), 2.70-2.55 (m, 2 H), 2.53-2.41(m, 2 H). | 465.8 468.0 |

TABLE 4-continued

| Embodiment | Compound | NMR | MS m/z: |
|---|---|---|---|
| 44 | WX044 | $^1$H NMR (400 MHz, Methanol-d$_4$) δ: 7.81-7.76 (m, 2H), 4.12-4.03 (m, 2H), 3.08-3.04 (m, 2H), 3.08-3.04 (m, 2H), 2.72-2.65 (m, 2H), 2.58-2.53 (m, 2H). | 503.9 505.8 |
| 45 | WX045 | $^1$H NMR (400 MHz, Methanol-d$_4$) δ: 7.59 (s, 1H), 7.56-7.50 (m, 1H), 7.46 (s, 1H), 7.41-7.35 (m, 1H), 4.14-4.04 (m, 2H), 3.03-3.00 (m, 2H), 2.78-2.59 (m, 2H), 2.57-2.49 (m, 2H). | 469.8 471.8 |
| 46 | WX046 | $^1$H NMR (400 MHz, Methanol-d$_4$) δ: 7.52-7.47 (m, 4H), 4.09-4.07 (m, 2H), 3.04-2.90 (m, 2H), 2.74-2.55 (m, 2H), 2.54-2.43 (m, 2H), 1.35 (s, 9H) | 492.0 494.0 |
| 47 | WX047 | $^1$H NMR (400 MHz, Methanol-d$_4$) δ: 7.91 (s, 1H), 7.69 (s, 1H), 4.13-4.03 (m, 2H), 3.95 (s, 3H), 2.92-2.81 (m, 2H), 2.73-2.44 (m, 4H). | 439.7 441.7 |
| 48 | WX048 | $^1$H NMR (400 MHz, Methanol-d$_4$) δ: 8.72 (s, 1H), 7.53-7.37 (m, 4H), 4.13-3.99 (m, 2H), 3.01-2.83 (m, 2H), 2.69-2.60 (m, 2H), 2.49-2.38 (m, 2H), 1.30 (s, 9H) | 414 |
| 49 | WX049 | $^1$H NMR (400 MHz, DMSO-d$_6$) δ: 8.89 (s, 1 H), 7.47 (d, J = 8.8 Hz, 2 H), 7.02 (d, J = 8.8 Hz, 2 H), 4.07 (s, 2 H), 3.78 (s, 3 H), 2.81-2.95 (m, 2 H), 2.63-2.55 (m, 2 H), 2.40-2.34 (m, 2H). | 388 |
| 50 | WX050 | $^1$H NMR (400 MHz, DMSO-d$_6$) δ: 8.89 (s, 1 H), 7.42 (s, 2 H), 7.29-7.24 (m, 2 H), 4.04 (s, 2 H), 2.91 (t, J = 7.2 Hz, 2 H), 2.58-2.64 (m, 2 H), 2.34-2.41 (m, 2 H), 2.32 (s, 3 H). | 372 |
| 51 | WX051 | $^1$H NMR (400 MHz, Methanol-d$_4$) δ: 8.73 (s, 1H), 7.79-7.74 (m, 4H), 4.05 (s, 2H), 3.04 (t, J = 7.2 Hz, 2H), 2.75 (t, J = 7.6 Hz, 2H), 2.57-2.51 (m, 2H). | 426 |
| 52 | WX052 | $^1$H NMR (400 MHz, Methanol-d$_4$) δ: 8.76 (s, 1H), 7.60-7.56 (m, 1H), 7.55-7.50 (m, 1H), 7.47-7.43 (m, 1H), 7.39-7.33 (m, 1H), 4.11 (s, 2H), 3.02-3.98 (m, 2H), 2.80-2.68 (m, 2H), 2.55-2.48 (m, 2H). | 392 |
| 53 | WX053 | $^1$H NMR (400 MHz, Methanol-d$_4$) δ: 8.74 (s, 1H), 7.55-7.47 (m, 2H), 7.10-6.92 (m, 2H), 4.11 (s, 2H), 3.08 (s, 6H), 3.01-2.92 (m, 2H), 2.69 (s, 2H), 2.54-2.45 (m, 2H) | 401.1 |
| 54 | WX054 | $^1$H NMR (400 MHz, DMSO-d$_6$) δ: 8.91 (s, 1H), 7.57-7.51 (m, 4H), 4.06 (s, 2H), 2.94-2.90 (m, 2H), 2.64-2.60 (m, 2H), 2.41-2.37 (m, 2H). | 391.9 |
| 55 | WX055 | $^1$H NMR (400 MHz, DMSO-d$_6$) δ: 8.90 (s, 1H), 7.72-7.69 (m, 2H), 7.53-7.51 (m, 1H), 4.05 (s, 2H), 2.96-2.92 (m, 2H), 2.65-2.61 (m, 2H), 2.48-2.37 (m, 2H). | 425.9 |
| 56 | WX056 | $^1$H NMR (400 MHz, Methanol-d$_4$) δ: 8.75 (s, 1H), 7.89 (s, 1H), 7.67 (s, 1H), 4.10 (s, 2H), 3.94 (s, 3H), 2.90-2.81 (m, 2H), 2.71-2.67 (s, 2H), 2.56-2.44 (m, 2H) | 361.9 |
| 57 | WX057 | $^1$H NMR (400 MHz, Methanol-d$_4$) δ: 8.73 (s, 1H), 7.79-7.68 (m, 1H), 7.56-7.47 (m, 1H), 7.27-7.19 (m, 1H), 4.08 (s, 2H), 2.99-2.91 (m, 2H), 2.83 (s, 6H), 2.74-2.66 (m, 2H), 2.56-2.45 (m, 2H). | 478.9 481.0 |
| 58 | WX058 | $^1$H NMR (400 MHz, CDCl$_3$) δ: 4.05-3.88 (m, 2H), 2.78-2.67 (m, 2H), 2.58-2.48 (m, 2H), 2.47-2.36 (m, 2H), 1.98-1.93 (m, 1H), 1.06-1.02 (m, 2 H), 0.81-0.72 (m, 2H). | 400.0, 401.7 |
| 59 | WX059 | $^1$H NMR (400 MHz, Methanol-d$_4$) δ: 2.90-2.70 (m, 4H), 2.55-2.45 (m, 2H), 2.45-2.35 (m, 4H), 2.25-2.15 (m, 1H), 2.10-2.00 (m, 2H), 1.05-1.00 (m, 2H), 0.70-0.65 (m, 2H). | 439.8 441.8 |
| 60 | WX060 | $^1$H NMR (400 MHz, Methanol-d$_4$) δ: 3.65(s, 3H), 2.80-2.71 (m, 2 H), 2.60-2.51 (m, 2 H), 2.50-2.25 (m, 4H), 1.95-2.05 (m, 3H), 1.90-1.70 (m, 4 H), 1.35-1.25 (m, 1H), 1.05-1.00 (m, 2 H), 0.78-0.69 (m, 2 H). | 467.9 470.0 |
| 61 | WX061 | $^1$H NMR (400 MHz, CDCl$_3$) δ: 4.45-4.30 (m, 1H), 2.75-2.70 (m, 2H), 2.62-2.30 (m, 4H), 2.00-1.90 (m, 1H), 1.66 (d, J = 7.0 Hz, 3H), 1.14-0.97 (m, 2H), 0.80-0.65 (m, 2H). | 413.9 415.7 |
| 62 | WX062 | $^1$H NMR (400 MHz, CDCl$_3$) δ: 2.74 (t, J = 7.2 Hz, 2H), 2.56-2.33 (m, 4H), 2.00-1.89 (m, 1H), 1.72 (d, J = 3.2 Hz, 6H), 1.09-0.99 (m, 2H), 0.84-0.72 (m, 2H). | 427.9 429.7 |
| 63 | WX063 | $^1$H NMR (400 MHz, DMSO-d$_6$) δ: 2.68-2.51 (m, 2H), 2.41-2.39 (m, 3H), 2.32-2.25 (m, 2H), 2.10-0.98 (m, 2H), 1.90-1.85 (m, 1H), 1.50 (d, J = 9.2 Hz, 3H), 1.02-1.00 (m, 2H), 0.95-0.80 (m, 3H), 0.71-0.69 (m, 2H) | 441.8 443.8 |
| 64 | WX064 | $^1$H NMR (400 MHz, Methanol-d$_4$) δ: 7.42-7.24 (m, 5H), 5.39 (d, J = 11.6 Hz, 1H), 2.65-2.50 (m, 2H), 2.35-2.20 (m, 2H), 1.95-1.80 (m, 1H), 1.35-1.20 (m, 2H), 0.95-0.80 (m, H), 0.65-0.55 (m, 2H). | 475.8 477.7 |
| 65 | WX065 | $^1$H NMR (400 MHz, Methanol-d$_4$) δ: 2.57 (d, J = 2.0 Hz, 2H), 2.32 (d, J = 4.0 Hz, 2H), 2.05-1.94 (m, 1H), 1.65 (d, | 455.7 457.7 |

TABLE 4-continued

| Embodiment | Compound | NMR | MS m/z: |
|---|---|---|---|
| | | J = 2.0 Hz, 6H), 1.20 (d, J = 4.0 Hz, 6H), 1.07-1.01 (m, 2H), 0.78-0.70 (m, 2H). | |
| 66 | WX066 | $^1$H NMR (400 MHz, DMSO-d$_6$) δ: 2.78-2.61 (m, 2H), 2.21-2.33 (m, 4H), 2.13-1.81 (m, 3H), 1.13 (s., 6H), 1.05-0.94 (m, 2H), 0.73-0.65 (m, 2H). | 467.9 469.9 |
| 67 | WX067 | $^1$H NMR (400 MHz, Methanol-d$_4$) δ: 7.11 (s, 1H), 2.30-2.18 (m, 1H), 1.64 (s, 6H), 1.23-1.15 (m 2H), 0.84-0.77 (m, 2H) | 421.9 423.9 |
| 68 | WX068 | $^1$H NMR (400 MHz, Methanol-d$_4$) δ: 7.12 (s, 1H), 2.85-2.71 (m, 2H), 2.47-2.33 (m, 2H), 2.31-2.16 (m, 2H), 2.10-1.94 (m, 1H), 1.23-1.16 (m, 2H), 0.84-0.74 (m, 2H) | 433.8 435.6 |
| 69 | WX069 | $^1$H NMR (400 MHz, Methanol-d$_4$) δ: 7.12 (s, 1H), 2.42-2.29 (td, J = 6.8, 13.6 Hz, 2H), 2.28-2.18 (m, 1H), 2.14-2.02 (m, 2H), 1.93-1.74 (m, 4H), 1.23-1.13 (m, 2H), 0.84-0.75 (m, 2H). | 447.9 449.6 |
| 70 | WX070 | $^1$H NMR (400 MHz, Methanol-d$_4$) δ: 7.17 (s, 1H), 4.29 (q, J = 7.2 Hz, 1H), 2.33-2.17 (m, 1H), 1.61 (d, J = 7.2 Hz, 3H), 1.2-1.18 (m, 2H), 0.84-0.78 (m, 2H). | 407.9 409.6 |
| 71 | WX071 | $^1$H NMR (400 MHz, Methanol-d$_4$) δ: 7.67-7.65 (m, 2H), 7.30-7.24 (m, 1H), 7.07 (d, J = 8.8 Hz, 2H), 3.88 (s, 3H), 1.67 (s, 6H). | 487.9 489.7 |
| 72 | WX072 | $^1$H NMR (400 MHz, Methanol-d$_4$) δ: 8.71 (s, 1H), 7.22 (s, 1H), 4.59 (s, 1H), 4.19 (q, J = 7.2 Hz, 2H), 4.06-3.99 (m, 1H), 2.22-2.18 (m, 1H), 1.28-1.25 (m, 3H), 1.21-1.18 (m, 2H), 0.82-0.79 (m, 2H). | 387.9, 389.8 |
| 73 | WX073 | $^1$H NMR (400 MHz, Methanol-d$_4$) δ: 8.82 (s, 1H), 7.70-7.68 (m, 2H), 7.52-7.49 (m, 3H), 7.42 (s, 1H), 4.13 (s, 2H), 3.76 (s, 3H). | 409.9, 411.8 |
| 74 | WX074 | $^1$H NMR (400 MHz, Methanol-d$_4$) δ: 8.78 (s, 1H), 7.20 (s, 1H), 4.26-4.24 (m, 1H), 4.15-4.10 (m, 2H), 2.22-2.17 (m, 1H), 1.58-1.56 (m, 3H), 1.24-1.17 (m, 5H), 0.82-0.78 (m, 2H). | 401.8, 403.9 |
| 75 | WX075 | $^1$H NMR (400 MHz, Methanol-d$_4$) δ: 8.87 (s, 1H), 7.69-7.67 (m, 2H), 7.53-7.48 (m, 3H), 7.39 (s, 1H), 4.32-4.31 (m, 1H), 3.69 (s, 3H), 1.60 (d, J = 7.2 Hz, 3H). | 423.9, 425.8 |
| 76 | WX076 | $^1$H NMR (400 MHz, Methanol-d$_4$) δ: 8.85 (s, 1H), 7.18 (s, 1H), 4.03 (q, J = 7.2 Hz, 2H), 2.20-2.16 (m, 1H), 1.59 (s, 6H), 1.22-1.17 (m, 5H), 0.81-0.77 (m, 2H). | 415.8, 417.9 |
| 77 | WX077 | $^1$H NMR (400 MHz, Methanol-d$_4$) δ: 8.97 (s, 1H), 7.70-7.68 (m, 2H), 7.52-7.48 (m, 3H), 7.40 (s, 1H), 3.61 (s, 3H), 1.63 (s, 6H). | 437.9, 439.8 |
| 78 | WX078 | $^1$H NMR (400 MHz, CDCl$_3$) δ: 6.79 (s, 1H), 3.91 (s, 2H), 2.29 (s, 3H), 2.06-1.94 (m, 1H), 1.14-1.03 (m, 2H), 0.79-0.69 (m, 2H) | 374.0, 376.0 |
| 79 | WX079 | $^1$H NMR (400 MHz, CDCl$_3$) δ: 7.49-7.26 (m, 5H), 6.97 (s, 1H), 4.00 (s, 2H), 2.36 (s, 3H) | 409.8, 411.9 |
| 80 | WX080 | $^1$H NMR (400 MHz, CDCl$_3$) δ: 7.39-7.53 (m, 5H), 6.99 (s, 1H), 4.51-4.35 (m, 1H), 2.36 (s, 3H), 1.68-1.62 (m, 3H) | 446.0, 448.0 |
| 81 | WX081 | $^1$H NMR (400 MHz, CDCl$_3$) δ: 7.53-7.40 (m, 5H), 6.94 (brs, 1H), 2.37 (s., 3H), 1.72 (s, 6H) | 460.0, 462.0 |
| 82 | WX082 | $^1$H NMR (400 MHz, CDCl$_3$) δ: 7.46 (dd, J = 8.8, 5.2 Hz, 2H), 7.16 (t, J = 8.8 Hz, 2H), 6.97 (s, 1H), 4.01 (s, 2H), 2.33 (s, 3H) | 427.7, 429.7, 451.8 |
| 83 | WX083 | $^1$H NMR (400 MHz, Methanol-d$_4$) δ: 7.43-7.49 (m, 1H), 7.14-7.16 (m, 1H), 7.02-7.08 (m, 2H), 4.08 (s, 2H), 3.87 (s, 3H), 2.34 (s, 3H) | 440.0, 442.0, 463.8 |
| 84 | WX084 | $^1$H NMR (400 MHz, CDCl$_3$) δ: 7.80-7.66 (m, 2H), 7.60 (d, J = 8.0 Hz, 2H), 7.03 (s, 1H), 4.02 (brs, 1H), 2.36 (s, 3H). | 478.0 480.0 |
| 85 | WX085 | $^1$H NMR (400 MHz, CDCl$_3$) δ: 7.47-7.54 (m, 2H), 7.39-7.46 (m, 2H), 7.28 (s, 2H), 6.97 (s, 1H), 4.00 (s, 2H), 2.38 (s, 3H), 1.38 (s, 9H) | 466.2, 468.1 |
| 86 | WX086 | $^1$H NMR (400 MHz, Methanol-d$_4$) δ: 7.60-7.50 (m, 4H), 7.17 (s, 1H), 4.40-4.35 (m, 1H), 2.36 (s, 3H), 1.62 (d, J = 7.2 Hz, 3H). | 457.9 459.9 |
| 87 | WX087 | $^1$H NMR (400 MHz, Methanol-d$_4$) δ: 7.65-7.55 (m, 1H), 7.45-7.35 (m, 1H), 7.30-7.27 (m, 1H), 7.22-7.17 (m, 2H), 4.37-4.3 (m, 1H), 2.38 (s, 3H), 1.63 (d, J = 7.2 Hz, 3H) | 441.9, 443.9 |
| 88 | WX088 | $^1$H NMR (400 MHz, Methanol-d$_4$) δ: 6.96 (s, 1H), 4.16-4.06 (m, 1H), 2.32 (s, 3H), 2.30-2.23 (m, 1H), 2.14-2.04 (m, 1H), 1.12-1.05 (m, 8H), 0.76-0.68 (m, 2H) | 416.0, 418.1 |
| 89 | WX089 | $^1$H NMR (400 MHz, Methanol-d$_4$) δ: 6.89 (m, 1H), 2.31 (s, 3H), 2.14-2.02 (m, 1H), 1.63 (s, 6H), 1.13-1.05 (m, 2H), 0.76-0.68 (m, 2H). | 401.8, 403.7 |

TABLE 4-continued

| Embodiment | Compound | NMR | MS m/z: |
|---|---|---|---|
| 90 | WX090 | $^1$H NMR (400 MHz, Methanol-d$_4$) δ: 7.42-7.38 (m, 2H), 7.36-7.34 (m, 3H), 6.71 (s, 1H), 5.49-5.40 (m, 1H), 2.28 (s, 3H), 2.08 (t, J = 4.8 Hz, 1H), 1.12-1.04 (m, 2H), 0.74-0.66 (m, 2H) | 449.8, 451.9 |
| 91 | WX091 | $^1$H NMR (400 MHz, Methanol-d$_4$) δ: 6.95 (s, 1H), 4.18 (t, J = 6.4 Hz, 1H) 2.31 (s, 3H), 2.17-2.06 (m, 1H), 2.04-1.88 (m, 2H), 1.14-1.07 (m, 2H), 1.05-1.00 (m, 3H), 0.75-0.68 (m, 2H) | 401.8, 403.9, 425.9 |
| 92 | WX092 | $^1$H NMR (400 MHz, Methanol-d$_4$) δ: 6.90 (s, 1H), 2.42-2.32 (m, 2H), 2.31 (s, 3H), 2.11-2.03 (m, 3H), 1.92-1.74 (m, 4H), 1.12-1.07 (m, 2H), 0.73-0.69(m, 2H). | 427.9, 429.9 |
| 93 | WX093 | $^1$H NMR (400 MHz, Methanol-d$_4$) δ: 6.95 (s, 1H), 2.87-2.69 (m, 2H), 2.44-2.34 (m, 2H), 2.31 (s, 3H), 2.27-2.16 (m, 1H), 2.14-1.95 (m, 2H), 1.17-1.02 (m, 2H), 0.76-0.70 (m, 2H) | 413.9, 415.8 |
| 94 | WX094 | $^1$H NMR (400 MHz, Methanol-d$_4$) δ: 6.96 (d, J = 5.2 Hz, 1H), 4.38-4.22 (m, 1H), 2.31 (s, 3H), 2.18-2.00 (m, 1H), 1.59 (t, J = 7.2 Hz, 3H), 1.18-1.01 (m, 2H), 1.12-1.05 (m, 2H). | 387.9, 389.8 |
| 95 | WX095 | $^1$H NMR (400 MHz, CDCl$_3$) δ: 8.31 (s, 1H), 7.47-7.38 (m, 2H), 7.18-7.14 (m, 2 H), 7.16 (s, 2H), 6.97 (s, 1H), 3.99 (s, 2H), 2.31 (s, 3H) | 349.9 |
| 96 | WX096 | $^1$H NMR (400 MHz, Methanol-d$_4$) δ: 8.73-8.77 (m, 1H), 7.44 (d, J = 8.8 Hz, 2H), 7.15 (s, 1H), 7.05 (d, J = 8.8 Hz, 2H), 4.11 (s, 2H), 3.87 (s, 3H). | 362 |
| 97 | WX097 | $^1$H NMR (400 MHz, CDCl$_3$) δ: 8.35 (s, 1H), 7.75 (d, J = 8.4 Hz, 2H), 7.60 (d, J = 8.0 Hz, 2H), 7.03 (s, 1H), 4.02 (s, 2H), 2.38 (s, 3H) | 400.3 |
| 98 | WX098 | $^1$H NMR (400 MHz, CDCl$_3$) δ: 8.34 (s, 1H), 7.46-7.53 (m, 2H), 7.36-7.44 (m, 2H), 6.98 (s, 1H), 3.99 (s, 2H), 2.36 (s, 3H), 1.39 (s, 9H). | 389.1 |
| 99 | WX099 | $^1$H NMR (400 MHz, Methanol-d$_4$) δ: 7.80-7.71 (m, 2H), 7.47-7.38 (m, 2H), 7.36-7.28 (m, 1H), 4.47-4.34 (m, 4H), 4.10-3.99 (m, 2H) | 453.7, 455.7 |
| 100 | WX100 | $^1$H NMR (400 MHz, Methanol-d$_4$) δ: 7.78-7.83 (m, 1 H), 7.37-7.28 (m, 2 H), 4.20-4.14 (m, 2 H), 3.02-3.14 (m, 2 H), 2.43-2.41 (s, 2 H), 1.93-1.73 (m, 4 H), 1.69 (s, J = 5.2 HZ, 6 H), 1.23 (t, J = 6.8 Hz, 3 H). | 585.1, 587.1 |
| 101 | WX101 | $^1$H NMR (400 MHz, CDCL$_3$) δ: 4.19- 3.98 (m, 2H), 3.06-3.00 (m, 1H), 2.72 (d, J = 7.2 Hz, 2H), 2.63-2.50 (m, 1H), 2.49-2.30 (m, 3H), 2.01-1.89 (m, 1H), 1.37 (d, J = 6.8 Hz, 3H), 1.29 (d, J = 6.8 Hz, 3H), 1.09-0.99 (m, 2H), 0.81-0.72 (m, 2H). | 364.0 |
| 102 | WX102 | $^1$H NMR (400 MHz, DMSO-d$_6$) δ: 2.68-2.60 (m, 2H), 2.49-2.38 (m, 2H), 2.35-2.20 (m, 2H), 2.05-1.95 (m, 1H), 1.05-0.95 (m, 2H), 0.72-0.63 (m, 2H). | 442.9, 444.7 |
| 103 | WX103 | $^1$H NMR (400 MHz, Methanol-d$_4$) δ: 9.19 (d, J = 4 Hz, 1H), 5.46 (t, J = 4 Hz, 1H), 4.05 (q, J = 8.0 Hz, 2H), 3.57-3.51 (m, 2H), 3.07-3.02 (m, 2H), 2.49-2.39 (m, 2H), 2.38-2.32 (m 1H), 2.22-2.15 (m, 1H), 1.90-1.75 (m, 4H), 1.66 (d, J = 4 Hz, 6H), 1.19 (t, J = 4 Hz, 3H). | 530.9, 533.0 |

Testing Embodiment 1: Evaluation In Vitro

Experimental Purpose:

Determination of the IC$_{50}$ value of the inhibitory activity of the compound against uric acid reabsorption by the HEK293 cell line stably transfected with the URAT-1 (uric acid transporter) gene.

Background Introduction:

Gout is a progressive disease induced by abnormal elevation of the uric acid level in blood. The coding URAT-1 gene exists in uric acid transporter in renal tubules. Small molecule compounds can promote uric acid excretion by inhibiting the function of this protein, thereby preventing gout attacks.

Experimental Ingredients:

URAT-1 (HEK293) cell line: the HEK293 cell line stably transfected with the URAT-1 gene cell culture medium: DMEM culture medium added 10% fetal bovine serum (FBS), 1% sodium pyruvate and 300 ul/ml G418.

HBSS buffer solution.

0.1 M NaOH solution.

Uric acid solution labeled by $^{14}$C.

CO$_2$ incubator.

liquid scintillation counter Tri-Carb

Experimental procedure and method:

a) cell seeding:

1) the supernatant of cell culture was aspirated, and cells was washed with 10 mL PBS.

2) preheated trypsin was added into the cell culture flask, and the cell culture flask was rotated to make trypsin covering onto the bottom of cell culture flask equably.

3) the cells were suspended with 10-15 mL of culture medium in each T150 flask, took 0.1 mL of cell suspension and diluted it with two volumes of trypan blue solution to count the cells.

4) cells were diluted to 2.5×10$^5$/mL with the culture medium, and the diluted cells were added into a rat tail collagen-coated 24-well plate (800 uL/well, $2\times10^5$ cells/well). The plate was incubated overnight at 37° C. in a 5% $CO_2$ incubator.

b) cell preparation 1) cells were seeded into 24-well plate, and supernatant was discarded after 16-18 h. The cells were washed twice using 600 ul HBSS buffer.

2) HBSS buffer was removed and 180 ul of HBSS buffer was added into each well again.

c) preparation, dilution and sampling of compound solution 1) compounds were dissolved into 100% DMSO, and diluted into 6 concentration points by 3-fold dilution, or into 2 concentration points by 10-fold dilution, and the highest starting concentration was 50 mM.

2) 5 ul DMSO solution in step 1) was transferred into 120 ul of HBSS buffer to make a 25-fold dilution.

3) 10 ul diluted solution in step 2) was added into 24-well plate, and the plate was incubated for 15 min at 37° C. in a 5% $CO_2$ incubator. The final concentration of DMSO is 0.2%. The control well contained 0.2% DMSO without compound.

d) testing:

$^{14}C$-labelled uric acid was diluted and added into plate, and the final concentration is 50 um. The plate was incubated for 10 min at 37° C. in a 5% $CO_2$ incubator. After supernatant was discarded, cells were washed with HBSS buffer twice. Cells was lysed with 0.1M NaOH. And then cell lysis solution was collected into liquid scintillation tube and added with liquid scintillation solution. The signal was read by liquid scintillation counter Tri-Carb.

e) data analysis

URAT-1 inhibition by the treatment of the compounds was analyzed by calculating the percentage of inhibition. Non-linear fitting analysis of percent inhibition (inh %) data using GraphPad Prism software to generate the IC50 value. Experiment results as listed in table 5.

TABLE 5 testing results of inhibition of all embodiments against URAT-1

| Embodiment | Compound | $IC_{50}$ |
|---|---|---|
| 1 | WX001 | A |
| 2 | WX002 | C |
| 3 | WX003 | B |
| 4 | WX004 | B |
| 5 | WX005 | A |
| 6 | WX006 | B |
| 7 | WX007 | B |
| 8 | WX008 | B |
| 9 | WX009 | A |
| 10 | WX010 | B |
| 11 | WX011 | A |
| 12 | WX012 | A |
| 13 | WX013 | A |
| 14 | WX014 | A |
| 15 | WX015 | C |
| 16 | WX016 | B |
| 17 | WX017 | B |
| 18 | WX018 | B |
| 19 | WX019 | B |
| 20 | WX020 | C |
| 21 | WX021 | C |
| 22 | WX022 | C |
| 23 | WX023 | B |
| 24 | WX024 | B |
| 25 | WX025 | C |
| 26 | WX026 | A |
| 27 | WX027 | A |
| 28 | WX028 | A |
| 29 | WX029 | A |
| 30 | WX030 | A |
| 31 | WX031 | A |
| 32 | WX032 | A |
| 33 | WX033 | A |
| 34 | WX034 | A |
| 35 | WX035 | A |
| 36 | WX036 | C |
| 37 | WX037 | C |
| 38 | WX038 | C |
| 39 | WX039 | C |
| 40 | WX040 | C |
| 41 | WX041 | C |
| 42 | WX042 | C |
| 43 | WX043 | C |
| 44 | WX044 | C |
| 45 | WX045 | C |
| 46 | WX046 | C |
| 47 | WX047 | C |
| 48 | WX048 | C |
| 49 | WX049 | C |
| 50 | WX050 | C |
| 51 | WX051 | C |
| 52 | WX052 | C |
| 53 | WX053 | C |
| 54 | WX054 | C |
| 55 | WX055 | C |
| 56 | WX056 | C |
| 57 | WX057 | B |
| 58 | WX058 | C |
| 59 | WX059 | A |
| 60 | WX060 | A |
| 61 | WX061 | A |
| 62 | WX062 | A |
| 63 | WX063 | A |
| 64 | WX064 | B |
| 65 | WX065 | A |
| 66 | WX066 | A |
| 67 | WX067 | A |
| 68 | WX068 | B |
| 69 | WX069 | A |
| 70 | WX070 | B |
| 71 | WX071 | B |
| 72 | WX072 | C |
| 73 | WX073 | C |
| 74 | WX074 | C |
| 75 | WX075 | B |
| 76 | WX076 | B |
| 77 | WX077 | C |
| 78 | WX078 | C |
| 79 | WX079 | B |
| 80 | WX080 | B |
| 81 | WX081 | B |
| 82 | WX082 | C |
| 83 | WX083 | C |
| 84 | WX084 | C |
| 85 | WX085 | C |
| 86 | WX086 | B |
| 87 | WX087 | B |
| 88 | WX088 | A |
| 89 | WX089 | B |
| 90 | WX090 | B |
| 91 | WX091 | A |
| 92 | WX092 | A |
| 93 | WX093 | A |
| 94 | WX094 | A |
| 95 | WX095 | C |
| 96 | WX096 | C |
| 97 | WX097 | C |
| 98 | WX098 | C |
| 99 | WX099 | C |
| 100 | WX100 | C |
| 101 | WX101 | C |
| 102 | WX102 | B |
| 103 | WX103 | B |

A < 2 uM; 2 uM ≤ B ≤ 20 uM; C > 20 uM.

CONCLUSION compounds of the present invention demonstrated significant inhibitory activity against URAT-1.

What is claimed is:

1. A compound represented by formula (I), a pharmaceutically acceptable salt or a tautomer thereof,

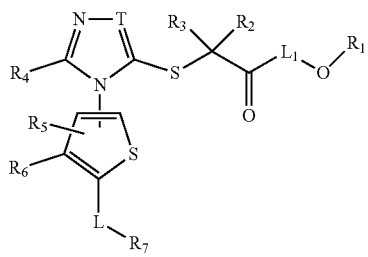

wherein,

T is selected from N or CH;

$R_1$ is selected from H, or selected from the group consisting of $C_{1-6}$ alkyl and $C_{1-6}$ heteroalkyl, each of which is optionally substituted by 1, 2 or 3 of R;

each of $R_2$, $R_3$ is independently selected from H, F, Cl, Br, I, OH, CN, $NH_2$, COOH, or independently selected from the group consisting of $C_{1-6}$ alkyl, $C_{1-6}$ heteroalkyl, phenyl and 5 to 6 membered heteroaryl, each of which is optionally substituted by 1, 2 or 3 of R;

or, $R_2$ and $R_3$ are linked together to form $C_{3-6}$ cycloalkyl or 3 to 6 membered heterocycloalkyl, each of which is optionally substituted by 1, 2 or 3 of R;

$R_4$ is selected from H, F, Cl, Br, I, OH, CN, $NH_2$, COOH, or selected from the group consisting of $C_{1-3}$ alkyl and $C_{1-3}$ heteroalkyl, each of which is optionally substituted by 1, 2 or 3 of R;

$R_5$ is selected from H, F, Cl, Br, I, OH, CN, $NH_2$, or selected from the group consisting of $C_{1-3}$ alkyl and $C_{1-3}$ heteroalkyl, each of which is optionally substituted by 1, 2 or 3 of R;

$R_6$ is selected from H, F, Cl, Br, I, OH, CN, $NH_2$, or selected from the group consisting of $C_{1-3}$ alkyl and $C_{1-3}$ heteroalkyl, each of which is optionally substituted by 1, 2 or 3 of R;

or, $R_5$ and $R_6$ are linked together to form $C_{3-6}$ cycloalkyl or 3 to 6 membered heterocycloalkyl, each of which is optionally substituted by 1, 2 or 3 of R;

L is selected from a single bond, —C(=O)O—, —C(=O)NH—;

$L_1$ is selected from a single bond, —NH—;

$R_7$ is selected from H, F, Cl, Br, I, OH, CN, $NH_2$, COOH, or selected from the group consisting of $C_{1-6}$ alkyl, $C_{1-6}$ heteroalkyl, $C_{3-6}$ cycloalkyl, 3 to 6 membered heterocycloalkyl, phenyl and 5 to 6 membered heteroaryl, each of which is optionally substituted by 1, 2 or 3 of R;

or, $R_6$ and $R_7$ are linked together to form $C_{3-6}$ cycloalkyl, $C_{3-6}$ heterocycloalkyl, phenyl and 5 to 6 membered heteroaryl, each of which is optionally substituted by 1, 2 or 3 of R;

R is selected from F, Cl, Br, I, OH, CN, $NH_2$, COOH, C(=O)$NH_2$, or selected from the group consisting of $C_{1-6}$ alkyl, $C_{1-6}$ heteroalkyl, $C_{3-6}$ cycloalkyl and 3 to 6 membered heteroalkyl, each of which is optionally substituted by 1, 2 or 3 of R';

the moiety

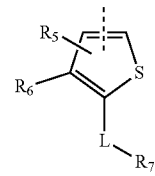

is

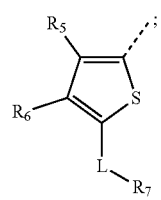

R' is selected from F, Cl, Br, I, OH, CN, $NH_2$, COOH, Me, Et, $CF_3$, $CHF_2$, $CH_2F$, $NHCH_3$, $N(CH_3)_2$;

"hetero" refers to a heteroatom or a heteroatomic group, which is selected from the group consisting of —C(=O)NH—, —NH—, —C(=NH)—, —S(=O)$_2$NH—, —S(=O)NH—, —O—, —S—, =O, =S, —O—N=, —C(=O)O—, —C(=O)—, —C(=S)—, —S(=O)—, —S(=O)$_2$— and —NHC(=O)NH—;

in any case above, the number of the heteroatom or the heteroatomic group is independently selected from 1, 2 or 3, respectively.

2. The compound, the pharmaceutically acceptable salt or the tautomer thereof according to claim 1, wherein, R is selected from F, Cl, Br, I, OH, CN, $NH_2$, COOH, C(=O)$NH_2$, or selected from $C_{1-4}$ alkyl, N,N'-di($C_{1-2}$ alkyl)amino, $C_{1-3}$ alkyl-NH—, $C_{1-3}$ alkyl-O—, $C_{1-3}$ alkyl-S(=O)$_2$—, $C_{1-3}$ alkyl-S(=O)—, each of which is optionally substituted by 1, 2 or 3 of R'.

3. The compound, the pharmaceutically acceptable salt or the tautomer thereof according to claim 2, wherein, R is selected from F, Cl, Br, I, OH, CN, $NH_2$, COOH, C(=O)$NH_2$, Me, $CF_3$, Et, $NH(CH_3)$, $N(CH_3)_2$,

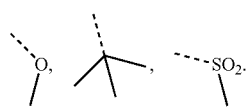

4. The compound, the pharmaceutically acceptable salt or the tautomer thereof according to claim 1, wherein $R_1$ is selected from H, or selected from the group consisting of $C_{1-3}$ alkyl and $C_{1-3}$ heteroalkyl, each of which is optionally substituted by 1, 2 or 3 of R.

5. The compound, the pharmaceutically acceptable salt or the tautomer thereof according to claim 4, wherein, $R_1$ is selected from H, Me, Et.

6. The compound, the pharmaceutically acceptable salt or the tautomer thereof according to claim 1, wherein, each of $R_2$, $R_3$ is independently selected from H, F, Cl, Br, I, OH, CN, $NH_2$, COOH, or independently selected from the group consisting of $C_{1-3}$ alkyl, $C_{1-3}$ heteroalkyl and phenyl, each of which is optionally substituted by 1, 2 or 3 of R;

or, $R_2$ and $R_3$ are linked together to form $C_{4-5}$ cycloalkyl, which is optionally substituted by 1, 2 or 3 of R;

or, $R_2$ and $R_3$ are linked together, and the moiety

is selected from

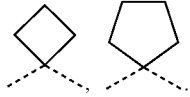

7. The compound, the pharmaceutically acceptable salt or the tautomer thereof according to claim 6, wherein, each of $R_2$, $R_3$ is independently selected from H, Me, Et,

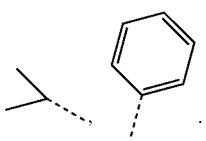

8. The compound, the pharmaceutically acceptable salt or the tautomer thereof according to claim 1, wherein, $R_5$ is selected from H, F, Cl, Br, I, OH, CN, $NH_2$, Me, Et;

or, $R_6$ is selected from H, F, Cl, Br, I, OH, CN, $NH_2$, Me, Et;

or, $R_7$ is selected from H, F, Cl, Br, I, OH, CN, $NH_2$, COOH, or selected from the group consisting of $C_{1-3}$ alkyl, $C(=O)OC_{1-3}$ alkyl, $C(=O)N(C_{1-3}$ alkyl$)C_{1-3}$ alkyl, $C_{3-6}$ cycloalkyl, phenyl, pyrazolyl, imidazolyl, thiazolyl, oxazolyl, isoxazolyl, isothiazolyl, pyridyl and pyrimidyl, each of which is optionally substituted by 1, 2 or 3 of R.

9. The compound, the pharmaceutically acceptable salt or the tautomer thereof according to claim 4, wherein, $R_5$ and $R_6$ are linked together, and the moiety

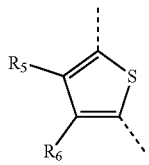

is selected from

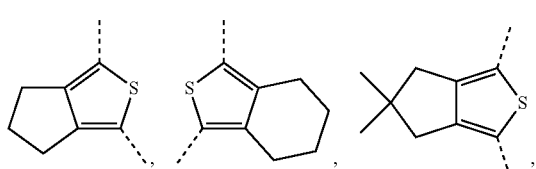

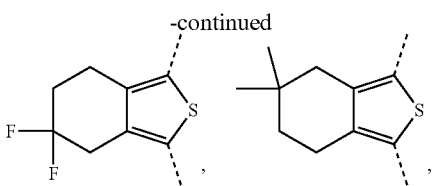

10. The compound, the pharmaceutically acceptable salt or the tautomer thereof according to claim 4, wherein, $R_6$ and $R_7$ are linked together, and the moiety

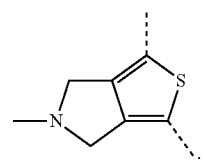

is

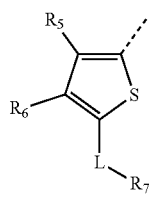

11. The compound, the pharmaceutically acceptable salt or the tautomer thereof according to claim 10, wherein, $R_6$ and $R_7$ are linked together, and the moiety

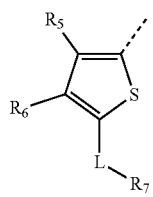

is selected from

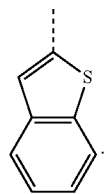

12. The compound, the pharmaceutically acceptable salt or the tautomer thereof according to claim 8, wherein, $R_7$ is selected from H, F, Cl, Br, I, OH, CN, $NH_2$, COOH, or selected from

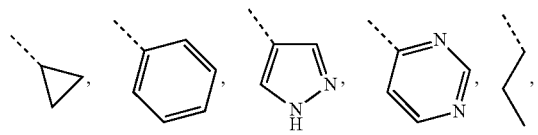

each of which is optionally substituted by 1, 2 or 3 of R.

13. The compound, the pharmaceutically acceptable salt or the tautomer thereof according to claim 12, wherein, $R_7$ is selected from H, F, Cl, Br, I, OH, CN, $NH_2$, COOH,

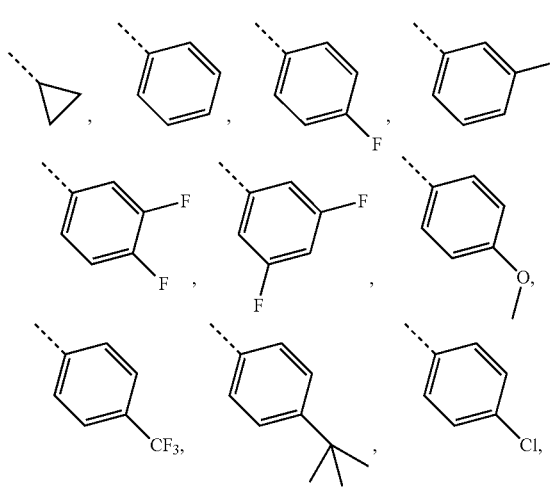

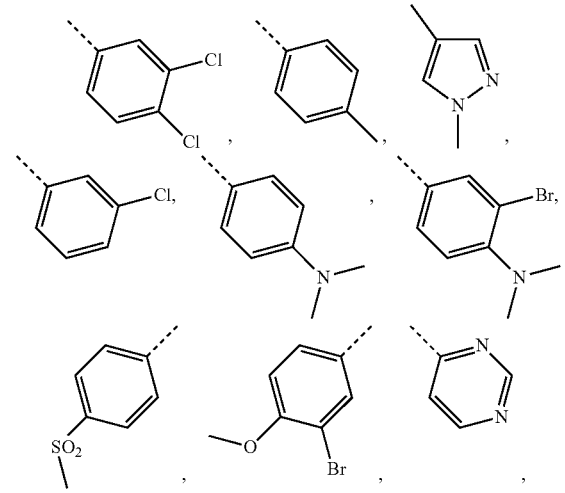

-continued

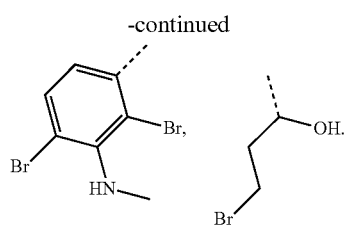

14. The compound, the pharmaceutically acceptable salt or the tautomer thereof according to claim 1, wherein, the moiety -L-$R_7$ is selected from H, or, $R_4$ is selected from F, Cl, Br, I, OH, CN, $NH_2$, COOH, Me, Et, n-propyl, i-propyl, $CF_3$, $CHF_2$, $CH_2F$, $NHCH_3$, $N(CH_3)_2$.

15. The compound, the pharmaceutically acceptable salt or the tautomer thereof according to claim 1, which is selected from

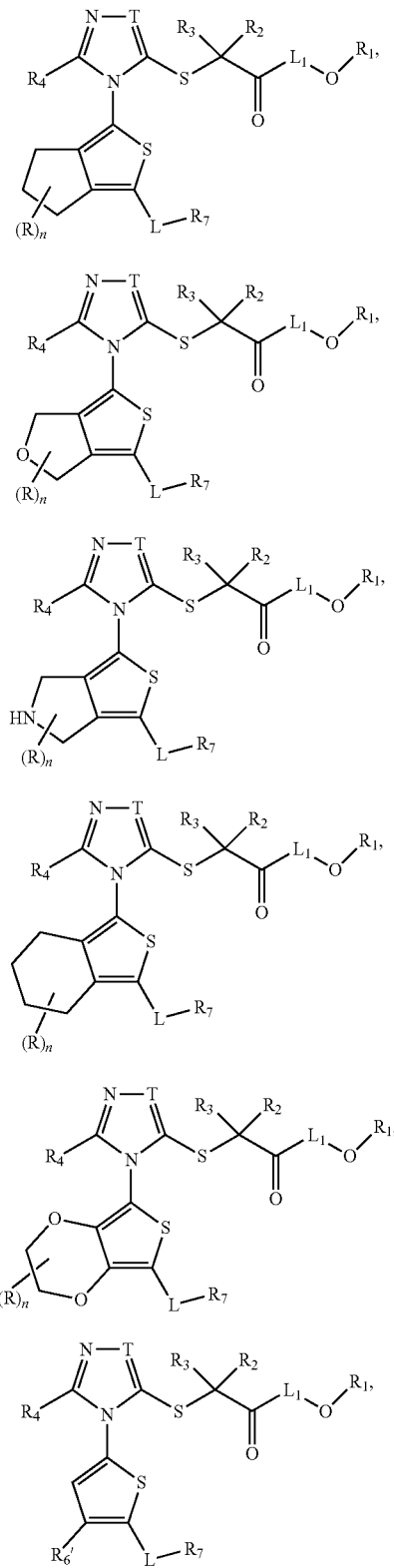

wherein, n is selected from 0, 1, 2 or 3;

$R_6'$ is selected from H, F, Cl, Br, I, OH, $NH_2$, Me, Et, n-propyl, i-propyl, $CF_3$, $CHF_2$, $CH_2F$, $NHCH_3$, $N(CH_3)_2$;

$R_1$, $R_2$, $R_3$, $R_4$, $R_7$, T, L, $L_1$ are as defined as claim 1.

16. A compound, a pharmaceutically acceptable salt or a tautomer thereof, wherein the compound is selected from the group consisting of

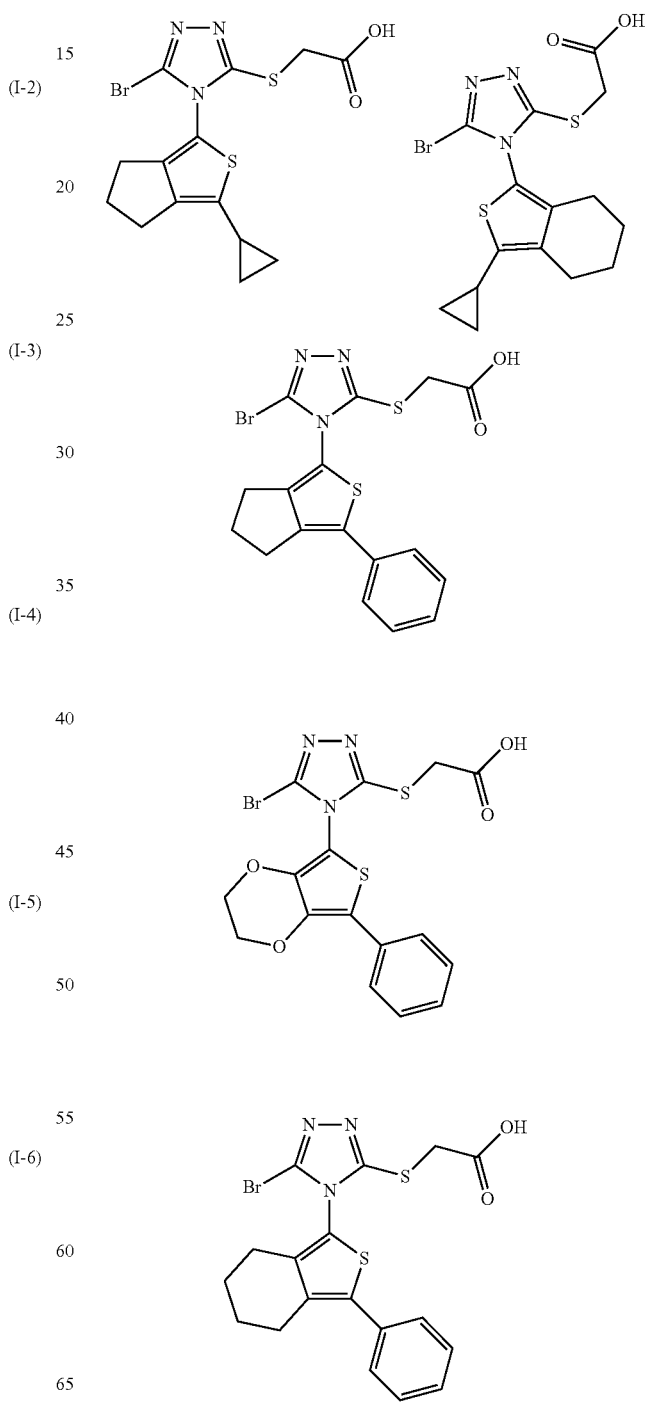

129
-continued
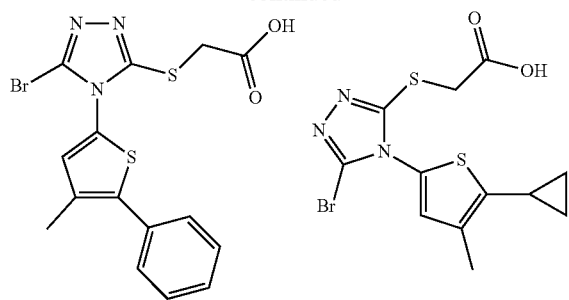
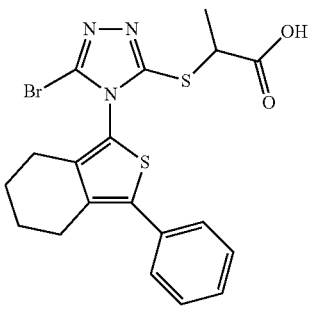
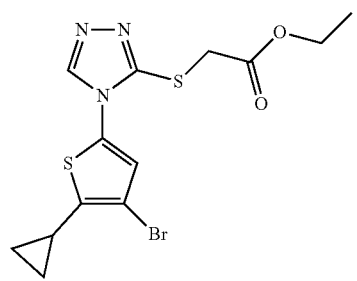
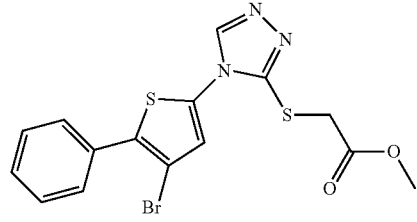
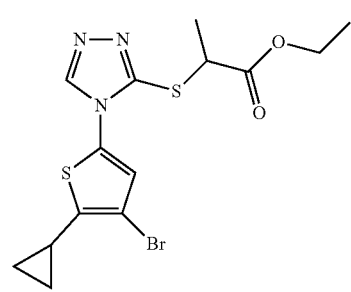
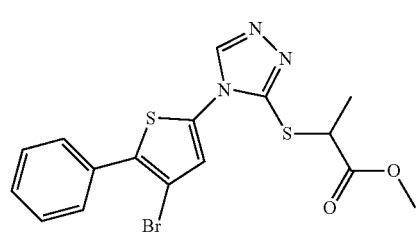
130
-continued
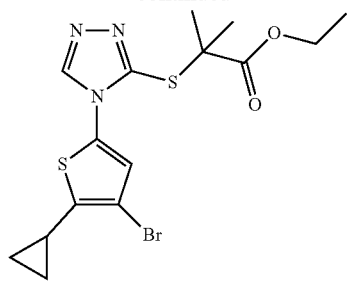
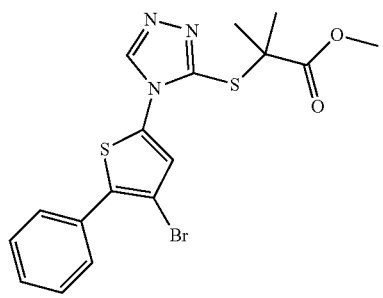
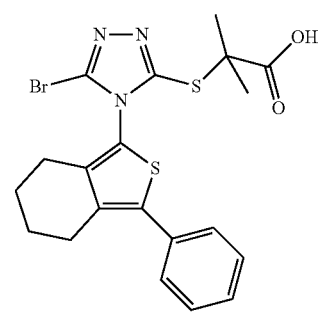
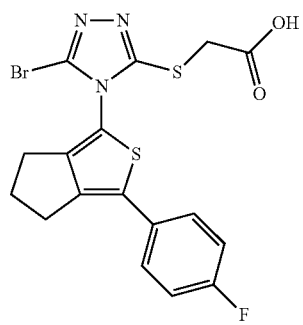
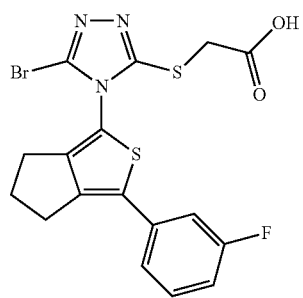

131 -continued
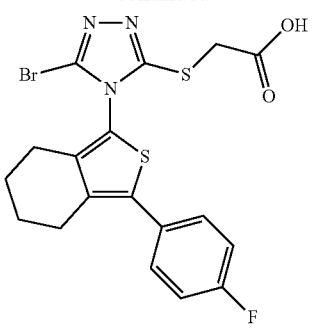
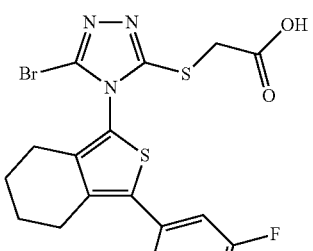
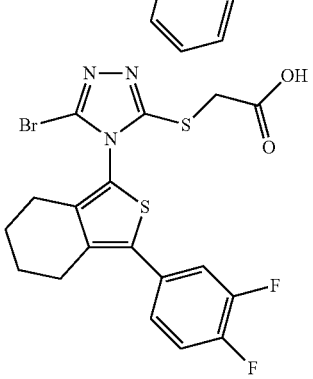
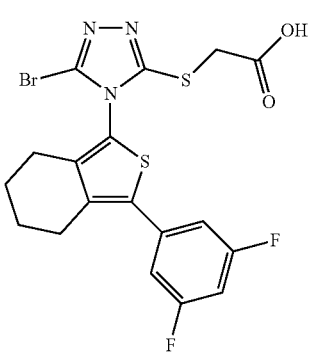
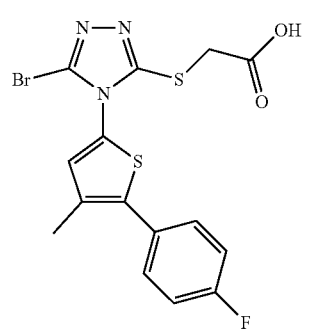
132 -continued
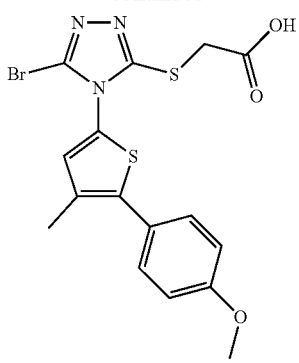
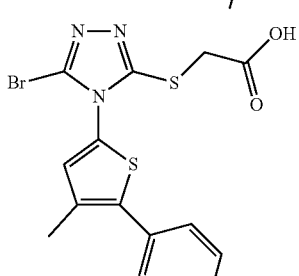
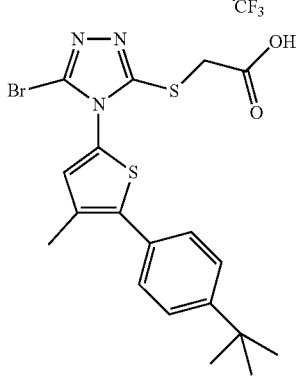
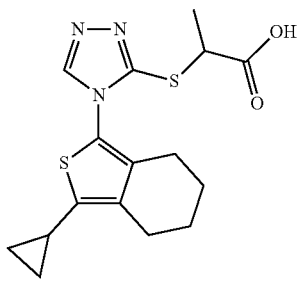
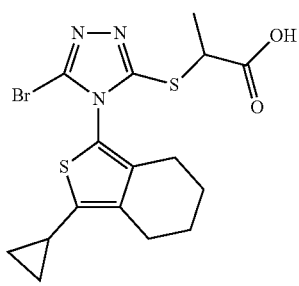

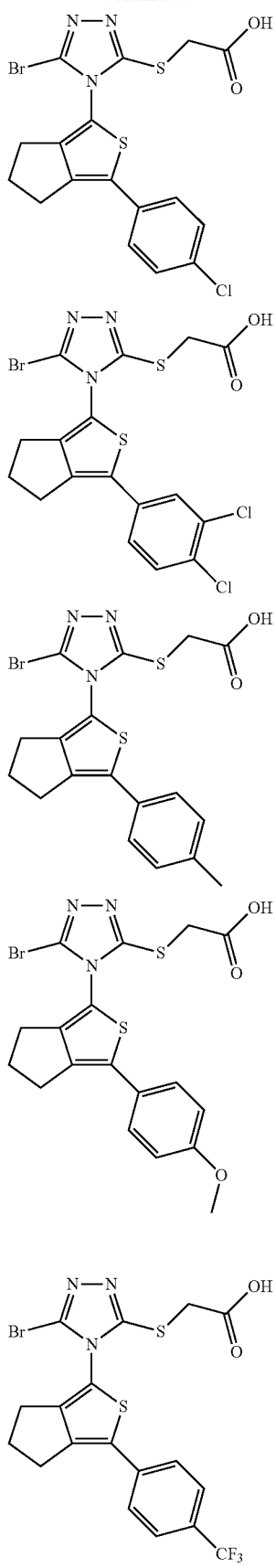
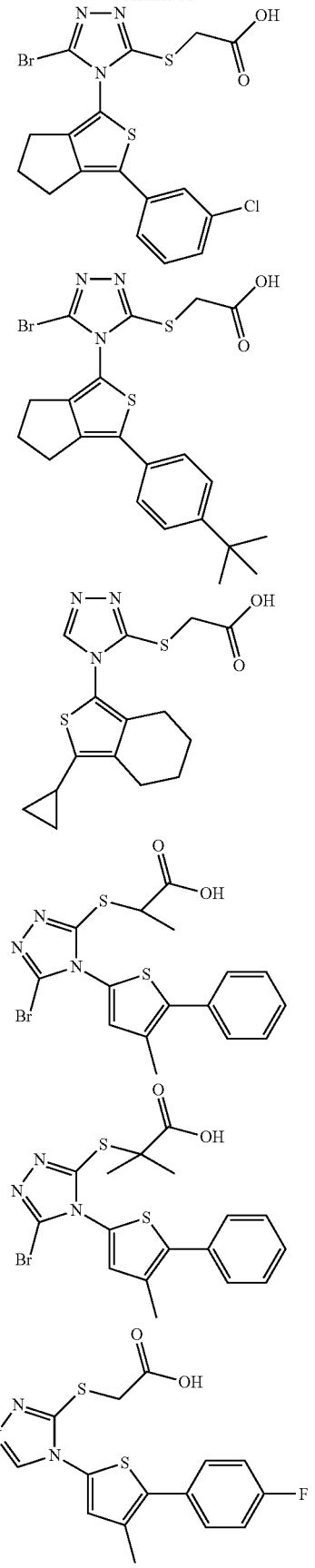

135
-continued
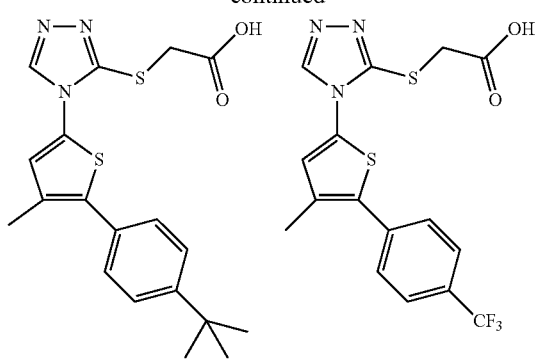
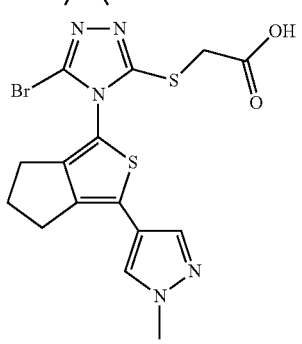
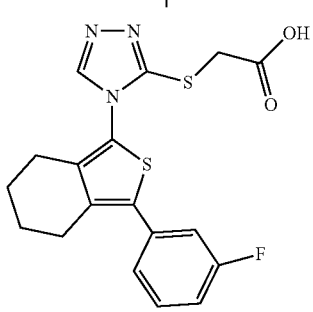
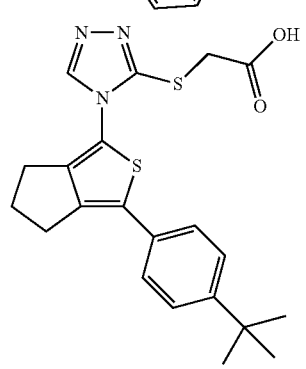
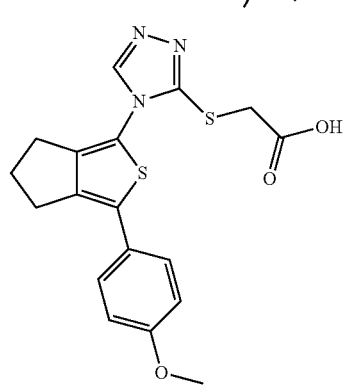
136
-continued
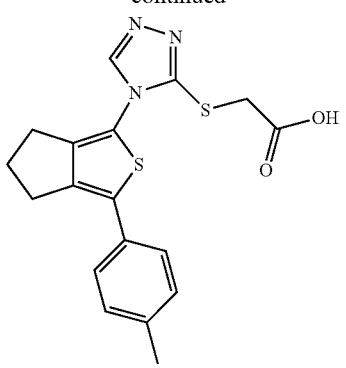
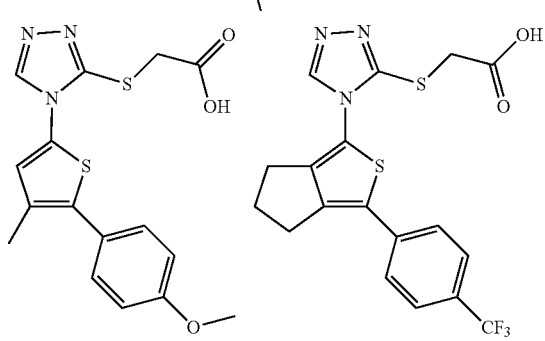
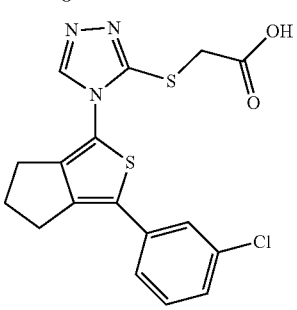
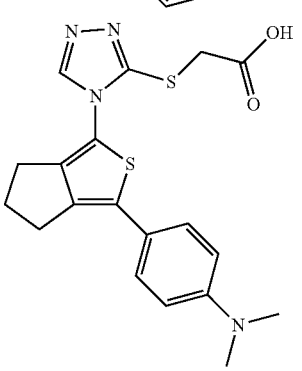
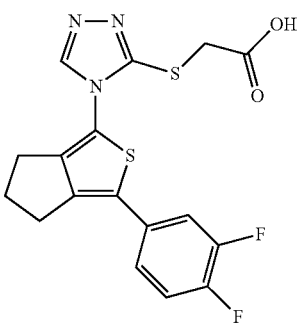

137
-continued
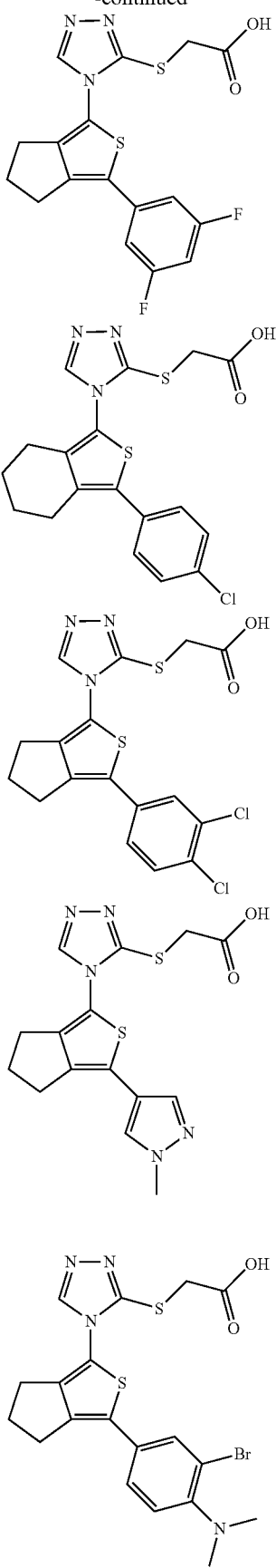
138
-continued
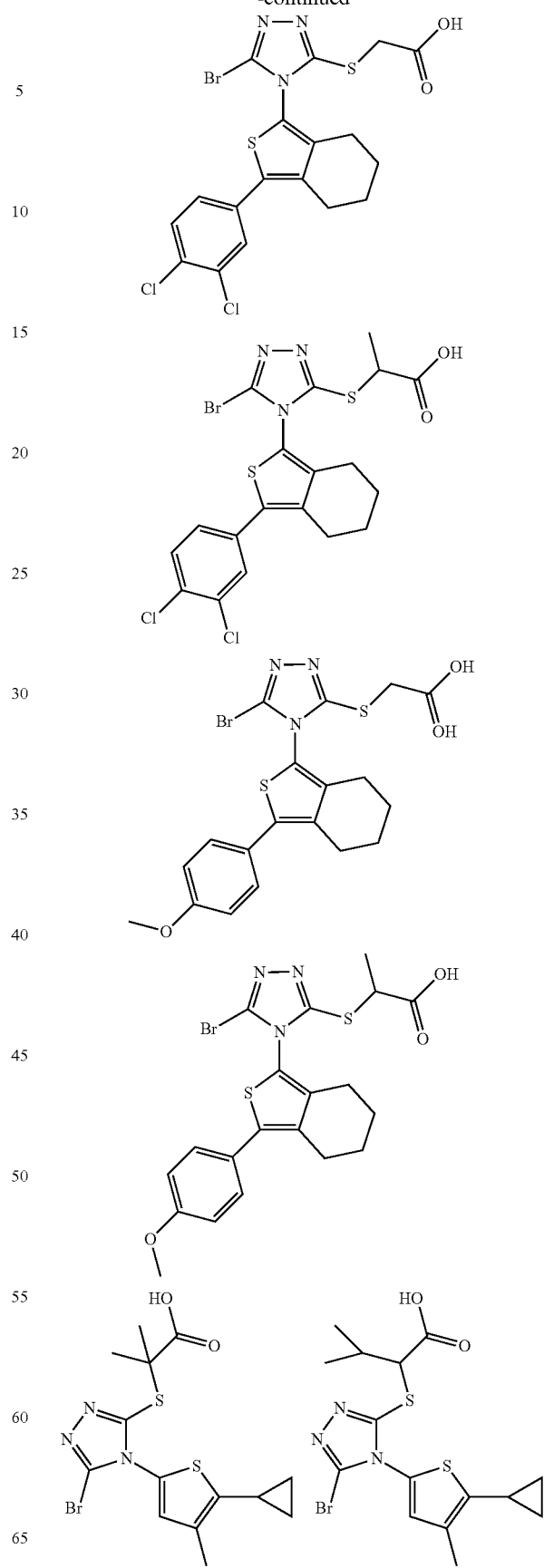

139
-continued
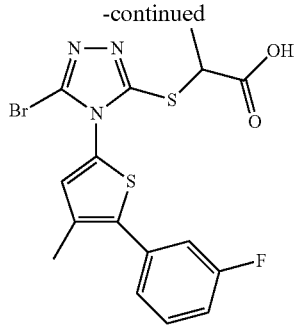
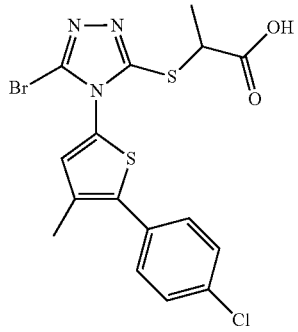
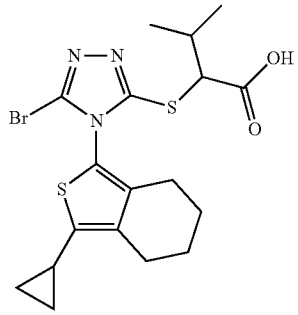
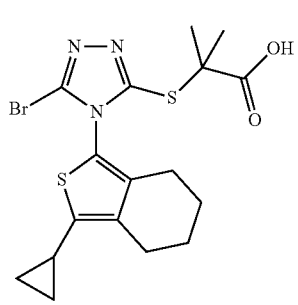
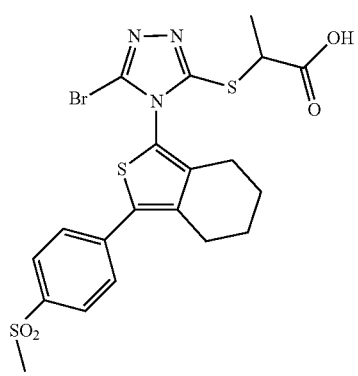
140
-continued
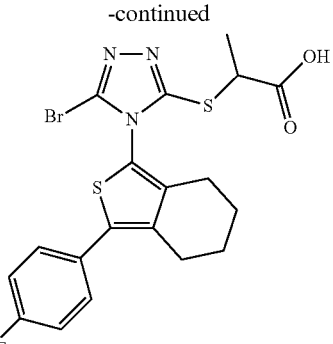
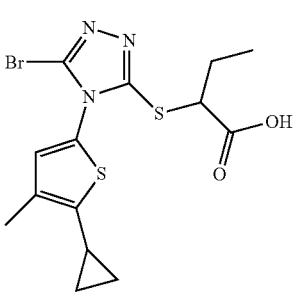
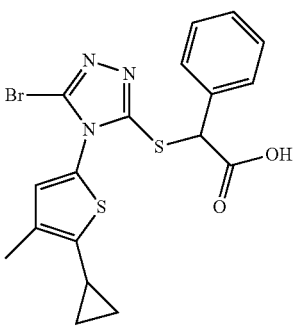
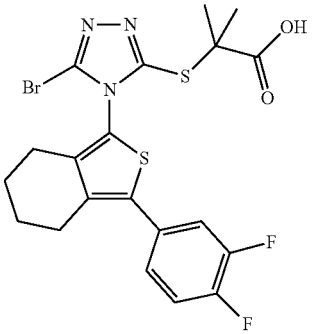
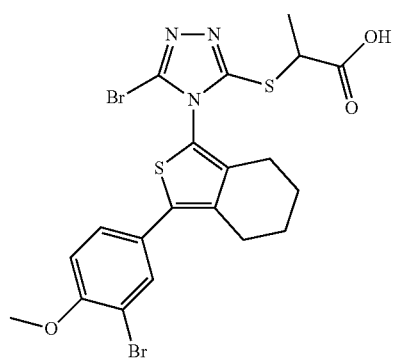

-continued
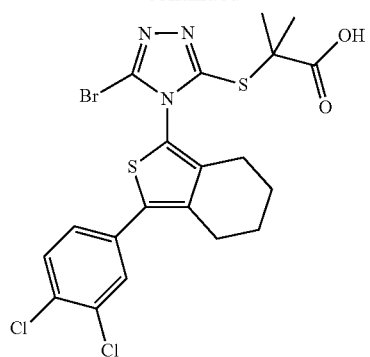
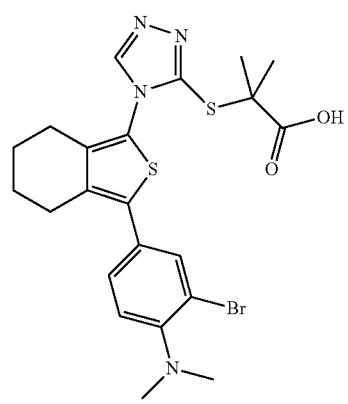 [SMILES: CN(C)c1ccc(-c2sc(-n3cnnc3SC(C)(C)C(=O)O)c3c2CCCC3)cc1Br]
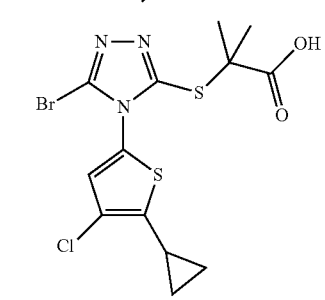
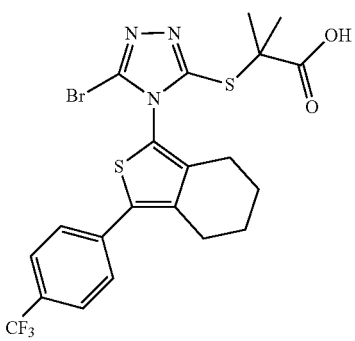
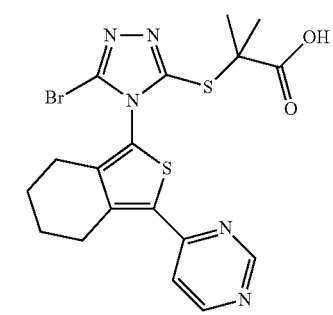
-continued
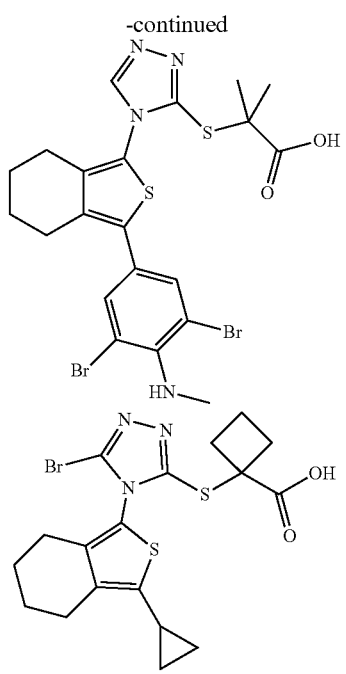
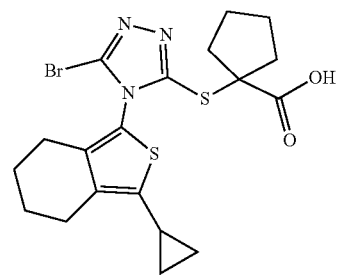
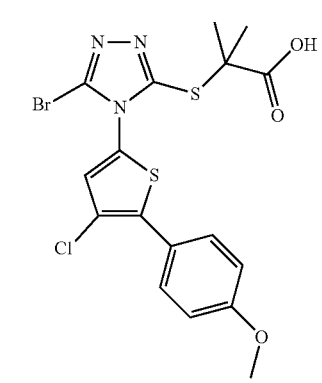
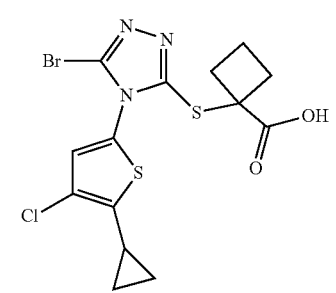

-continued
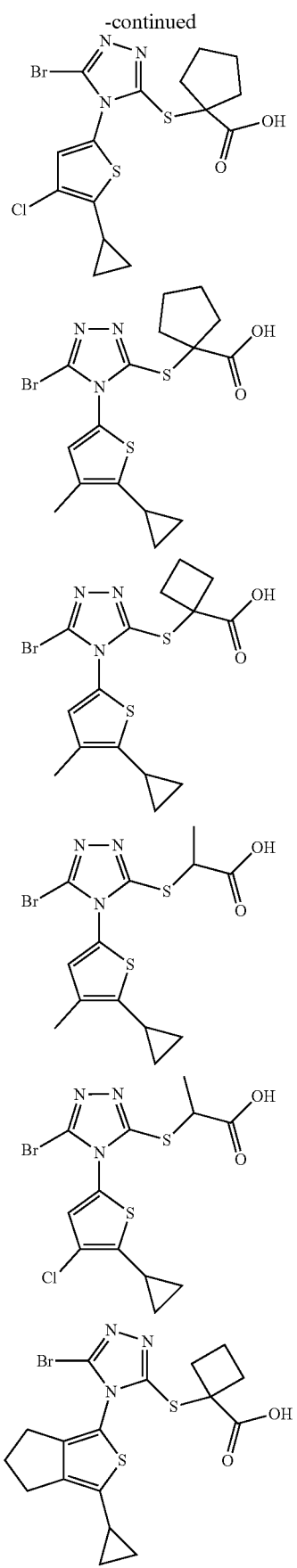
-continued
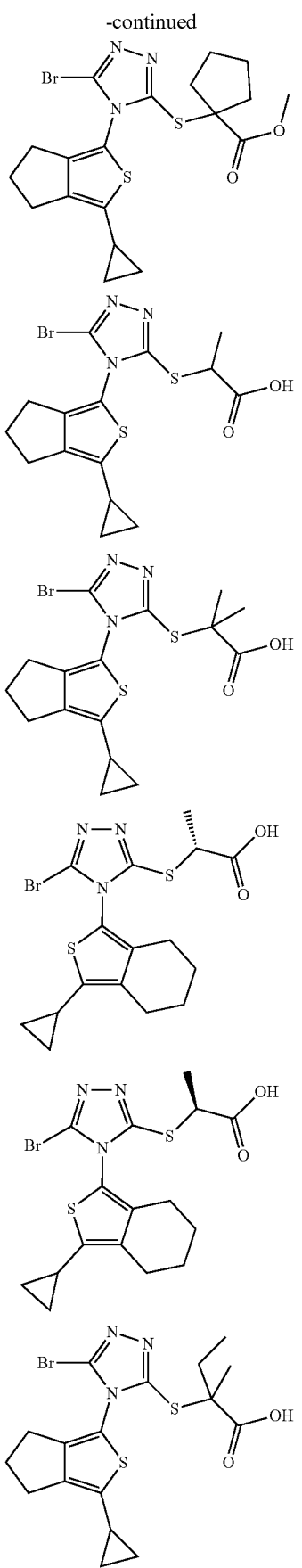

-continued
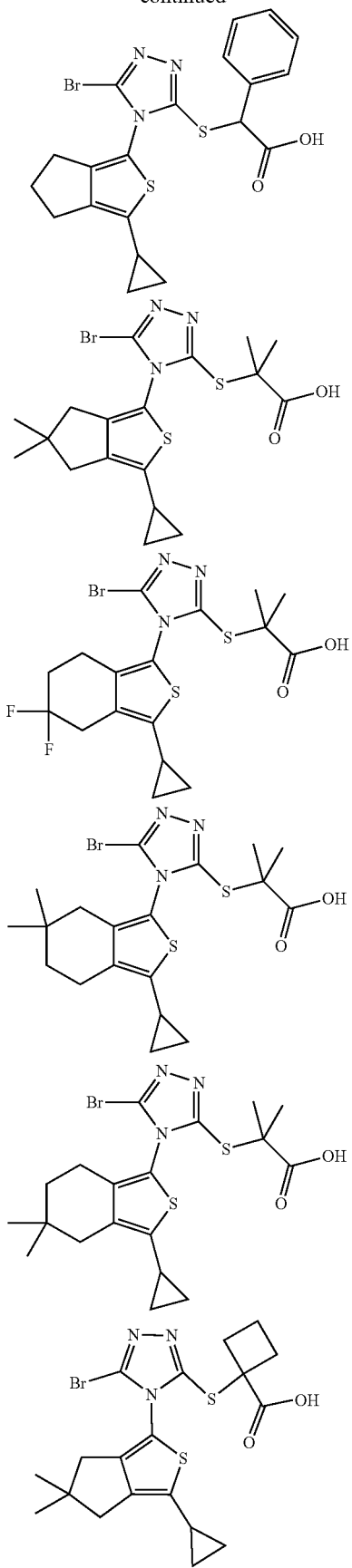
-continued
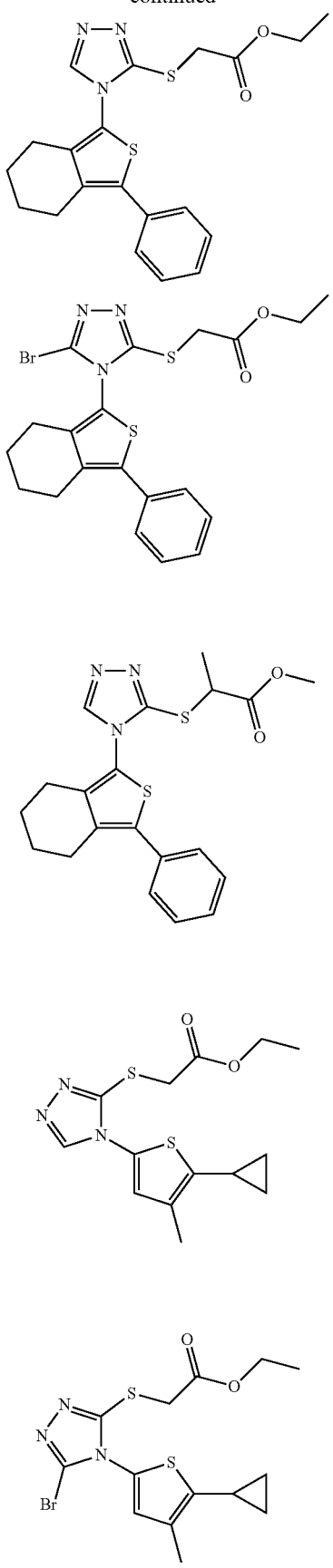

147
-continued
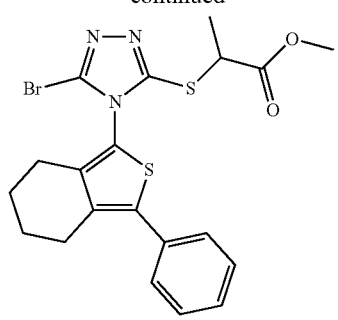
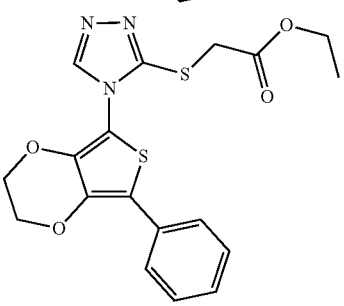
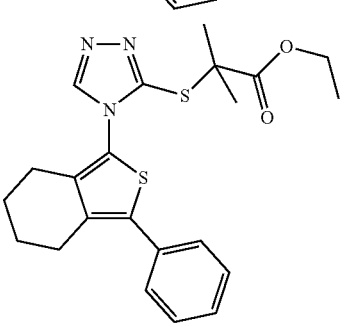
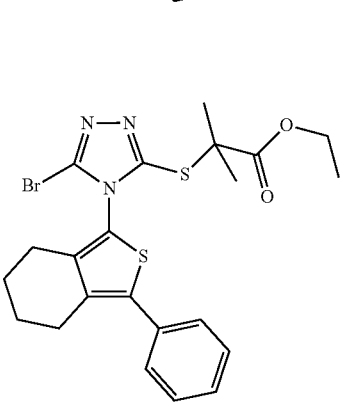
148
-continued
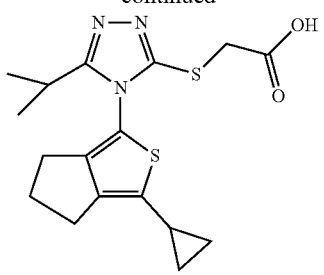
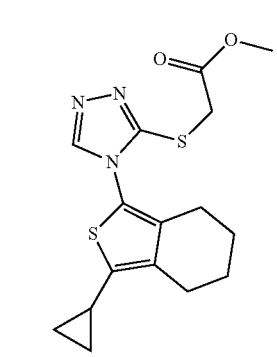
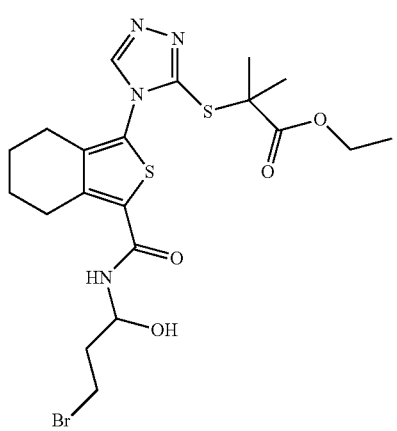
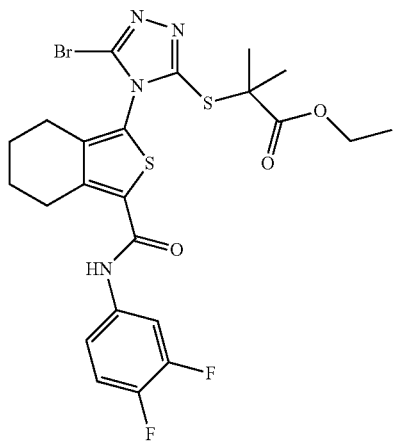

149
-continued

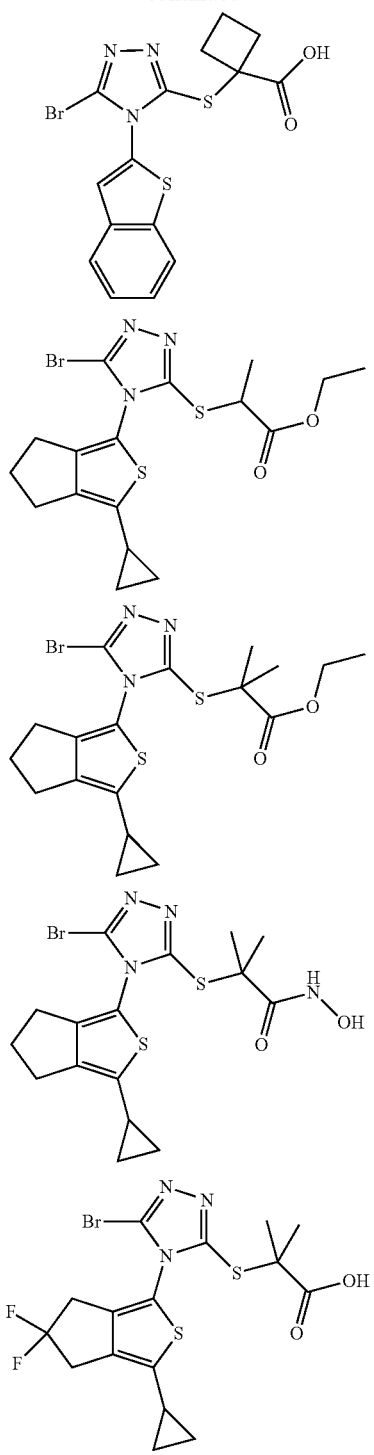

150
-continued

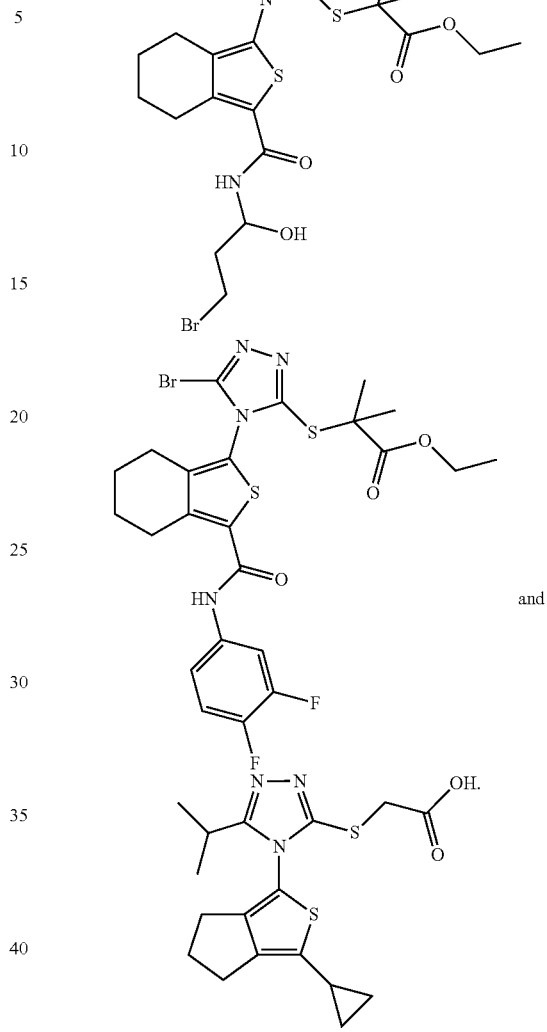

and

17. A pharmaceutical composition, comprising the compound, the pharmaceutically acceptable salt thereof or the tautomer thereof according to claim 1, as well as one or more than one pharmaceutically acceptable excipients.

18. A method of inhibiting uric acid transporter (URAT1) using the compound, the pharmaceutically acceptable salt thereof or the tautomer thereof according to claim 1.

19. A process for preventing and/or treating a disease related to abnormal uric acid levels in a subject in need thereof, comprising: administering an effective amount of the compound, the pharmaceutically acceptable salt thereof or the tautomer thereof according to claim 1 to the subject.

* * * * *